(12) United States Patent
Vacca et al.

(10) Patent No.: US 8,293,731 B2
(45) Date of Patent: Oct. 23, 2012

(54) HIV INTEGRASE INHIBITORS

(75) Inventors: Joseph P. Vacca, Telford, PA (US); John S. Wai, Harleysville, PA (US); Linda S. Payne, Lansdale, PA (US)

(73) Assignee: Merck Sharp + Dohme Corp., Rahway, NJ (US)

(*) Notice: Subject to any disclaimer, the term of this patent is extended or adjusted under 35 U.S.C. 154(b) by 0 days.

(21) Appl. No.: 13/107,512

(22) Filed: May 13, 2011

(65) Prior Publication Data

US 2011/0275621 A1 Nov. 10, 2011

Related U.S. Application Data

(62) Division of application No. 12/760,638, filed on Apr. 15, 2010, now Pat. No. 7,968,564, which is a division of application No. 11/920,032, filed as application No. PCT/US2006/017369 on May 5, 2006, now Pat. No. 7,741,315.

(60) Provisional application No. 60/679,431, filed on May 10, 2005.

(51) Int. Cl.
 *A01N 43/62* (2006.01)
 *A61K 31/55* (2006.01)
 *C07D 487/00* (2006.01)

(52) U.S. Cl. ......... 514/220; 540/495; 540/496; 540/497

(58) Field of Classification Search .................. 540/495, 540/496, 497; 514/220
See application file for complete search history.

(56) References Cited

U.S. PATENT DOCUMENTS

| | | |
|---|---|---|
| 6,262,055 B1 | 7/2001 | Young et al. |
| 6,306,891 B1 | 10/2001 | Selnick et al. |
| 6,380,249 B1 | 4/2002 | Young et al. |
| 6,841,558 B2 | 1/2005 | Anthony et al. |
| 6,919,351 B2 | 7/2005 | Anthony et al. |
| 6,921,759 B2 | 7/2005 | Anthony et al. |
| 7,109,186 B2 | 9/2006 | Walker et al. |
| 7,169,780 B2 | 1/2007 | Crescenzi et al. |
| 7,211,572 B2 | 5/2007 | Miyazaki et al. |
| 7,217,713 B2 | 5/2007 | Crescenzi et al. |
| 7,232,819 B2 | 6/2007 | Di Francesco et al. |
| 7,279,487 B2 | 10/2007 | Egbertson et al. |
| 7,435,734 B2 | 10/2008 | Crescenzi et al. |
| 7,459,452 B2 | 12/2008 | Di Francesco et al. |
| 7,598,264 B2 | 10/2009 | Han et al. |
| 7,619,086 B2 | 11/2009 | Morrissette et al. |
| 2003/0229079 A1 | 12/2003 | Payne et al. |
| 2004/0229909 A1 | 11/2004 | Kiyama et al. |
| 2005/0010048 A1 | 1/2005 | Zhuang et al. |
| 2007/0161639 A1 | 7/2007 | Jones et al. |

FOREIGN PATENT DOCUMENTS

| | | |
|---|---|---|
| WO | 2005/086700 A2 | 11/2005 |
| WO | 2006/116764 A1 | 11/2006 |

OTHER PUBLICATIONS

Pearl, L. et al. "A structural model for the retroviral proteases", Nature, 1987, vol. 329, pp. 351-354.
Power, M. et al. "Nucleotide Sequence of SRV-1, a Type D Simian Acquired Immune Deficiency Syndrome Retrovirus", Science, 1986, vol. 231, pp. 1567-1572.
Rater. L. et al. "Complete nucleotide sequence of the AIDS virus, HTLV-III", Nature, 1985, vol. 313, pp. 277-284.
Toh, H. et al. "Close structural resemblance between putative polymerase of a Drosophila transposable genetic element 17.6 and pol gene product of Moloney murine leukaemia virus", The EMBO Journal, 1985, vol. 4, pp. 1267-1272.

*Primary Examiner* — Paul V. Ward
(74) *Attorney, Agent, or Firm* — Sheldon Heber; Jeffrey P Bergman

(57) ABSTRACT

Tricyclic compounds of Formula I are inhibitors of HIV integrase and inhibitors of HIV replication:

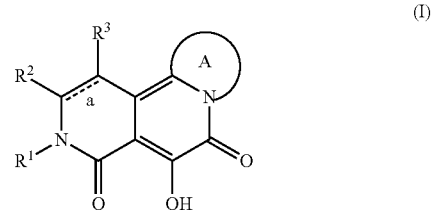

wherein bond a, ring A, $R^1$, $R^2$ and $R^3$ are defined herein. The compounds are useful for the prophylaxis or treatment of infection by HIV and the prophylaxis, treatment, or delay in the onset of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

11 Claims, No Drawings

HIV INTEGRASE INHIBITORS

RELATED APPLICATIONS

This application is a divisional of pending U.S. Ser. No. 12/760,638, filed Apr. 15, 2010, now U.S. Pat. No. 7,968,564 which is a divisional of U.S. Ser. No. 11/920,032, filed Nov. 11, 2007 and granted on Jun. 22, 2010 as U.S. Pat. No. 7,741,315, which is the National Stage of International Application No. PCT/US2006/017369, filed on May 5, 2006, which claims the benefit of U.S. Provisional Application No. 60/679,431 (filed May 10, 2005), the disclosure of which is hereby incorporated by reference in its entirety.

FIELD OF THE INVENTION

The present invention is directed to tricyclic analogs of hydroxy polyhydro-2,6-naphthyridine dione compounds and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for preventing or treating or delaying the onset of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:
U.S. Pat. No. 6,380,249, U.S. Pat. No. 6,306,891, and U.S. Pat. No. 6,262,055 disclose 2,4-dioxobutyric acids and acid esters useful as HIV integrase inhibitors.

WO 01/00578 discloses 1-(aromatic or heteroaromatic-substituted)-3-(heteroaromatic substituted)-1,3-propanediones useful as HIV integrase inhibitors.

US 2003/0055071 (corresponding to WO 02/30930), WO 02/30426, and WO 02/55079 each disclose certain 8-hydroxy-1,6-naphthyridine-7-carboxamides as HIV integrase inhibitors.

WO 02/036734 discloses certain aza- and polyaza-naphthalenyl ketones to be HIV integrase inhibitors.

WO 03/016275 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

WO 04/004657 discloses certain hydroxypyrrole derivatives that are HIV integrase inhibitors.

WO 2005/016927 discloses certain nitrogenous condensed ring compounds that are HIV integrase inhibitors.

SUMMARY OF THE INVENTION

The present invention is directed to tricyclic analogs of hydroxy polyhydro-2,6-naphthyridine dione compounds. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes compounds of Formula I, and pharmaceutically acceptable salts thereof:

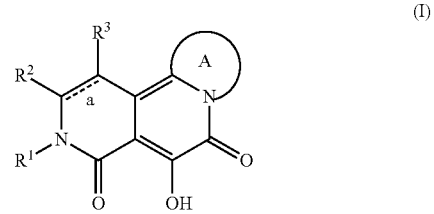

(I)

wherein:
bond "$\underset{a}{\text{-----}}$" in the ring is a single bond or a double bond;
$R^1$ is $C_{1-6}$ alkyl, $R^J$, or $C_{1-6}$ alkyl substituted with $R^J$ wherein $R^J$ is CycA, AryA, HetA, or HetP;
$R^2$ is H or $C_{1-6}$ alkyl;
$R^3$ is:
(1) H,
(2) halogen,
(3) CN,
(4) $C_{1-6}$ alkyl,
(5) $C_{1-6}$ haloalkyl,
(6) $C_{1-6}$ alkyl substituted with OH, O—$C_{1-6}$ alkyl, O—$C_{1-6}$ haloalkyl, CN, N($R^A$)$R^B$, C(O)N($R^A$)$R^B$, C(O)$R^A$, $CO_2R^A$, C(O)—N($R^A$)—$C_{1-6}$ alkylene-O$R^B$ with the proviso that the N(R$^A$) moiety and the OR$^B$ moiety are not both attached to the same carbon of the C$_{1-6}$ alkylene moiety, SR$^A$, S(O)R$^A$, SO$_2$R$^A$, SO$_2$N(R$^A$)R$^B$, N(R$^A$)C(O)R$^B$, N(R$^A$)CO$_2$R$^B$, N(R$^A$)SO$_2$R$^B$, N(R$^A$)SO$_2$N(R$^A$)R$^B$, N(R$^A$)C(O)N(R$^A$)R$^B$, or OC(O)N(R$^A$)R$^B$, (7) C(O)R$^A$,
(8) CO$_2$R$^A$,
(9) C(O)N(R$^A$)R$^B$,
(10) C(O)—N(R$^A$)—C$_{1-6}$ alkylene-OR$^B$ with the proviso that the N(R$^A$) moiety and the OR$^B$ moiety are not both attached to the same carbon of the C$_{1-6}$ alkylene moiety,
(11) SR$^A$,
(12) S(O)R$^A$,
(13) SO$_2$R$^A$,
(14) SO$_2$N(R$^A$)R$^B$,
(15) N(R$^A$)R$^B$,
(16) N(R$^A$)C(O)R$^B$,
(17) N(R$^A$)C(O)OR$^B$;
(18) N(R$^A$)C(O)N(R$^A$)R$^B$,
(19) N(R$^A$)C(O)C(O)N(R$^A$)R$^B$,
(20) N(R$^A$)SO$_2$R$^B$,
(21) N(R$^A$)SO$_2$N(R$^A$)R$^B$,
(22) OC(O)N(R$^A$)R$^B$, or
(23) Y—R$^K$ wherein:
   Y is a single bond, C$_{1-6}$ alkylene, O, O—C$_{1-6}$ alkylene, C$_{1-6}$ alkylene-O, C(O), C(O)—C$_{1-6}$ alkylene, C$_{1-6}$ alkylene-C(O), C(O)—C$_{1-6}$ alkylene-O, C(O)—C$_{1-6}$ alkylene-O—C$_{1-6}$ alkylene, C(O)N(R$^A$), C(O)N(R$^A$)—C$_{1-6}$ alkylene, C$_{1-6}$ alkylene-C(O)N(R$^A$), C$_{1-6}$ alkylene-C(O)N(R$^A$)—C$_{1-6}$ alkylene, S(O), S(O)$_2$, S(O)—C$_{1-6}$ alkylene, S(O)$_2$—C$_{1-6}$ alkylene, C$_{1-6}$ alkylene-S(O), or C$_{1-6}$ alkylene-S(O)$_2$; and
   R$^K$ is CycB, AryB, HetB, or HetQ;

or, as an alternative, when bond "$\underline{\text{a}}$" is a double bond, R$^2$ and R$^3$ together with the carbon atoms to which each is attached form:
(i) a benzene ring which is optionally substituted with a total of from 1 to 4 substituents wherein (a) from zero to 4 substituents are each independently one of substituents (1) to (25) as defined in part (i) of the definition of AryA and (b) from zero to 2 substituents are each independently one of the substituents (1) to (6) as defined in part (ii) of the definition of AryA, or
(ii) a 5- or 6-membered heteroaromatic ring containing from 1 to 4 heteroatoms independently selected from N, O and S, wherein the heteroaromatic ring is optionally substituted with a total of from 1 to 3 substituents wherein (a) from zero to 3 substituents are each independently one of substituents (1) to (26) as defined in part (i) of the definition of HetA and (b) from zero to 2 substituents are each independently one of the substituents (1) to (6) as defined in part (ii) of the definition of HetA;

ring A is a 5- to 9-membered, saturated or mono-unsaturated heterocyclic ring containing in addition to the nitrogen shared with the naphthyridine ring from 1 to 3 heteroatoms independently selected from N, O, and S, wherein each s is optionally oxidized to S(O) or S(O)$_2$; and wherein the saturated or mono-unsaturated heterocyclic ring is optionally substituted with a total of from 1 to 10 substituents, wherein:
(i) from zero to 10 substituents are each independently:
   (1) halogen,
   (2) C$_{1-6}$ alkyl,
   (3) C$_{1-6}$ haloalkyl,
   (4) C$_{1-6}$ alkyl substituted with OH, O—C$_{1-6}$ alkyl, O—C$_{1-6}$ haloalkyl, CN, N(R$^A$)R$^B$, C(O)N(R$^A$)R$^B$, C(O)R$^A$, C(O)$_2$R$^A$, C(O)—N(R$^A$)—C$_{1-6}$ alkylene-OR$^B$ with the proviso that the N(R$^A$) moiety and the OR$^B$ moiety are not both attached to the same carbon of the C$_{1-6}$ alkylene moiety, SR$^A$, S(O)R$^A$, SO$_2$R$^A$, SO$_2$N(R$^A$)R$^B$, N(R$^A$)C(O)R$^B$, N(R$^A$)CO$_2$R$^B$, N(R$^A$)SO$_2$R$^B$, N(R$^A$)SO$_2$N(R$^A$)R$^B$, N(R$^A$)C(O)N(R$^A$)R$^B$, OC(O)N(R$^A$)R$^B$; or OC(O)R$^A$,
   (5) O—C$_{1-6}$ alkyl,
   (6) O—C$_{1-6}$ haloalkyl,
   (7) oxo,
   (8) =C(R$^A$)R$^B$,
   (9) C(O)N(R$^A$)R$^B$,
   (10) C(O)C(O)N(R$^A$)R$^B$,
   (11) C(O)R$^A$,
   (12) CO$_2$R$^A$,
   (13) SR$^A$,
   (14) S(O)R$^A$,
   (15) SO$_2$R$^A$,
   (16) SO$_2$N(R$^A$)R$^B$, or
   (17) OH, and
(ii) from zero to 3 substituents are each Z—R$^L$, wherein:
   each Z is independently a single bond, C$_{1-6}$ alkylene, O, O—C$_{1-6}$ alkylene, C$_{1-6}$ alkylene-O, C(O), C(O)—C$_{1-6}$ alkylene, C$_{1-6}$ alkylene-C(O), C(O)—C$_{1-6}$ alkylene-O, C(O)—C$_{1-6}$ alkylene-O—C$_{1-6}$ alkylene, C(O)N(R$^A$), C(O)N(R$^A$)—C$_{1-6}$ alkylene, C$_{1-6}$ alkylene-C(O)N(R$^A$), C$_{1-6}$ alkylene-C(O)N(R$^A$)—C$_{1-6}$ alkylene, S(O), S(O)$_2$, S(O)—C$_{1-6}$ alkylene, S(O)$_2$—C$_{1-6}$ alkylene, C$_{1-6}$ alkylene-S(O), or C$_{1-6}$ alkylene-S(O)$_2$; and
   each R$^L$ is independently CycC, AryC, HetC, or HetR;

each R$^A$ is independently H or C$_{1-6}$ alkyl;
each R$^B$ is independently H or C$_{1-6}$ alkyl;
CycA is a C$_{3-8}$ cycloalkyl which is optionally substituted with a total of from 1 to 6 substituents, wherein:
(i) from zero to 6 substituents are each independently:
   (1) halogen,
   (2) CN
   (3) C$_{1-6}$ alkyl,
   (4) OH,
   (5) O—C$_{1-6}$ alkyl,
   (6) C$_{1-6}$ haloalkyl, or
   (7) O—C$_{1-6}$ haloalkyl, and
(ii) from zero to 2 substituents are each independently:
   (1) CycD,
   (2) AryD,
   (3) HetD,
   (4) HetZ,
   (5) C$_{1-6}$ alkyl substituted with CycD, AryD, HetD, or HetZ, or
   (6) C(O)-HetZ or C(O)C(O)-HetZ;
CycB independently has the same definition as CycA;
each CycC independently has the same definition as CycA;
AryA is an aryl which is optionally substituted with a total of from 1 to 5 substituents, wherein:
(i) from zero to 5 substituents are each independently:
   (1) C$_{1-6}$ alkyl,
   (2) C$_{1-6}$ alkyl substituted with OH, O—C$_{1-6}$ alkyl, O—C$_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, SO$_2$R$^A$, SO$_2$N(R$^A$)R$^B$, N(R$^A$)C(O)R$^B$, N(R$^A$)CO$_2$R$^B$, N(R$^A$)SO$_2$R$^B$, N(R$^A$)SO$_2$N(R$^A$)R$^B$, OC(O)N(R$^A$)R$^B$, N(R$^A$)C(O)N(R$^A$)R$^B$, or N(R$^A$)C(O)C(O)N(R$^A$)R$^B$,
   (3) O—C$_{1-6}$ alkyl,
   (4) C$_{1-6}$ haloalkyl,
   (5) O—C$_{1-6}$ haloalkyl,
   (6) OH, (7) halogen,
(8) CN,
(9) $NO_2$,
(10) $N(R^A)R^B$,
(11) $C(O)N(R^A)R^B$,
(12) $C(O)R^A$,
(13) C(O)—$C_{1-6}$ haloalkyl,
(14) $C(O)OR^A$,
(15) $OC(O)N(R^A)R^B$,
(16) $SR^A$,
(17) $S(O)R^A$,
(18) $SO_2R^A$,
(19) $SO_2N(R^A)R^B$,
(20) $N(R^A)SO_2R^B$,
(21) $N(R^A)SO_2N(R^A)R^B$,
(22) $N(R^A)C(O)R^B$,
(23) $N(R^A)C(O)N(R^A)R^B$,
(24) $N(R^A)C(O)C(O)N(R^A)R^B$, or
(25) $N(R^A)CO_2R^B$, and (ii) from zero to 2 substituents are each independently:
(1) CycD,
(2) AryD,
(3) HetD,
(4) HetZ,
(5) $C_{1-6}$ alkyl substituted with CycD, AryD, HetD, or HetZ, or
(6) C(O)-HetZ or C(O)C(O)-HetZ;

AryB independently has the same definition as AryA;
each AryC independently has the same definition as AryA;
HetA is a heteroaryl which is optionally substituted with a total of from 1 to 5 substituents, wherein:
(i) from zero to 5 substituents are each independently:
(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, $N(R^A)C(O)R^B$, $N(R^A)CO_2R^B$, $N(R^A)SO_2R^B$, $N(R^A)SO_2N(R^A)R^B$, $OC(O)N(R^A)R^B$, $N(R^A)C(O)N(R^A)R^B$, or $N(R^A)C(O)C(O)N(R^A)R^B$,
(3) O—$C_{1-6}$ alkyl,
(4) $C_{1-6}$ haloalkyl,
(5) O—$C_{1-6}$ haloalkyl,
(6) OH,
(7) oxo,
(8) halogen,
(9) CN,
(10) $NO_2$,
(11) $N(R^A)R^B$,
(12) $C(O)N(R^A)R^B$,
(13) $C(O)R^A$,
(14) C(O)—$C_{1-6}$ haloalkyl,
(15) $C(O)OR^A$,
(16) $OC(O)N(R^A)R^B$,
(17) $SR^A$,
(18) $S(O)R^A$,
(19) $SO_2R^A$,
(20) $SO_2N(R^A)R^B$,
(21) $N(R^A)SO_2R^B$,
(22) $N(R^A)SO_2N(R^A)R^B$,
(23) $N(R^A)C(O)R^B$,
(24) $N(R^A)C(O)N(R^A)R^B$,
(25) $N(R^A)C(O)C(O)N(R^A)R^B$, or
(26) $N(R^A)C_2R^B$, and (ii) from zero to 2 substituents are each independently:
(1) CycD,
(2) AryD,
(3) HetD,
(4) HetZ,
(5) $C_{1-6}$ alkyl substituted with CycD, AryD, HetD, or HetZ, or
(6) C(O)-HetZ or C(O)C(O)-HetZ;

HetB independently has the same definition as HetA;
each HetC independently has the same definition as HetA;
HetP is (i) a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$ or (ii) a 6- to 10-membered saturated or mono-unsaturated, bridged or fused heterobicyclic ring containing from 1 to 4 heteroatoms independently selected from N, O and S, where each S is optionally oxidized to S(O) or $S(O)_2$; and wherein the saturated or mono-unsaturated heterocyclic or heterobicyclic ring is optionally substituted with a total of from 1 to 4 substituents, wherein:
(i) from zero to 4 substituents are each independently halogen, $C_{1-6}$ alkyl, haloalkyl, O—$C_{1-6}$ alkyl, O—$C_{1-6}$ haloalkyl, oxo, $C(O)N(R^A)R^B$, $C(O)C(O)N(R^A)R^B$, $C(O)R^A$ $CO_2R^A$, $SR^A$, $S(O)R^A$, $SO_2R^A$, or $SO_2N(R^A)R^B$, and
(ii) from zero to 2 substituents are each independently CycD, AryD, HetD, or $C_{1-6}$ alkyl substituted with CycD, AryD, HetD;

HetQ independently has the same definition as HetP;
each HetR independently has the same definition as HetP;
each CycD is independently a $C_{3-8}$ cycloalkyl which is optionally substituted with from 1 to 4 substituents each of which is independently halogen, $C_{1-6}$ alkyl, OH, O—$C_{1-6}$ alkyl, or $C_{1-6}$ haloalkyl;
each AryD is independently phenyl or naphthyl, wherein the phenyl or naphthyl is optionally substituted with from 1 to 5 substituents each of which is independently any one of the substituents (1) to (25) as set forth above in part (i) of the definition of AryA;
each HetD is independently a 5- or 6-membered heteroaromatic ring containing from 1 to 4 heteroatoms independently selected from N, O and S, wherein the heteroaromatic ring is optionally substituted with from 1 to 4 substituents each of which is independently any one of the substituents (1) to (26) as set forth above in part (i) of the definition of HetA;
each HetZ is independently a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$, wherein the saturated or mono-unsaturated heterocyclic ring is optionally substituted with from 1 to 4 substituents each of which is independently halogen, $C_{1-6}$ alkyl, $C_{1-6}$ haloalkyl, O—$C_{1-6}$ alkyl, O—$C_{1-6}$ haloalkyl, oxo, $C(O)N(R^A)R^B$) $C(O)C(O)N(R^A)R^B$, $C(O)R^A$, $CO_2R^A$, $SR^A$, $S(O)R^A$, $SO_2R^A$, or $SO_2N(R^A)R^B$;
each aryl is independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic; and
each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$.

The present invention also includes pharmaceutical compositions containing a compound of Formula I or a pharmaceutically acceptable salt thereof. The present invention further includes methods for the treatment of AIDS, the delay in the onset of AIDS, the prophylaxis of AIDS, the prophylaxis of infection by HIV, and tire treatment of infection by HIV.

Other embodiments, aspects and features of the present invention are either further described in or will be apparent from the ensuing description, examples and appended claims.

DETAILED DESCRIPTION OF THE INVENTION

The present invention includes compounds of Formula I above, and pharmaceutically acceptable salts thereof. These compounds and their pharmaceutically acceptable salts are HIV integrase inhibitors (e.g., HIV-1 integrase inhibitors).

A first embodiment of the present invention (alternatively referred to herein as "Embodiment E1") is a compound of Formula I, or a pharmaceutically acceptable salt thereof, wherein ring A is a 5- to 9-membered, saturated or mono-unsaturated heterocyclic ring containing in addition to the nitrogen shared with the naphthyridine ring from 1 to 3 heteroatoms independently selected from N, O, and S, and wherein each S is optionally oxidized to S(O) or S(O)$_2$; and wherein the saturated or mono-unsaturated heterocyclic ring is optionally substituted with a total of from 1 to 6 substituents, wherein:

(i) from zero to 6 substituents are each independently:
   (1) halogen,
   (2) $C_{1-6}$ alkyl,
   (3) $C_{1-6}$ haloalkyl,
   (4) $C_{1-6}$ alkyl substituted with OH, O—$C_{1-6}$ alkyl, O—$C_{1-6}$ haloalkyl, CN, $N(R^A)R^B$, $C(O)N(R^A)R^B$, $C(O)R^A$, $CO_2R^A$, C(O)—$N(R^A)$—$C_{1-6}$ alkylene-$OR^B$ with the proviso that the $N(R^A)$ moiety and the $OR^B$ moiety are not both attached to the same carbon of the $C_{1-6}$ alkylene moiety, $SR^A$, $S(O)R^A$, $SO_2R^A$, $SO_2N(R^A)R^B$, $N(R^A)C(O)R^B$, $N(R^A)C_2R^B$, $N(R^A)SO_2R^B$, $N(R^A)SO_2N(R^A)R^B$, $N(R^A)C(O)N(R^A)R^B$, or $OC(O)N(R^A)R^B$,
   (5) O—$C_{1-6}$ alkyl,
   (6) O—$C_{1-6}$ haloalkyl,
   (7) oxo,
   (8) =$C(R^A)R^B$,
   (9) $C(O)N(R^A)R^B$,
   (10) $C(O)C(O)N(R^A)R^B$,
   (11) $C(O)R^A$,
   (12) $CO_2R^A$,
   (13) $SR^A$,
   (14) $S(O)R^A$,
   (15) $SO_2R^A$, or
   (16) $SO_2N(R^A)R^B$, and (ii) from zero to 2 substituents are each Z—$R^L$ wherein:
   each Z is independently a single bond, $C_{1-6}$ alkylene, O, O—$C_{1-6}$ alkylene, $C_{1-6}$ alkylene-O, C(O), $C(O)C_{1-6}$ alkylene, $C_{1-6}$ alkylene-C(O), C(O)—$C_{1-6}$ alkylene-O, C(O)—$C_{1-6}$ alkylene-O—$C_{1-6}$ alkylene, $C(O)N(R^A)$, $C(O)N(R^A)$—$C_{1-6}$ alkylene, $C_{1-6}$ alkylene-$C(O)N(R^A)$, $C_{1-6}$ alkylene-$C(O)N(R^A)$—$C_{1-6}$ alkylene, S(O), $S(O)_2$, S(O)—$C_{1-6}$ alkylene, $S(O)_2$—$C_{1-6}$ alkylene, $C_{1-6}$ alkylene-S(O), or $C_{1-6}$ alkylene-$S(O)_2$; and
   each $R^L$ is independently CycC, AryC, HetC, or HetR;
and all other variables are as originally defined (i.e., as defined in the Summary of the Invention).

A second embodiment of the present invention (Embodiment E2) is a compound of Formula I, or a pharmaceutically acceptable salt thereof, wherein $R^1$ is $R^J$ or $C_{1-6}$ alkyl substituted with $R^J$; and all other variables are as originally defined or as defined in Embodiment E1.

A third embodiment of the present invention (Embodiment E3) is a compound of Formula I, or a pharmaceutically acceptable salt thereof, wherein $R^1$ is $C_{1-6}$ alkyl substituted with $R^J$; and all other variables are as originally defined or as defined in Embodiment E1.

A fourth embodiment of the present invention (Embodiment E4) is a compound of Formula I, or a pharmaceutically acceptable salt thereof, wherein $R^1$ is $C_{1-4}$ alkyl substituted with $R^J$; and all other variables are as originally defined or as defined in Embodiment E1.

A fifth embodiment of the present invention (Embodiment E5) is a compound of Formula I, or a pharmaceutically acceptable salt thereof, wherein $R^1$ is $(CH_2)_{1-2}R^J$; or $CH(CH_3)$—$R^J$; and all other variables are as originally defined or as defined in Embodiment E1.

A sixth embodiment of the present invention (Embodiment E6) is a compound of Formula I, or a pharmaceutically acceptable salt thereof, wherein $R^1$ is $CH_2$—$R^J$; and all other variables are as originally defined or as defined in Embodiment E1.

A seventh embodiment of the present invention (Embodiment E7) is a compound of Formula I, or a pharmaceutically acceptable salt thereof, wherein $R^J$ is AryA or HetA; and all other variables are as originally defined or as defined in any one of the preceding embodiments.

An eighth embodiment of the present invention (Embodiment E8) is a compound of Formula I, or a pharmaceutically acceptable salt thereof, wherein $R^J$ is phenyl, naphthyl, 2,3-dihydrobenzo-1,4-dioxinyl, benzol-1,3-dioxolyl, quinolinyl, isoquinolinyl, cinnolinyl, or quinazolinyl, any of which is optionally substituted with a total of from 1 to 4 substituents, wherein:

(a) from zero to 4 substituents are each independently:
   (1) $C_{1-6}$ alkyl,
   (2) O—$C_{1-6}$ alkyl,
   (3) $C_{1-6}$ haloalkyl,
   (4) O—$C_{1-6}$ haloalkyl,
   (5) OH,
   (6) halogen,
   (7) CN,
   (8) $N(R^A)R^B$,
   (9) $C(O)N(R^A)R^B$,
   (10) $S(O)R^A$,
   (11) $SO_2R^A$
   (12) $N(R^A)SO_2R^B$,
   (13) $N(R^A)SO_2N(R^A)R^B$,
   (14) $N(R^A)C(O)R^B$, or
   (15) $N(R^A)C(O)C(O)N(R^A)R^B$) and (b) from zero to 2 substituents are each independently HetZ or C(O)-HetZ,
   wherein HetZ is a 5- or 6-membered saturated heterocyclic ring containing a total of from 1 to 2 heteroatoms selected from 1 to 2 N atoms, zero to 1 O atom, and zero to 1 S atom, wherein the S atom is optionally S(O) or $SO_2$, wherein the saturated heterocyclic ring is optionally substituted with from 1 to 2 substituents each of which is $C_{1-4}$ alkyl, oxo, $C(O)N(R^A)R^B$, $C(O)R^A$, $CO_2R^A$, or $SO_2R^A$,
   and with the proviso that when HetZ is attached to the rest of the compound via the (O) moiety, then HetZ is attached to the (O) via a ring N atom;

and all other variables are as originally defined or as defined in any one of the preceding embodiments.

A ninth embodiment of the present invention (Embodiment E9) is a compound of Formula I, or a pharmaceutically acceptable salt thereof, wherein $R^1$ is $CH_2$—$R^J$; $R^J$ is as defined in Embodiment E8; and all other variables are as originally defined or as defined in Embodiment E1.

A tenth embodiment of the present invention (Embodiment E10) is a compound of Formula I, or a pharmaceutically acceptable salt thereof, wherein $R^1$ is:

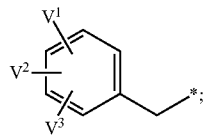

the asterisk * denotes the point of attachment of $R^1$ to the rest of the compound; $V^1$ and $V^2$ are each independently:
(1) H,
(2) $C_{1-4}$ alkyl,
(3) OH,
(4) O—$C_{1-4}$ alkyl,
(5) $C_{1-4}$ haloalkyl,
(6) O—$C_{1-4}$ haloalkyl,
(7) halogen,
(8) CN,
(9) $N(R^A)R^B$,
(10) $C(O)N(R^A)R^B$,
(11) $C(O)R^A$,
(12) $C(O)OR^A$,
(13) $SR^A$,
(14) $S(O)R^A$,
(15) $SO_2R^A$,
(16) $N(R^A)SO_2R^B$,
(17) $N(R^A)SO_2N(R^A)R^B$,
(18) $N(R^A)C(O)R^B$,
(19) $N(R^A)C(O)C(O)N(R^A)R^B$,
(20) HetD,
(21) HetZ, or
(22) C(O)-HetZ,
wherein
HetD is a 5- or 6-membered heteroaromatic ring containing a total of from 1 to 3 heteroatoms independently selected from 1 to 3 N atoms, from zero to 1 O atom, and from zero to 1 S atom, wherein the heteroaromatic ring is optionally substituted with 1 or 2 substituents each of which is independently $C_{1-4}$ alkyl, OH, O—$C_{1-4}$ alkyl, halogen, CN, C(O)$N(R^A)R^B$, $C(O)R^A$, $(CO)OR^A$, or $SO_2R^A$,
HetZ is a 5- or 6-membered saturated heterocyclic ring containing a total of from 1 to 2 heteroatoms selected from 1 to 2 N atoms, zero to 1 O atom, and zero to 1 S atom, wherein the S atom is optionally S(O) or $SO_2$, wherein the saturated heterocyclic ring is optionally substituted with from 1 to 2 substituents each of which is independently $C_{1-4}$ alkyl, oxo, $C(O)N(R^A)R^B$, $C(O)R^A$, $CO_2R^A$, or $SO_2R^A$,
and with the proviso that when HetZ is attached to the rest of the compound via the C(O) moiety, then HetZ is attached to the C(O) via a ring N atom;
or alternatively $V^1$ and $V^2$ are respectively located on adjacent carbons in the phenyl ring and together form methylenedioxy or ethylenedioxy; and
$V^3$ is:
(1) H,
(2) $C_{1-4}$ alkyl,
(3) O—$C_{1-4}$ alkyl,
(4) $C_{1-4}$ haloalkyl,
(5) O—$C_{1-4}$ haloalkyl, or
(6) halogen;
and all other variables are as originally defined or as defined in Embodiment E1.

An eleventh embodiment of the present invention (Embodiment E11) is a compound of Formula I, or a pharmaceutically acceptable salt thereof, wherein $R^1$ is $CH_2$—$R^J$; and $R^J$ is 4-fluorophenyl or 3-chloro-4-fluorophenyl; and all other variables are as originally defined or as defined in Embodiment E1.

A twelfth eleventh embodiment of the present invention (Embodiment E12) is a compound of Formula I, or a pharmaceutically acceptable salt thereof, wherein $R^2$ is H or $C_{1-6}$ alkyl; and $R^3$ is H, $C_{1-6}$ alkyl, $C(O)N(R^A)R^B$, $SO_2N(R^A)R^B$, or $C_{1-6}$ alkyl substituted with $C(O)N(R^A)R^B$ or $SO_2N(R^A)R^B$ and all other variables are as originally defined or as defined in any one of the preceding embodiments.

A thirteenth embodiment of the present invention (Embodiment E13) is a compound of Formula I, or a pharmaceutically acceptable salt thereof, wherein $R^2$ and $R^3$ are each independently H or $C_{1-4}$ alkyl; and all other variables are as originally defined or as defined in any one of the preceding embodiments.

A fourteenth embodiment of the present invention (Embodiment E14) is a compound of Formula I, or a pharmaceutically acceptable salt thereof, wherein $R^2$ and $R^3$ are both H; and all other variables are as originally defined or as defined in any one of the preceding embodiments.

A fifteenth embodiment of the present invention (Embodiment E15) is a compound of Formula I, or a pharmaceutically acceptable salt thereof, wherein ring A is:

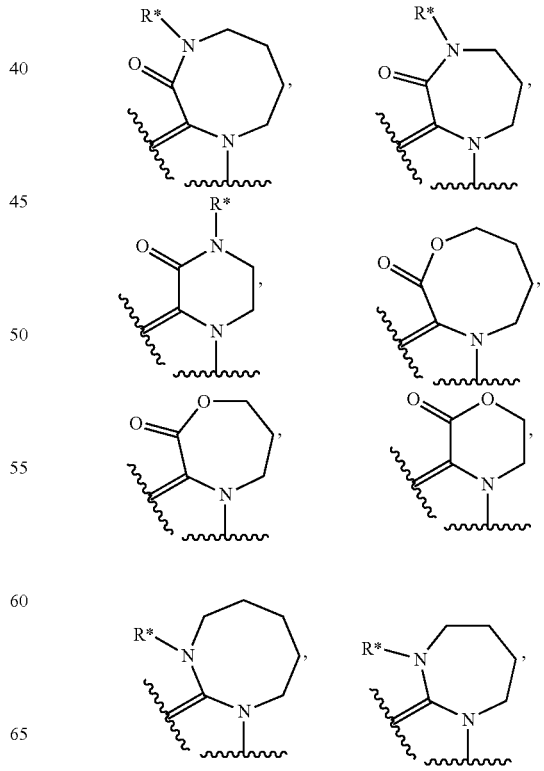

-continued

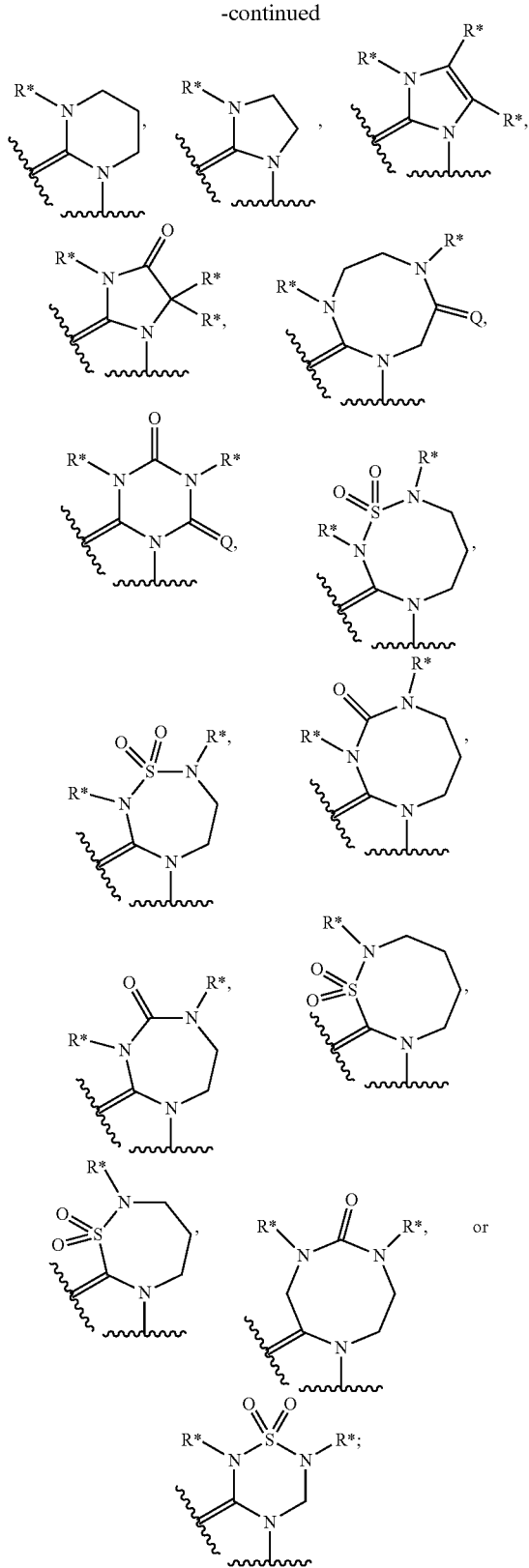

wherein each r* is independently: (1)H, (2), $C_{1-6}$ alkyl, (3) $C(O)R^A$, (4) $SO_2R^A$, (5) $CO_2R^A$, or (6) $C_{1-6}$ alkyl substituted with OH, O—$C_{1-6}$ alkyl, $N(R^A)R^B$, $C(O)N(R^A)R^B$, $C(O)R^A$, $CO_2R^A$, $C(O)N(R^A)$—$C_{1-6}$ alkylene-$OR^B$ with the proviso that the $N(R^A)$ moiety and the $OR^B$ moiety are not both attached to the same carbon of the $C_{1-6}$ alkylene moiety, $S(O)R^A$, $SO_2R^A$, $SO_2N(R^A)R^B$, $N(R^A)C(O)R^B$, $N(R^A)SO_2R^B$, or $OC(O)R^A$; Q is O or $C(R^A)R^B$; and the "⌇⌇⌇"*s denote the points at which ring A is attached to the remainder of the naphthyridine ring with which it is fused; and all other variables are as originally defined or as defined in any one of the preceding embodiments.

A sub-embodiment of Embodiment E15 is a compound of Formula I, or a pharmaceutically acceptable salt thereof, wherein each R* is independently: (1)H, (2), $C_{1-6}$ alkyl, (3) $C(O)R^A$, (4) $SO_2R^A$, or (5) $CO_2R^A$; and ring A, Q and all other variables are as defined in Embodiment E15.

A sixteenth embodiment of the present invention (Embodiment E16) is a compound of Formula I, or a pharmaceutically acceptable salt thereof, wherein each $R^A$ and $R^B$ is independently H or $C_{1-4}$ alkyl; and all other variables are as originally defined or as defined in any one of the preceding embodiments.

A seventeenth embodiment of the present invention (Embodiment E17) is a compound of Formula I, or a pharmaceutically acceptable salt thereof, wherein each $R^A$ and $R^B$ is independently H or $C_{1-3}$ alkyl; and all other variables are as originally defined or as defined in any one of the preceding embodiments.

An eighteenth embodiment of the present invention (Embodiment E18) is a compound of Formula I, or a pharmaceutically acceptable salt thereof, wherein each $R^A$ and $R^B$ is independently H or methyl; and all other variables are as originally defined or as defined in any one of the preceding embodiments.

A nineteenth embodiment of the present invention (Embodiment E19) is a compound of Formula I, or a pharmaceutically acceptable salt thereof, wherein bond "⋯a⋯" in the ring is a single bond; and all other variables are as originally defined or as defined in any one of the preceding embodiments.

A twentieth embodiment of the present invention (Embodiment E20) is a compound of Formula I, or a pharmaceutically acceptable salt thereof, wherein CycA, CycB, and CycC are each independently a $C_{3-7}$ cycloalkyl which is optionally substituted with from 1 to 2 substituents each of which is independently $C_{1-4}$ alkyl, O—$C_{1-4}$ alkyl, phenyl, or benzyl; and all other variables are as originally defined or as defined in any one of the preceding embodiments. In an aspect of this embodiment, CycA, CycB, and CycC are each independently cyclopropane, cyclobutane, cyclopentane, or cyclohexane, any of which is optionally substituted with methyl or phenyl; and all other variables are as originally defined or as defined in any one of the preceding embodiments.

A twenty-first embodiment of the present invention (Embodiment E21) is a compound of Formula I, or a pharmaceutically acceptable salt thereof, wherein each aryl (i.e., the aryl incorporated into the definitions of AryA, AryB, and AryC) is independently selected from the group consisting of phenyl, naphthyl, tetrahydronaphthyl(tetralinyl), indenyl, anthracenyl, or fluorenyl; and all other variables are as originally defined or as defined in any one of the preceding embodiments. In an aspect of this embodiment, each aryl is independently selected from the group consisting of phenyl and naphthyl. In another aspect of this embodiment, each aryl is phenyl.

A twenty-second embodiment of the present invention (Embodiment E22) is a compound of Formula I, or a pharmaceutically acceptable salt thereof, wherein each heteroaryl (i.e., the heteroaryl incorporated into the definitions of HetA, HetB, and HetC) is independently selected from the group consisting of pyrrolyl, pyrazolyl, thienyl, furanyl, imidazolyl, triazolyl, tetrazolyl, oxazolyl, isooxazolyl, oxadiazolyl, oxatriazolyl, thiazolyl, isothiazolyl, thiadiazolyl, pyridinyl (or pyridyl), pyrazinyl, pyrimidinyl, pyridazinyl, triazinyl, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, 2,3-dihydrobenzo-1,4-dioxinyl (i.e.,

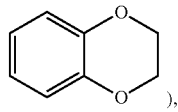

and benzo-1,3-dioxolyl (i.e.,

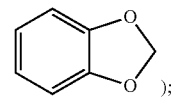

all other variables are as originally defined or as defined in any one of the preceding embodiments. In an aspect of this embodiment, each heteroaryl is independently a 5- or 6-membered heteroaromatic ring selected from the group consisting of pyrrolyl, pyrazolyl, thienyl, furanyl, imidazolyl, triazolyl, tetrazolyl, oxazolyl, isooxazolyl, oxadiazolyl, thiazolyl, isothiazolyl, thiadiazolyl, pyridinyl (or pyridyl), pyrazinyl, pyrimidinyl, and pyridazinyl.

A twenty-third embodiment of the present invention (Embodiment E23) is a compound of Formula I, or a pharmaceutically acceptable salt thereof, wherein HetP and HetQ are each independently a 4- to 7-membered, saturated heterocyclic ring containing from 1 to 3 heteroatoms independently selected from N, O and S, where each S is optionally oxidized to S(O) or $SO_2$; wherein the heterocyclic ring is optionally substituted with from 1 to 4 substituents each of which is independently halogen, $C_{1-4}$ alkyl, $C_{1-4}$ haloalkyl, O—$C_{1-4}$ alkyl, O—$C_{1-4}$ haloalkyl, oxo, C(O)N($R^A$)$R^B$, C(O)C(O)N($R^A$)$R^B$, C(O)$R^A$, $CO_2R^A$, $SR^A$, S(O)$R^A$, $SO_2R^A$, or $SO_2N(R^A)R^B$; and all other variables are as originally defined or as defined in any one of the preceding embodiments. In an aspect of this embodiment, HetP and HetQ are each independently selected from the group consisting of azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl.

A twenty-fourth embodiment of the present invention (Embodiment E24) is a compound of Formula I, or a pharmaceutically acceptable salt thereof, wherein each CycD is independently a $C_{3-7}$ cycloalkyl which is optionally substituted with from 1 to 2 substituents each of which is independently $C_{1-4}$alkyl, O—$C_{1-4}$ alkyl, phenyl, or benzyl. In an aspect of this embodiment, each CycD is independently cyclopropane, cyclobutane, cyclopentane, or cyclohexane, any of which is optionally substituted with methyl or phenyl; and all other variables are as originally defined or as defined in any one of the preceding embodiments.

A twenty-fifth embodiment of the present invention (Embodiment E25) is a compound of Formula I, or a pharmaceutically acceptable salt thereof, wherein each AryD is independently phenyl which is optionally substituted with from 1 to 3 substituents each of which is independently (1) $C_{1-4}$ alkyl, (2) OH, (3) O—$C_{1-4}$ alkyl, (4) $C_{1-4}$ haloalkyl, (5) O—$C_{1-4}$ haloalkyl, (6) halogen, (7) CN, (8) N($R^A$)$R^B$, (9) C(O)N($R^A$)$R^B$, (10) C(O)$R^A$, (11) C(O)O$R^A$ (12) $SR^A$, (13) S(O)$R^A$, (14) $SO_2R^A$, (15) N($R^A$)$SO_2R^B$, (16) N($R^A$)$SO_2$N($R^A$)$R^B$, (17) N($R^A$)C(O)$R^B$, or (18) N($R^A$)C(O)C(O)N($R^A$)$R^B$; and all other variables are as originally defined or as defined in any one of the preceding embodiments.

A twenty-sixth embodiment of the present invention (Embodiment E26) is a compound of Formula I, or a pharmaceutically acceptable salt thereof, wherein each AryD is independently phenyl which is optionally substituted with from 1 to 3 substituents each of which is independently (1) $C_{1-4}$ alkyl, (2) $C_{1-4}$ haloalkyl, (3) OH, (4) O—$C_{1-4}$ alkyl, (5) halogen, (6) CN, (7) C(O)$NH_2$, (8) C(O)NH($C_{1-4}$ alkyl), (9) C(O)N($C_{1-4}$ alkyl)$_2$, or (10) $SO_2$—$C_{1-4}$ alkyl; and all other variables are as originally defined or as defined in any one of the preceding embodiments, hi an aspect of this embodiment, the 1 to 3 substituents are each independently selected from the group consisting of $CH_3$, $CF_3$, OH, $OCH_3$, Cl, Br, F, CN, C(O)$NH_2$, C(O)NH($CH_3$), C(O)N($CH_3$)$_2$, or $SO_2CH_3$.

A twenty-seventh embodiment of the present invention (Embodiment E27) is a compound of Formula I, or a pharmaceutically acceptable salt thereof, wherein each HetD is independently a 5- or 6-membered heteroaromatic ring independently selected from the group consisting of pyrrolyl, pyrazolyl, thienyl, furanyl, imidazolyl, triazolyl, tetrazolyl, oxazolyl, isooxazolyl, oxadiazolyl, oxatriazolyl, thiazolyl, isothiazolyl, thiadiazolyl, pyridinyl (or pyridyl), pyrazinyl, pyrimidinyl, pyridazinyl, and triazinyl; wherein the heteroaromatic ring is optionally substituted with from 1 to 3 substituents each of which is independently (1) $C_{1-4}$ alkyl, (2) OH, (3) O—$C_{1-4}$ alkyl, (4) $C_{1-4}$ haloalkyl, (5) O—$C_{1-4}$ haloalkyl, (6) halogen, (7) CN, (8) N($R^A$)$R^B$, (9) C(O)N($R^A$)$R^B$, (10) C(O)$R^A$, (11) C(O)O$R^A$, (12) $SR^A$, (13) S(O)$R^A$, (14) $SO_2R^A$, (15)N($R^A$)$SO_2R^B$, (16) N($R^A$)$SO_2$N($R^A$)$R^B$, (17) N($R^A$)C(O)$R^B$, or (18) N($R^A$)C(O)C(O)N($R^A$)$R^B$; and all other variables are as originally defined or as defined in any one of the preceding embodiments.

A twenty-eighth embodiment of the present invention (Embodiment E28) is a compound of Formula I, or a pharmaceutically acceptable salt thereof, wherein each HetD is independently a 5- or 6-membered heteroaromatic ring independently selected from the group consisting of the heteroaromatic rings set forth in Embodiment E27, wherein the heteroaromatic ring is optionally substituted with from 1 to 3 substituents each of which is independently (1) $C_{1-4}$ alkyl, (2) $C_{1-4}$ haloalkyl, (3) OH, (4) O—$C_{1-4}$ alkyl, (5) halogen, (6) CN, (7) C(O)$NH_2$, (8) C(O)NH($C_{1-4}$ alkyl), (9) C(O)N($C_{1-4}$ alkyl)$_2$, or (10) $SO_2$—$C_{1-4}$ alkyl; and all other variables are as originally defined or as defined in any one of the preceding embodiments. In an aspect of this embodiment, the 1 to 3 substituents are each independently selected from the group consisting of $CH_3$, $CF_3$, OH, $OCH_3$, Cl, Br, F, CN, C(O)$NH_2$, C(O)NH($CH_3$), C(O)N($CH_3$)$_2$, or $SO_2CH_3$.

A twenty-ninth embodiment of the present invention (Embodiment E29) is a compound of Formula I, or a pharmaceutically acceptable salt thereof, wherein each HetD is independently a 5- or 6-membered heteroaromatic ring containing a total of from 1 to 3 heteroatoms independently selected from 1 to 3 N atoms, from zero to 1O atom, and from zero to 1 S atom, wherein the heteroaromatic ring is optionally substituted with 1 or 2 substituents each of which is independently $C_{1-4}$ alkyl, OH, O—$C_{1-4}$ alkyl, halogen, CN, C(O)N($R^A$)$R^B$, C(O)R$^A$, C(O)OR$^A$, or SO$_2$R$^A$; and all other variables are as originally defined or as defined in any one of the preceding embodiments.

A thirtieth embodiment of the present invention (Embodiment E30) is a compound of Formula I, or a pharmaceutically acceptable salt thereof, wherein each HetZ is independently a 4- to 7-membered, saturated heterocyclic ring containing from 1 to 3 heteroatoms independently selected from N, O and S, where each S is optionally oxidized to S(O) or SO$_2$; wherein the heterocyclic ring is optionally substituted with from 1 to 4 substituents each of which is independently halogen, C$_{1-4}$ alkyl, C$_{1-4}$ haloalkyl, O—C$_{1-4}$ alkyl, O—C$_{1-4}$ haloalkyl, oxo, C(O)N(R$^A$)R$^B$, C(O)C(O)N(R$^A$)R$^B$, C(O)R$^A$ CO$_2$R$^A$, SR$^A$, S(O)R$^A$, SO$_2$R$^A$, or SO$_2$N(R$^A$)R$^B$; and all other variables are as originally defined or as defined in any one of the preceding embodiments. In an aspect of this embodiment, each HetZ is independently a saturated heterocyclic ring selected from the group consisting of azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl, wherein the ring is optionally substituted with from 1 to 2 substituents each of which is independently C$_{1-4}$ alkyl or oxo.

A thirty-first embodiment of the present invention (Embodiment E31) is a compound of Formula I, or a pharmaceutically acceptable salt thereof, wherein Y is a single bond, (CH$_2$)$_{1-2}$, O, O—(CH$_2$)$_{1-2}$, (CH$_2$)$_{1-2}$—O, C(O), C(O)—(CH$_2$)$_{1-2}$, (CH$_2$)$_{1-2}$—C(O), C(O)(CH$_2$)$_{1-2}$—O, C(O)—(CH$_2$)$_{1-2}$—O—(CH$_2$)$_{1-2}$, C(O)N(R$^A$), C(O)N(R$^A$)—(CH$_2$)$_{1-2}$, (CH$_2$)$_{1-2}$—C(O)N(R$^A$), (CH$_2$)$_{1-2}$—C(O)N(R$^A$)—(CH$_2$)$_{1-2}$, S(O), S(O)$_2$, S(O)—(CH$_2$)$_{1-2}$, S(O)$_2$(CH$_2$)$_{1-2}$, (CH$_2$)$_{1-2}$—S(O), or (CH$_2$)$_{1-2}$—S(O)$_2$; and all other variables are as originally defined or as defined in any one of the preceding embodiments.

A thirty-second embodiment of the present invention (Embodiment E32) is a compound of Formula I, or a pharmaceutically acceptable salt thereof, wherein each Z is independently a single bond, (CH$_2$)$_{1-2}$, O, O—(CH$_2$)$_{1-2}$, (CH$_2$)$_{1-2}$—O, C(O), C(O)—(CH$_2$)$_{1-2}$, (CH$_2$)$_{1-2}$—C(O), C(O)—(CH$_2$)$_{1-2}$—O, C(O)—(CH$_2$)$_{1-2}$—O—(CH$_2$)$_{1-2}$, C(O)N(R$^A$), C(O)N(R$^A$)—(CH$_2$)$_{1-2}$, (CH$_2$)$_{1-2}$—C(O)N(R$^A$), (CH$_2$)$_{1-2}$—C(O)N(R$^A$)—(CH$_2$)$_{1-2}$, S(O), S(O)$_2$, S(O)—(CH$_2$)$_{1-2}$, S(O)$_2$—(CH$_2$)$_{1-2}$, (CH$_2$)$_{1-2}$—S(O), or (CH$_2$)$_{1-2}$—S(O)$_2$; and all other variables are as originally defined or as defined in any one of the preceding embodiments.

A first class of the present invention (alternatively referred to herein as "Class C1") includes compounds of Formula IIa and IIb and pharmaceutically acceptable salts thereof:

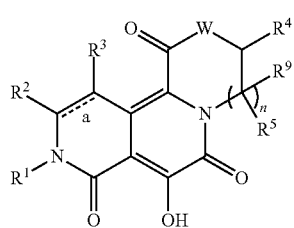

(IIa)

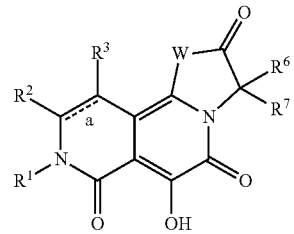

(IIb)

wherein:

bond "a" in the ring is a single bond or a double bond;

R$^1$, R$^2$ and R$^3$ are each as originally defined above or as defined in any one of the preceding embodiments;

n is an integer equal to zero, 1, 2, or 3;

W is O or N—R$^8$;

R$^4$ is:
(1) H,
(2) C$_{1-6}$ alkyl, or
(3) C$_{1-6}$ alkyl substituted with OH or OC(O)R$^A$;

each R$^5$ is independently:
(1) H,
(2) C$_{1-6}$ alkyl,
(3) C$_{1-6}$ alkyl substituted with OH,
(4) OH, or
(5) —R$^L$;

each R$^9$ is independently H or C$_{1-6}$ alkyl;

alternatively, R$^5$ and R$^9$ attached to the same ring carbon atom together form oxo or =C(R$^A$)R$^B$;

R$^6$ and R$^7$ are each independently H, C$_{1-6}$ alkyl, or C$_{1-6}$ alkyl substituted with OH; and R$^8$ is:
(1) H,
(2) C$_{1-6}$ alkyl,
(3) C$_{1-6}$ haloalkyl,
(4) C$_{1-6}$ alkyl substituted with OH, O—C$_{1-6}$ alkyl, N(R$^A$)R$^B$, C(O)N(R$^A$)R$^B$, C(O)R$^A$ CO$_2$R$^A$, C(O)—N(R$^A$)—C$_{1-6}$ alkylene-OR$^B$ with the proviso that the N(R$^A$) moiety and the OR$^B$ moiety are not both attached to the same carbon of the C$_{1-6}$ alkylene moiety, S(O)R$^A$, SO$_2$R$^A$, SO$_2$N(R$^A$)R$^B$, N(R$^A$)C(O)R$^B$, N(R$^A$)SO$_2$R$^B$, or OC(O)R$^A$, or
(5) Z—R$^L$;

wherein R$^A$, R$^B$, Z and R$^L$ are each as originally defined above.

It is understood that n=0 means a 5-membered ring with a direct bond between the ring N atom shared with the naphthyridine ring and the ring carbon to which R$^4$ is attached A subclass of the first class (alternatively referred to as "Subclass SC1-1") includes compounds of Formula IIa and IIb, and pharmaceutically acceptable salts thereof, wherein R$^1$ is as defined in Embodiment E10; and all other variables are as originally defined Class C1.

A second class of the present invention (Class C2) includes compounds of Formula IIa' and IIb' and pharmaceutically acceptable salts thereof:

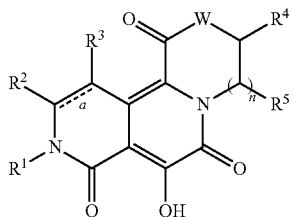
(IIa')

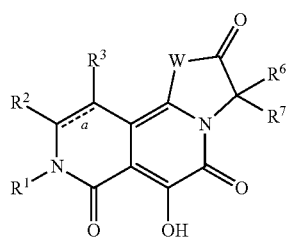
(IIb')

wherein:
$R^4$ is H or $C_{1-6}$ alkyl;
each $R^5$ is independently H or $C_{1-6}$ alkyl;
$R^6$ and $R^7$ are each independently H or $C_{1-6}$ alkyl; and
$R^8$ is:
(1) H,
(2) $C_{1-6}$ alkyl,
(3) $C_{1-6}$ haloalkyl,
(4) $C_{1-6}$ alkyl substituted with $C(O)N(R^A)R^B$, $C(O)R^A$, $CO_2R^A$, $C(O)$—$N(R^A)$—$C_{1-6}$ alkylene-$OR^B$ with the proviso that the $N(R^A)$ moiety and the $OR^B$ moiety are not both attached to the same carbon of the $C_{1-6}$ alkylene moiety, $S(O)R^A$, $SO_2R^A$, or $SO_2N(R^A)R^B$, or
(5) Z—$R^L$;
and all other variables are as originally defined in Class C1.

A subclass of the second class (Subclass SC2-1) includes compounds of Formula IIa' and IIb', and pharmaceutically acceptable salts thereof, wherein W is O, NH, or N—$C_{1-6}$ alkyl; and all other variables are as originally defined in the second class.

Another subclass of the second class (Subclass SC2-2) includes compounds of Formula IIa' and IIb', and pharmaceutically acceptable salts thereof, wherein W is O, NH, or N—$C_{1-4}$ alkyl; and all other variables are as originally defined in the second class.

Another subclass of the second class (Subclass SC2-3) includes compounds of Formula IIa' and IIb', and pharmaceutically acceptable salts thereof, wherein W is O; and all other variables are as originally defined in the second class.

Still another subclass of the second class (Subclass SC2-4) includes compounds of Formula IIa' and IIb', and pharmaceutically acceptable salts thereof, wherein W is NH or N—$C_{1-4}$ alkyl; and all other variables are as originally defined in the second class.

Still another subclass of the second class (Subclass SC2-5) includes compounds of Formula IIa' and IIb', and pharmaceutically acceptable salts thereof, wherein W is NH or N—$C_{1-3}$ alkyl; and all other variables are as originally defined in the second class.

Still another subclass of the second class (Subclass SC2-6) includes compounds of Formula IIa' and IIb', and pharmaceutically acceptable salts thereof, wherein W is NH or N—$CH_3$; and all other variables are as originally defined in the second class.

Still another subclass of the second class (Subclass SC2-7) includes compounds of Formula IIa' and IIb', and pharmaceutically acceptable salts thereof, wherein Z is a single bond, $(CH_2)_{1-2}$, O, O—$(CH_2)_{1-2}$, $(CH_2)_{1-2}$—O, C(O), C(O)—$(CH_2)_{1-2}$, $(CH_2)_{1-2}$—C(O), C(O)—$(CH_2)_{1-2}$—O, C(O)—$(CH_2)_{1-2}$—O—$(CH_2)_{1-2}$, $C(O)N(R^A)$, $C(O)N(R^A(CH_2)_{1-2}$, $(CH_2)_{1-2}$—$C(O)N(R^A)$, $(CH_2)_{1-2}$—$C(O)N(R^A)$—$(CH_2)_{1-2}$, S(O), $S(O)_2$, S(O)—$(CH_2)_{1-2}$, $S(O)_2$—$(CH_2)_{1-2}$, $(CH_2)_{1-2}$—S(O), or $(CH_2)_{1-2}$—$S(O)_2$; and all other variables are as originally defined in the second class or as defined in any of the preceding subclasses of the second class.

A third class of the present invention (Class C3) includes compounds of Formula IIa, IIb, IIc, and IId and pharmaceutically acceptable salts thereof:

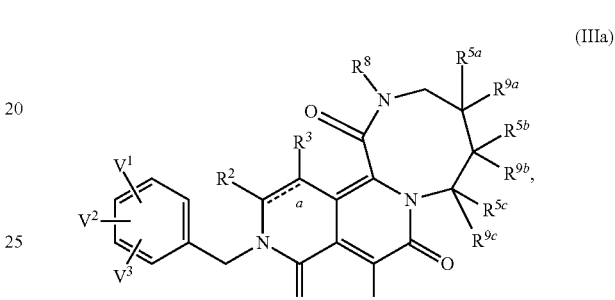
(IIIa)

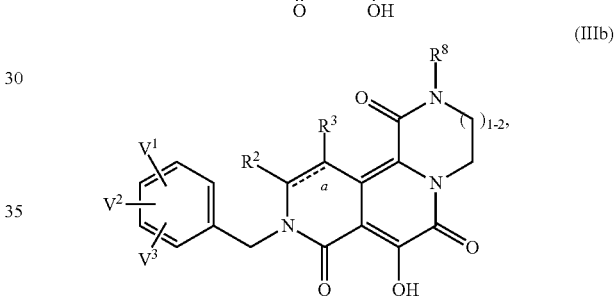
(IIIb)

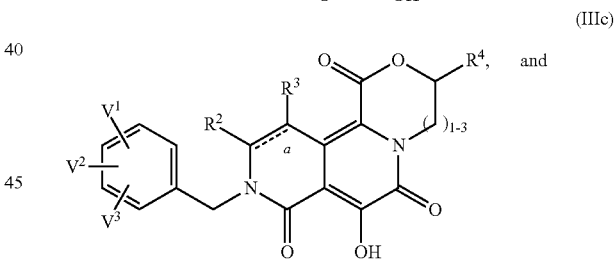
(IIIc)

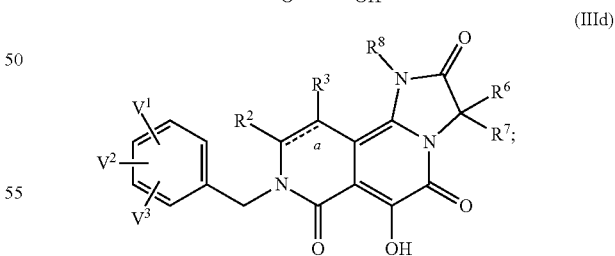
(IIId)

wherein:
bond "$\underset{a}{\text{---}}$" in the ring is a single bond or a double bond;
$R^2$ and $R^3$ are each independently H or $C_{1-4}$ alkyl;
$R^4$ is:
(1) H,
(2) $C_{1-4}$ alkyl, or
(3) $C_{1-4}$ alkyl substituted with OH or $OC(O)R^A$;
$R^{5a}$ is H, $C_{1-4}$ alkyl, OH or –HetR;

$R^{9a}$ is H or $C_{1-4}$ alkyl;

alternatively, $R^{5a}$ and $R^{9a}$ together form oxo;

$R^{5b}$ is H, $C_{1-4}$ alkyl, or OH;

$R^{9b}$ is H or $C_{1-4}$ alkyl;

$R^{5c}$ is H, $C_{1-4}$ alkyl, or $C_{1-4}$ alkyl substituted with OH;

$R^{9c}$ is h or $C_{1-4}$ alkyl;

alternatively, $R^{5c}$ and $R^{9c}$ together form $=CH_2$;

with the proviso that when one of $R^{5a}$, $R^{5b}$ and $R^{5c}$ is other than H or $C_{1-4}$ alkyl, then the other two of $R^{5a}$, $R^{5b}$ and $R^{5c}$ is H or $C_{1-4}$ alkyl;

one of $R^6$ and $R^7$ is H, $C_{1-4}$ alkyl, or $C_{1-4}$ alkyl substituted with OH, and the other of $R^6$ and $R^7$ is H or $C_{1-4}$ alkyl;

$R^8$ is:

(1) H, (2) $C_{1-4}$ alkyl, (3) $C_{1-4}$ haloalkyl, (4) $C_{1-4}$ alkyl substituted with OH, O—$C_{1-4}$ alkyl, $N(R^A)R^B$, $C(O)N(R^A)R^B$, $C(O)R^A$, $CO_2R^A$, $S(O)R^A$, $SO_2R^A$, $SO_2N(R^A)R^B$, $N(R^A)C(O)R^B$, $N(R^A)SO_2R^B$, or $OC(O)R^A$, (5) $C_{1-4}$ alkylene-HetC, or (6) $C_{1-4}$ alkylene-HetR;

HetC is a 5- or 6-membered heteroaromatic ring containing a total of from 1 to 3 heteroatoms independently selected from 1 to 3 N atoms, from zero to 1O atom, and from zero to 1 S atom, wherein the heteroaromatic ring is optionally substituted with 1 or 2 substituents each of which is independently $C_{1-4}$ alkyl, OH, O—$C_{1-4}$ alkyl, halogen, CN, $C(O)N(R^A)R^B$, $C(O)R^A$, $C(O)OR^A$ or $SO_2R^A$;

HetR is a 5- or 6-membered saturated heterocyclic ring containing a total of from 1 to 2 heteroatoms selected from 1 to 2 N atoms, zero to 1O atom, and zero to 1 S atom, wherein the S atom is optionally S(O) or $SO_2$, wherein the saturated heterocyclic ring is optionally substituted with from 1 to 2 substituents each of which is independently $C_{1-4}$ alkyl, oxo, $C(O)N(R^A)R^B$, $C(O)R^A$, $CO_2R^A$, or $SO_2R^A$;

each $R^A$ is independently H or $C_{1-4}$ alkyl;

each $R^B$ is independently H or $C_{1-4}$ alkyl; and $V^1$, $V^2$ and $V^3$ are as defined in Embodiment E10.

As an example of the proviso for $R^{5a}$, $R^{5b}$ and $R^{5c}$ in Class C3, when $R^{5a}$ is OH or –HetR or when $R^{5a}$ and $R^{9a}$ together form oxo, then $R^{5b}$ and $R^{5c}$ are each independently H or $C_{1-4}$ alkyl.

A fourth class of the present invention (Class C4) includes compounds of Formula IIIa' and IIId' and pharmaceutically acceptable salts thereof:

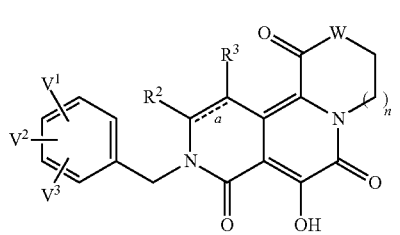

(IIIa')

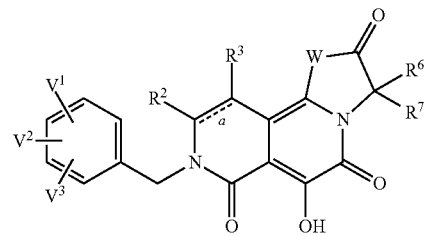

(IIId')

wherein:

bond "--a--" in the ring is a single bond or a double bond;

n is an integer equal to zero, 1, 2 or 3;

$V^1$ and $V^2$ are each independently:

(1) H,
(2) $C_{1-4}$ alkyl
(3) OH,
(4) O—$C_{1-4}$ alkyl,
(5) $C_{1-4}$ haloalkyl,
(6) O—$C_{1-4}$ haloalkyl,
(7) halogen,
(8) CN,
(9) $N(R^A)R^B$,
(10) $C(O)N(R^A)R^B$,
(11) $C(O)R^A$,
(12) $C(O)OR^A$,
(13) $SR^A$,
(14) $S(O)R^A$,
(15) $SO_2R^A$,
(16) $N(R^A)SO_2R^B$,
(17) $N(R^A)SO_2N(R^A)R^B$,
(18) $N(R^A)C(O)R^B$,
(19) $N(R^A)C(O)C(O)N(R^A)R^B$,
(20) HetD,
(21) HetZ, or
(22) C(O)-HetZ,
wherein HetD is a 5- or 6-membered heteroaromatic ring containing a total of from 1 to 3 heteroatoms independently selected from 1 to 3 N atoms, from zero to 1O atom, and from zero to 1 S atom, wherein the heteroaromatic ring is optionally substituted with 1 or 2 substituents each of which is independently $C_{1-4}$ alkyl, OH, O—$C_{1-4}$ alkyl, halogen, CN, $C(O)N(R^A)R^B$, $C(O)R^A$, $C(O)OR^A$, or $SO_2R^A$ HetZ is a 5- or 6-membered saturated heterocyclic ring containing a total of from 1 to 2 heteroatoms selected from 1 to 2 N atoms, zero to 1O atom, and zero to 1 S atom, wherein the S atom is optionally S(O) or $SO_2$, wherein the saturated heterocyclic ring is optionally substituted with from 1 to 2 substituents each of which is independently $C_{1-4}$ alkyl, oxo, $C(O)N(R^A)R^B$, $C(O)R^A$, $CO_2R^A$, or $SO_2R^A$ and with the proviso that when HetZ is attached to the rest of the compound via the C(O) moiety, then HetZ is attached to the C(O) via a ring N atom;

or alternatively $V^1$ and $V^2$ are respectively located on adjacent carbons in the phenyl ring and together form methylenedioxy or ethylenedioxy;

$V^3$ is:

(1) H,
(2) $C_{1-4}$ alkyl,
(3) O—$C_{1-4}$ alkyl,
(4) $C_{1-4}$ haloalkyl,
(5) O—$C_{1-4}$ haloalkyl, or
(6) halogen;

W is O, NH, N—C$_{1-4}$ alkyl, NC(O)—C$_{1-4}$ alkyl, N—C(O)O—C$_{1-4}$ alkyl, or N—SO$_2$—C$_{1-4}$ alkyl;
R$^2$ and R$^3$ are each independently H or C$_{1-4}$ alkyl;
R$^6$ and R$^7$ are each independently H or C$_{1-4}$ alkyl;
each R$^A$ is independently H or C$_{1-4}$ alkyl; and
each R$^B$ is independently H or C$_{1-4}$ alkyl.

A subclass of the fourth class (Subclass SC4-1) includes compounds of Formula IIIa' and IIId', and pharmaceutically acceptable salts thereof, wherein:

bond "╌ᵃ╌" in the ring is a single bond;
n is an integer equal to 1, 2 or 3;
V$^1$ and V$^2$ are each independently:
  (1) H,
  (2) C$_{1-4}$ alkyl,
  (3) C$_{1-4}$ haloalkyl,
  (4) OH,
  (5) O—C$_{1-4}$ alkyl,
  (6) halogen,
  (7) CN,
  (8) C(O)NH$_2$,
  (9) C(O)NH(C$_{1-4}$ alkyl),
  (10) C(O)N(C$_{1-4}$ alkyl)$_2$, or
  (11) SO$_2$—C$_{1-4}$ alkyl;
or alternatively V$^1$ and V$^2$ are respectively located on adjacent carbons in the phenyl ring and together form methylenedioxy or ethylenedioxy; and
V$^3$ is H, halogen, C$_{1-4}$ alkyl, or O—C$_{1-4}$ alkyl;
and all other variables are as originally defined in the Class C4.

A fifth class of the present invention (Class C5) includes compounds of Formula IIIa' and IIId' and pharmaceutically acceptable salts thereof wherein:

bond "╌ᵃ╌" in the ring is a single bond;
n is an integer equal to 1, 2 or 3;
V$^1$ and are each independently:
  (1) H,
  (2) CH$_3$,
  (3) CF$_3$,
  (4) OH,
  (5) OCH$_3$,
  (6) Cl, Br, or F,
  (7) CN,
  (8) C(O)NH$_2$,
  (9) C(O)NH(CH$_3$),
  (10) C(O)N(CH$_3$)$_2$, or
  (11) SO$_2$CH$_3$;
V$^3$ is H, Cl, Br, F, CH$_3$, or OCH$_3$;
W is O, NH, or N—CH$_3$;
R$^2$ and R$^3$ are both H; and
R$^6$ and R$^7$ are each independently H or CH$_3$.

A sixth class of the present invention (Class C6) includes compounds of Formula IIIa, IIb, IIIc and IIId and pharmaceutically acceptable salts thereof, wherein:

bond "╌ᵃ╌" in the ring is a single bond;
R$^2$ and R$^3$ are each independently H or CH$_3$;
R$^4$ is:
  (1) H
  (2) CH$_3$,
  (3) CH$_2$CH$_3$,
  (4) CH$_2$CH$_2$CH$_3$,
  (5) CH(CH$_3$)$_2$,
  (3) (CH$_2$)$_{1-3}$—OH, or
  (4) (CH$_2$)$_{1-3}$—OC(O)R$^A$;
R$^{5a}$ is H, CH$_3$, CH$_2$CH$_3$, CH$_2$CH$_2$CH$_3$, CH(CH$_3$)$_2$, OH or –HetR;

R$^{9a}$ is H, CH$_3$, CH$_2$CH$_3$, CH$_2$CH$_2$CH$_3$, or CH(CH$_3$)$_2$;
alternatively, R$^{5a}$ and R$^{9a}$ together form oxo;
R$^{5b}$ is H, CH$_3$, CH$_2$CH$_3$, CH$_2$CH$_2$CH$_3$, CH(CH$_3$)$_2$, or OH;
R$^{9b}$ H, CH$_3$, CH$_2$CH$_3$, CH$_2$CH$_2$CH$_3$, or CH(CH$_3$)$_2$;
R$^{5c}$ is H, CH$_3$, CH$_2$CH$_3$, CH$_2$CH$_2$CH$_3$, CH(CH$_3$)$_2$, or (CH$_2$)$_{1-3}$—OH;
R$^{9c}$ is H, CH$_3$, CH$_2$CH$_3$, CH$_2$CH$_2$CH$_3$, or CH(CH$_3$)$_2$;
alternatively, R$^{5c}$ and R$^{9c}$ together form =CH$_2$;
with the proviso that when one of R$^{5a}$, R$^{5b}$ and R$^{5c}$ is other than H, CH$_3$, CH$_2$CH$_3$, CH$_2$CH$_2$CH$_3$, or CH(CH$_3$)$_2$, then the other two of R$^{5a}$, R$^{5b}$ and R$^{5c}$ is H, CH$_3$, CH$_2$CH$_3$, CH$_2$CH$_2$CH$_3$, or CH(CH$_3$)$_2$;
one of R$^6$ and R$^7$ is H, CH$_3$, CH$_2$CH$_3$, CH$_2$CH$_2$CH$_3$, CH(CH$_{32}$ or (CH$_2$)$_{1-3}$—OH, and the other of R$^6$ and R$^7$ is H or CH$_3$;
R$^8$ is:
  (1) H,
  (2) CH$_3$,
  (3) CH$_2$CH$_3$,
  (4) CH$_2$CH$_2$CH$_3$,
  (5) CH(CH$_3$)$_2$,
  (6) CH$_2$CH$_2$CH$_2$CH$_3$,
  (7) (CH$_3$)$_3$,
  (8) CH$_2$CH(CH$_3$)$_2$,
  (9) CH(CH$_3$)CH$_2$CH$_3$,
  (10) CF$_3$,
  (11) CH$_2$CF$_3$,
  (12) (CH$_2$)$_{2-4}$—U, wherein U is OH, OCH$_3$, N(R$^A$)R$^B$; N(R$^A$)C(O)R$^B$, N(R$^A$)SO$_2$R$^B$, or OC(O)R$^A$
  (13) (CH$_2$)$_{1-4}$—V, wherein V is C(O)N(R$^A$)R$^B$, C(O)R$^A$, CO$_2$R$^A$, S(O)R$^A$, SO$_2$R$^A$ or SO$_2$N(R$^A$)R$^B$,
  (14) (CH$_2$)$_{2-4}$-HetC, or
  (15) (CH$_2$)$_{2-4}$-HetR;
HetC is a 5-membered heteroaromatic ring selected from the group consisting of:

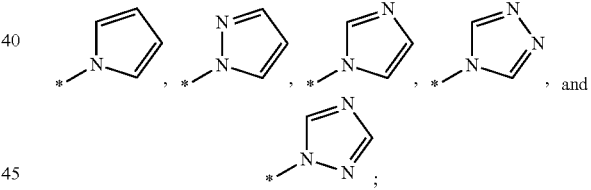

HetR is a 5- or 6-membered saturated heterocyclic ring selected from the group consisting of:

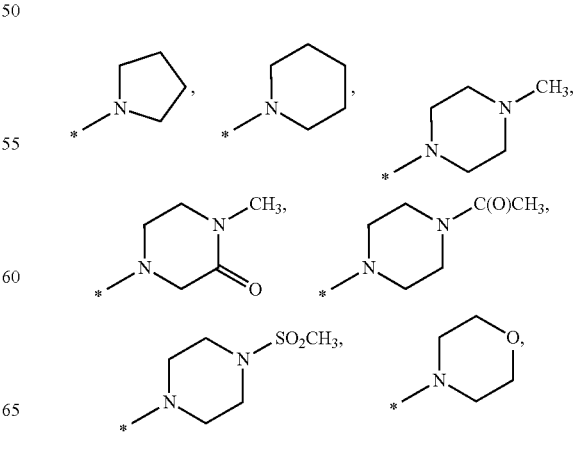

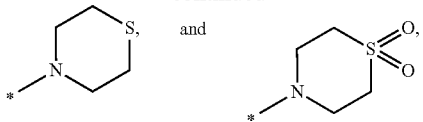

the asterisk * in HetC and HetR denotes the point of attachment to the rest of the molecule;
each $R^A$ is independently H or $CH_3$;
each $R^B$ is independently H or $CH_3$;
$V^1$ and $V^2$ are each independently:
 (1) H,
 (2) $CH_3$,
 (3) $CF_3$,
 (4) OH,
 (5) $OCH_3$,
 (6) Cl, Br, or F,
 (7) CN,
 (8) $C(O)NH_2$,
 (9) $C(O)NH(CH_3)$,
 (10) $(O)N(CH_3)_2$, or
 (11) $SO_2CH_3$; and
$V^3$ is H, Cl, Br, F, $CH_3$, or $OCH_3$.

Another embodiment of the present invention is a compound, or a pharmaceutically acceptable salt thereof, selected from the group consisting of the compounds set forth in Examples 1 to 64. Another embodiment of the present invention is a compound, or a pharmaceutically acceptable salt thereof, selected from the group consisting of the compounds set forth in Examples 1 to 9. Another embodiment of the present invention is a compound, or a pharmaceutically acceptable salt thereof, selected from the group consisting of the compounds set forth in Examples 10 to 64.

Another embodiment of the present invention is a compound of Formula I, or a pharmaceutically acceptable salt thereof, as originally defined or as defined in any of the foregoing embodiments, classes, subclasses, aspects, or features, wherein the compound or its salt is substantially pure. As used herein "substantially pure" means that the compound or its salt is present (e.g., in a product isolated from a chemical reaction or a metabolic process) in an amount of at least about 90 wt. % (e.g., from about 95 wt. % to 100 wt. %), preferably at least about 95 wt. % (e.g., from about 98 wt. % to 100 wt. %), more preferably at least about 99 wt. %, and most preferably 100 wt. %. The level of purity of the compounds and salts can be determined using standard methods of analysis. A compound or salt of 100% purity can alternatively be described as one which is free of detectable impurities as determined by one or more standard methods of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, non-nucleoside HIV reverse transcriptase inhibitors, and nucleoside HIV reverse transcriptase inhibitors.

(e) A pharmaceutical combination which is (i) a compound of Formula I and (ii) an anti-HIV agent selected from the group consisting of HIV antiviral agents, immunomodulators, and anti-infective agents; wherein the compound of Formula I and the anti-HIV agent are each employed in an amount that renders the combination effective for the inhibition of HIV integrase, for the treatment or prophylaxis of infection by HIV, or for the treatment, prophylaxis or delay in the onset of AIDS.

(f) The combination of (e), wherein the anti-HIV agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject an effective amount of a compound of Formula I.

(h) A method for the treatment or prophylaxis of infection by HIV in a subject in need thereof which comprises administering to the subject an effective amount of a compound of Formula I.

(i) The method of (h), wherein the compound of Formula I is administered in combination with an effective amount of at least one antiviral selected from the group consisting of HDTV protease inhibitors, non-nucleoside HIV reverse transcriptase inhibitors, and nucleoside HIV reverse transcriptase inhibitors.

(j) A method for the treatment, prophylaxis, or delay in the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, and nucleoside HIV reverse transcriptase inhibitors.

(l) A method of inhibiting HIV integrase in a subject in need thereof which comprises administering to the subject the pharmaceutical composition of (a), (b), (c) or (d) or the combination of (e) or (f).

(m) A method for the treatment or prophylaxis of infection by HIV in a subject in need thereof which comprises administering to the subject the pharmaceutical composition of (a), (b), (c) or (d) or the combination of (e) or (f).

(n) A method for the treatment, prophylaxis, or delay in the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) the inhibition of HIV integrase, (b) treatment or prophylaxis of infection by HIV, or (c) treatment, prophylaxis, or delay in the onset of AIDS. In these uses, the compounds of the present invention can optionally be employed in combination with one or more anti-HIV agents selected from HIV antiviral agents, anti-infective agents, and immunomodulators, Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, subclasses, or features of the compounds described above. In all of these embodiments, the compound may optionally be used in the form of a pharmaceutically acceptable salt.

The present invention also includes prodrugs of the compounds of Formula I. The term "prodrug" refers to a derivative of a compound of Formula I, or a pharmaceutically acceptable salt thereof, which is converted in vivo into Compound I. Prodrugs of compounds of Formula I can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). The prodrug can be, for example, a derivative of a hydroxy group such as an ester (—OC(O)R), a carbonate ester (—OC(O)OR), a phosphate ester (—O—P(=O)(OH)$_2$), or an ether (—OR). Other examples include the following: When the compound of Formula I contains a carboxylic acid group, the prodrug can be an ester or an amide, and when the compound of Formula I contains a primary amino group, the prodrug can be an amide, carbamate, imine, or a Mannich base. One or more functional groups in Compound I can be derivatized to provide a prodrug thereof. Conventional procedures for the selection and preparation of suitable prodrug derivatives are described, for example, in *Design of Prodrugs*, edited by H. Bundgaard, Elsevier, 1985; C. S. Larsen and J. Ostergaard, "Design and application of prodrugs" in: *Textbook of Drug Design and Discovery*, 3rd edition, edited by C. S. Larsen, 2002, pp. 410-458; and Beaumont et al, *Current Drug Metabolism* 2003, vol. 4, pp. 461-458; the disclosures of each of which are incorporated herein by reference in their entireties. Prodrugs of compounds of Formula I can also be selected and prepared by application of the descriptions in WO 2005/070901 and WO 2005/117904, both herein incorporated by reference in their entireties.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n and isopropyl, ethyl and methyl.

The term "alkylene" refers to any divalent linear or branched chain aliphatic hydrocarbon radical (or alternatively an "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —(CH$_2$)$_{1-6}$—, and subclasses of particular interest include —(CH$_2$)$_{1-4}$—, —(CH$_2$)$_{1-3}$—, —(CH$_2$)$_{1-2}$— and —CH$_2$—. Also of interest is the alkylene —CH(CH$_3$)—.

The term "C(O)" refers to carbonyl. The terms "S(O)$_2$" and "SO$_2$" each refer to sulfonyl. The term "S(O)" refers to sulfinyl.

The symbols "*" and "⌇" at the end of a bond each refer to the point of attachment of a functional group or other chemical moiety to the rest of the molecule of which it is a part.

The terms "cycloalkyl" refers to any cyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series (CH$_2$)$_{0-4}$CF$_3$ (i.e., trifluoromethyl, 2,2,2-trifluoroethyl, 3,3,3-trifluoro-n-propyl, etc.).

Unless expressly stated to the contrary, all ranges cited herein are inclusive. For example, a heterocyclic ring described as containing from "1 to 4 heteroatoms" means the ring can contain 1,2,3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth. As another example, an aryl or heteroaryl described as optionally substituted with "from 1 to 5 substituents" is intended to include as aspects thereof, an aryl or heteroaryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 1 substituent, 2 substituents, 3 substituents, 4 substituents, and 5 substituents.

When any variable (e.g., $R^A$, $R^B$, or AryD) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

It is understood that the right side of a group Y is attached to $R^K$ and the left side of a group Y is attached to the rest of the molecule. Thus, for example, for Y=Cl$_{1-6}$ alkylene-C(O) (e.g., (CH$_2$)$_{1-2}$—(O)), $R^K$ is attached to the carbonyl; i.e., $C_{1-6}$ alkylene-C(O)—$R^K$ (e.g., (CH$_2$)$_{1-2}$—(O)—$R^K$). Similarly, it is understood that the right side of a group Z is attached to $R^L$ and the left side of a group Z is attached to ring A. Thus, for example, for Z=$C_{1-6}$ alkylene-C(O) (e.g., (CH$_2$)$_{1-2}$—(O)), $R^L$ is attached to the carbonyl; i.e., $C_{1-6}$ alkylene-C(O)—$R^L$ (e.g., (CH$_2$)$_{1-2}$—(O)—$R^L$).

The term "substituted" (e.g., as in "is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound.

Any of the various carbocyclic and heterocyclic rings and ring systems defined herein may be attached to the rest of the compound at any ring atom (i.e., any carbon atom or any heteroatom) provided that a stable compound results.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers or enantiomers. All isomeric forms of these compounds, whether isolated or in mixtures, are within the scope of the present invention.

As would be recognized by one of ordinary skill in the art, certain of the compounds of the present invention can exist as tautomers. All tautomeric forms of these compounds, whether isolated or in mixtures, are within the scope of the present invention.

In instances where a hydroxy (—OH) substituent is permitted on a heteroaromatic ring and keto-enol tautomerism is possible, it is understood that the substituent might in fact be present, in whole or in part, in the keto form, as exemplified here for a hydroxypyridinyl substituent:

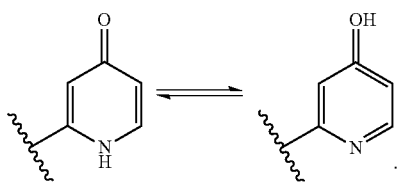

Compounds of the present invention having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

Certain of the compounds of the present invention can exhibit a chirality resulting from the presence of bulky substituents that hinder the otherwise free rotation about a bond. These rotational enantiomers are named atropisomers, and the interconversion can be sufficiently slow to allow for their separation and characterization. See, e.g., J. March, *Advanced Organic Chemistry*. 4th Edition, John Wiley & Sons, 1992, pp. 101-102; and Ahmed et al., *Tetrahedron* 1998, 13277. For example, certain of the compounds of the present invention as exemplified with structures A and B below in which there could be sufficient hindrance to rotation along the bond indicated with an arrow to permit separation of the enantiomers using, e.g., column chromatography on a chiral stationary phase. The present invention includes atropisomers of compounds embraced by Formula I, singly and in mixtures.

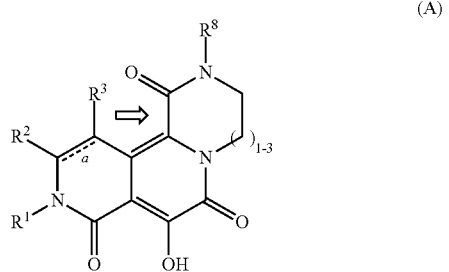

(A)

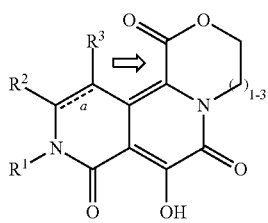

(B)

The compounds of the present inventions are useful in the inhibition of HIV integrase (e.g., HIV-1 integrase), the prophylaxis or treatment of infection by HIV and the prophylaxis, treatment or the delay in the onset of consequent pathological conditions such as AIDS. The prophylaxis of AIDS, treating AIDS, delaying the onset of AIDS, the prophylaxis of infection by HIV, or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention can be commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Certain compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administered" or "administering") in reference to a compound of the invention mean providing the compound or a prodrug of the compound to the individual in need of treatment or prophylaxis. When a compound of the invention or a prodrug thereof is provided in combination with one or more other active agents (e.g., antiviral agents useful for the prophylaxis or treatment of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (or, alternatively, "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated, hi another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of the inhibition of HIV integrase, the prophylaxis or treatment of HIV infection, or the prophylaxis or treatment or delay in the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*. 18th edition, edited by A. R. Gennaro, Mack Publishing Co., 1990 and in *Remington—The Science and Practice of Pharmacy*. 21st edition, Lippincott Williams & Wilkins, 2005.

The compounds of this invention can be administered orally in a dosage range of about 0.001 to about 1000 mg/kg of mammal (e.g., human) body weight per day in a single dose or in divided doses. One preferred dosage range is about 0.01 to about 500 mg/kg body weight per day orally in a single dose or in divided doses. Another preferred dosage range is about 0.1 to about 100 mg/kg body weight per day orally in single or divided doses. For oral administration, the compositions can be provided in the form of tablets or capsules containing about 1.0 to about 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more anti-HIV agents useful in the treatment of HIV infection or AIDS. An "anti-HIV agent" is any agent which is directly or indirectly effective in the inhibition of HIV integrase or another enzyme required for HIV replication or infection, the treatment or prophylaxis of HIV infection, and/or the treatment, prophylaxis or delay in the onset of AIDS. It is understood that an anti-HIV agent is effective in treating, preventing, or delaying the onset of HIV infection or AIDS and/or diseases or conditions arising therefrom or associated therewith. For example, the compounds of this invention may be effectively administered, whether at periods of pre-exposure and/or post-exposure, in combination with effective amounts of one or more HIV antivirals, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, HIV protease inhibitors (e.g., indinavir, atazanavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of HIV infection or AIDS. The HIV antivirals and other agents will typically be employed in these combinations in their conventional dosage ranges and regimens as reported in the art, including, for example, the dosages described in the *Physicians' Desk Reference*. $58^{th}$ edition, Thomson PDR, 2004, or the $59^{th}$ edition thereof, 2005. The dosage ranges for a compound of the invention in these combinations are the same as those set forth above. It is understood that pharmaceutically acceptable salts of the compounds of the invention and/or the other agents (e.g., indinavir sulfate) can be used as well.

Abbreviations employed herein include the following: AcOH=acetic acid; BOC or Boc=t-butyloxycarbonyl; BOP=benzotriazol-1-yloxytris-(dimethylamino)phosphonium; Bu=butyl; DIPEA=diisopropylethylamine (or Hunig's base); DMF=N,N-dimethylformamide; DMSO=dimethylsulfoxide; dppa=diphenylphosphoryl azide; EDC or EDAC=1-ethyl-3-(3-dimethylaminopropyl) carbodiimide; ES MS=electrospray mass spectroscopy; Et=ethyl; EtOAc=ethyl acetate; HOAT=1-hydroxy-7-azabenzotriazole; HPLC=high performance liquid chromatography; LDA=lithium diisopropylamide; LHMDS=lithium hexamethyldisilazide; Me=methyl; MeOH=methanol; MTBE=methyl tert-butyl ether; NaHMDS=sodium hexamethyldisilazide; NMR=nuclear magnetic resonance; TEA=triethylamine; TFA=trifluoroacetic acid; THF=tetrahydrofuran.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme 1 depicts a method for preparing 5,6,7,8-tetrahydro-2,6-naphthyridine-1-carboxylate intermediates useful for making compounds of the present invention. In Part A of the scheme, lactam 1-1 can be alkylated with an appropriate alkyl halide in the presence of a deprotonating agent (e.g., NaH, NaHMDS, or LHMDS) to give 1-2, using methods as described in Jerry March, *Advanced Organic Chemistry*, 3rd edition, John Wiley & Sons, 1985, pp. 377-379. Piperidin-2-one 1-2 can be converted to the corresponding dihydropyridinone compound 1-5 following the two step procedure set forth in Meyers et al, *Tet. Lett*. 1995, 36: 7051-7054, wherein the lactam can be treated with base (e.g., LHMDS, LDA or NaHMDS) and methyl benzene sulfinate to give intermediate 1-4, which can then be treated by heating in a high boiling solvent (e.g., toluene or xylenes) and optionally in the presence of base (e.g., $Na_2CO_3$ or $K_2CO_3$) to effect the elimination to 1-5. Separately, as shown in Part B of Scheme 1, oxazoles of the type 1-9 can readily be prepared by acylating amino acid ester 1-6 with an oxalate ester 1-7 in the presence of base (e.g., tertiary amines such as TEA, DIPEA, or pyridine) to afford acylated compound 1-8, which can then be cyclized and dehydrated (using a dehydrating agent such as $P_2O_5$) in the manner described in Krapcho et al. *J. Heterocyclic Chem*. 1995, 32, 1693-1702 to afford oxazole 1-9. Diels-Alder reaction of 1-9 and 1-5, optionally in the presence of water or an acid (e.g., AcOH or TFA) (preferably in the presence of water as described in "Catalysis of Diels-Alder Reactions in Water and in Hydrogen-Bonding Environments", Wittkopp, A. & Schreiner, P. R. in: Chemistry of Dienes and Polyenes. 2000, Vol. 2, John Wiley & Sons, pp. 1029-1088), will then provide the desired napthyridine intermediate 1-10.

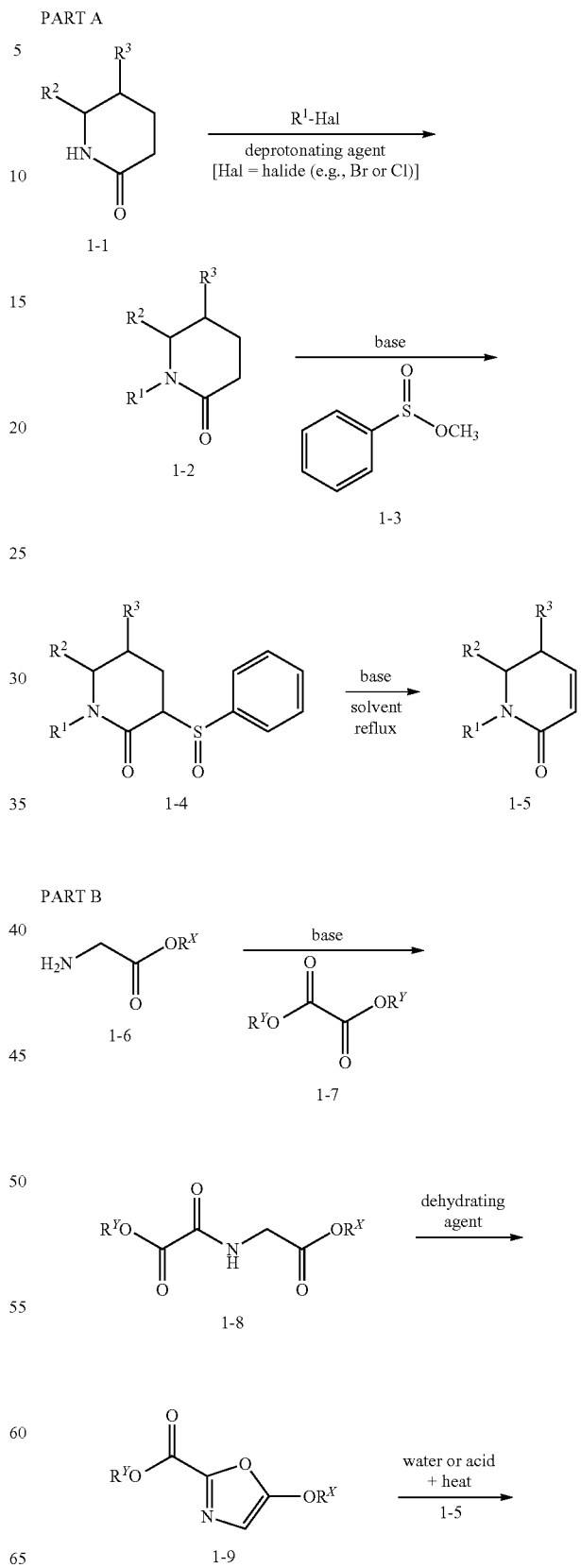

SCHEME 1

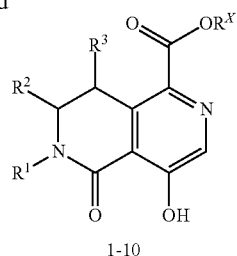

1-10

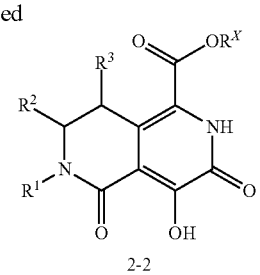

2-2

$$R^X = H, C_{1-6} \text{ alkyl, or } C_{1-6} \text{ alkyl substituted with aryl}$$
$$R^Y = \text{alkyl}$$

Scheme 2 depicts a method for preparing naphthyridine carboxylates and carboxamides embraced by the present invention from naphthyridine intermediate 1-10, wherein the intermediate 1-10 can be treated with a suitable oxidizing agent (e.g., hydrogen peroxide or m-chloroperbenzoic acid) as described in Sharpless et al., *J. Org. Chem.* 1998, 1740 and Caron et al., *Tel Letters* 2000, 2299 and references cited therein to obtain N-oxide 2-1, which can then be treated as described in Suzuki et al., *J. Med. Chem.* 1992, 35, 4045-4053 with acetic anhydride to effect the rearrangement to the O-acylated intermediate, and then treated with a nucleophile (e.g., an alkoxide such as NaOMe) to afford the desired dioxohexahydro-2,6-naphthyridine-1-carboxylate 2-2, In the preparation of compounds of the present invention that require the protection of phenolic hydroxyl group on 2-2, the intermediate 1-10 can be treated with trimethylsilyldiazomethane to provide the O-methyl ether selectively. Chemical transformations similar to those described in the conversion of 1-10 to 2-2 provided 2-5, which can be deprotected to give the desired phenol.

SCHEME 2

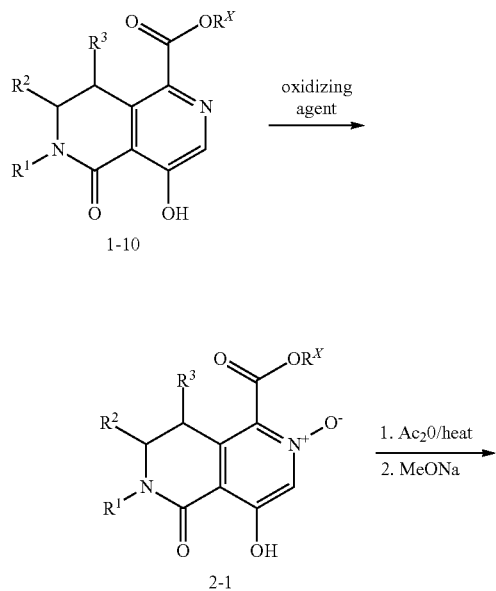

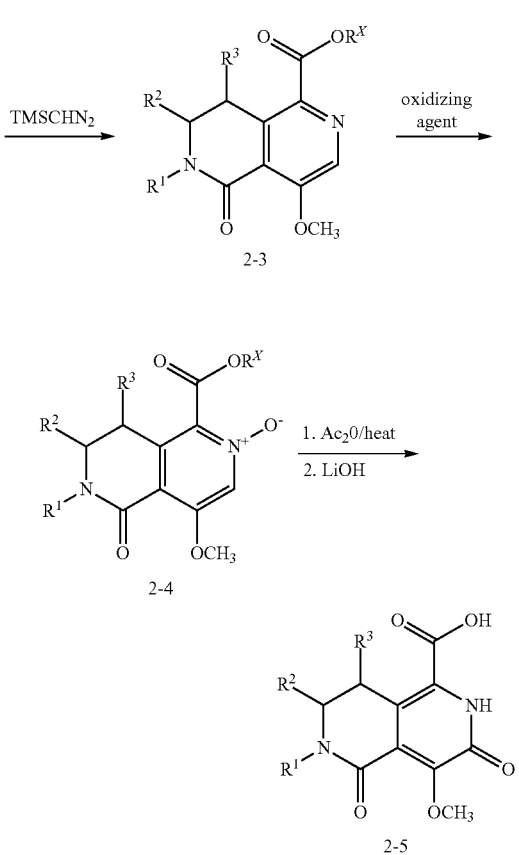

Scheme 3 depicts a method for preparing diazocino[2,1-a]-2,6-naphthyridines 3-3 and 3-4 (n=4) and diazepino[2,1-a]-2,6-naphthyridines 3-3 and 3-4 (n=3) embraced by the present invention from naphthyridine intermediate 2-2, wherein the intermediate 2-2 is treated with a suitable base (e.g., magnesium alkoxide) and a suitable dihaloalkane (e.g., 1-bromo-4-chlorobutane or 1-bromo-3-chloropropane) to provide the alkylated intermediate 3-1. Treatment of halide 3-1 with a primary amine in the presence or absence of an iodide catalyst such as potassium iodide or tetra-n-butylammonium iodide provided the aminoester intermediate 3-2. Base catalyzed hydrolysis of the amino-ester 3-2 provided the corresponding amino acid which was treated with an amide coupling reagent such as EDC or BOP to provide the tricyclic napthyridine products 3-3. The $R^Y$ substituent on 3-3 can be removed under appropriate conditions to provide products 3-4.

SCHEME 3

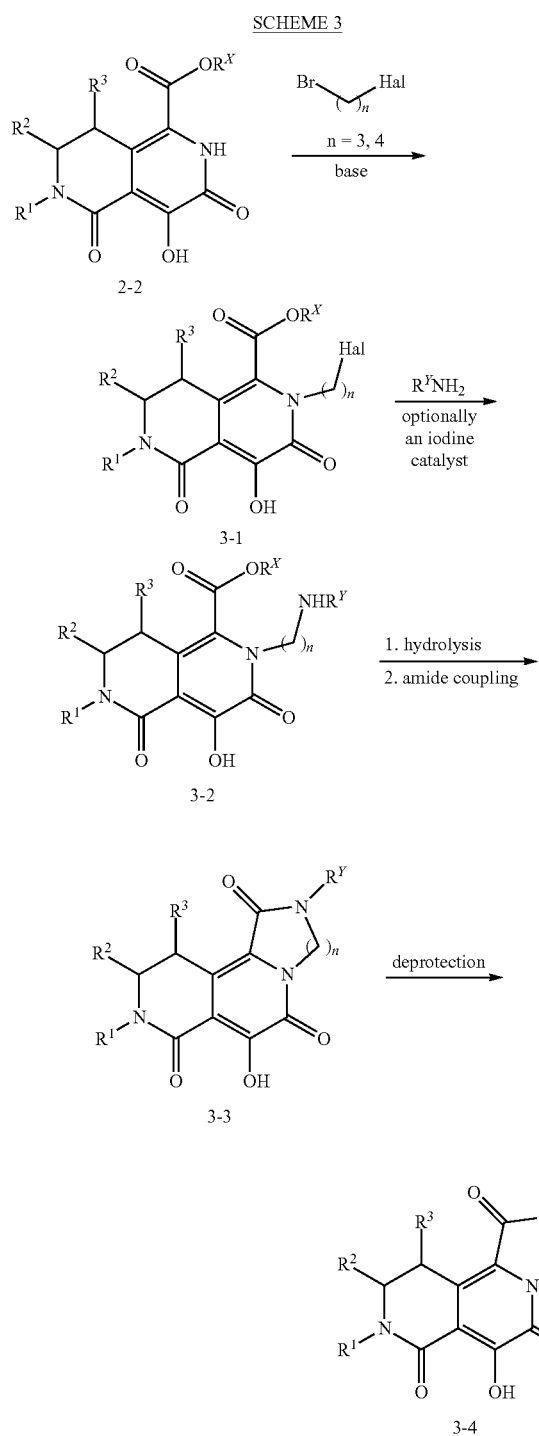

SCHEME 4

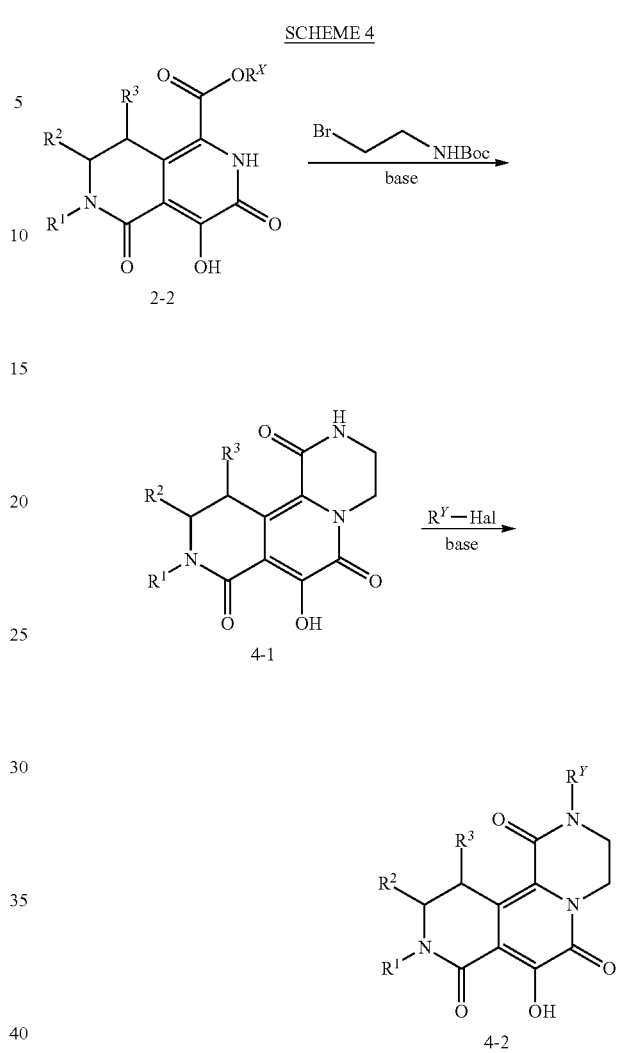

Scheme 4 depicts a method for preparing pyrazino[2,1-a]-2,6-naphthyridines 4-1 and 4-2 embraced by the present invention from naphthyridine intermediate 2-2, wherein the intermediate 2-2 is treated with a suitable base (e.g., magnesium alkoxide, cesium carbonate, or potassium carbonate) and an appropriately protected α-amino-β-haloalkane (e.g., a protected 1-amino-2-haloethane such as tert-butyl (2-bromoethyl)carbamate) to provide the tricyclic napthyridine products 4-1. Treatment of 4-1 with a suitable base and alkylating reagent (e.g., an alkyl halide) affords 4-2.

Scheme 5 depicts a method for preparing oxazino[2,1-a]-2,6-naphthyridines 5-1 embraced by the present invention from naphthyridine intermediate 2-2, wherein the intermediate 2-2 is treated with a suitable base (e.g., magnesium alkoxide, cesium carbonate, or potassium carbonate) and a suitable α,β-dihaloalkane (e.g., a dihaloethane such as 1-bromo-2-chloroethane) to provide the tricyclic napthyridine products 5-1. Oxazepino and oxazocino analogs can be similarly prepared using a suitable dihaloalkane such as Br—CH$_2$CH$_2$CH$_2$—Cl or Br—CH$_2$CH$_2$CH$_2$CH$_2$—Cl.

SCHEME 5

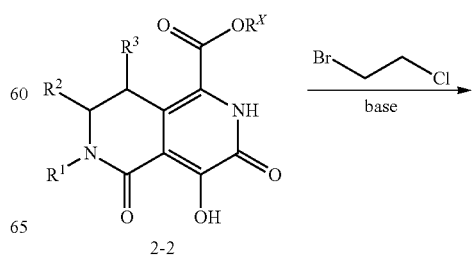

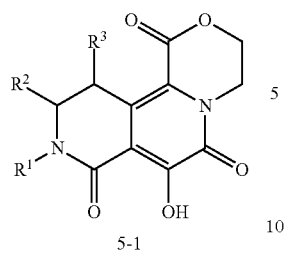

5-1

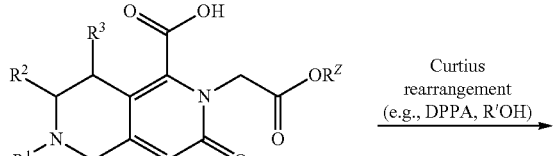

6-2

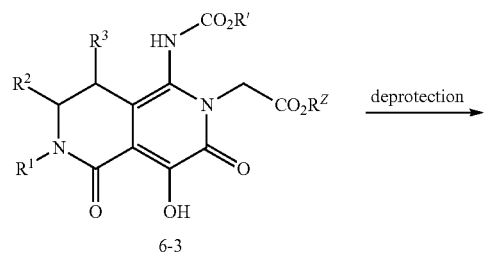

6-3

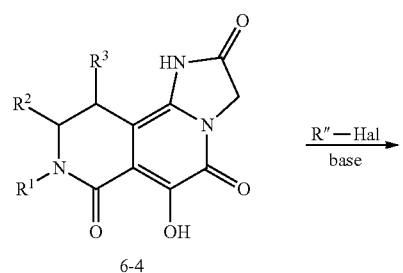

6-4

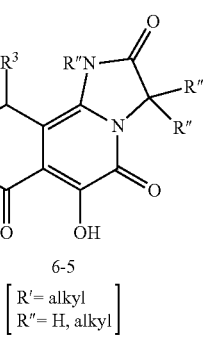

6-5

$$\begin{bmatrix} R' = \text{alkyl} \\ R'' = \text{H, alkyl} \end{bmatrix}$$

Scheme 6 depicts a method for preparing imidazo[2,1-a]-2,6-naphthyridines 6-4 and 6-5 embraced by the present invention from naphthyridine intermediate 2-2, wherein the intermediate 2-2 is treated with a suitable base (e.g., magnesium alkoxide, cesium carbonate, or potassium carbonate) and a suitable substituted alkyl haloacetate (e.g., tert-butyl bromoacetate) to provide the alkylation product 6-1. Selective hydrolysis provides the naphthyridine carboxylic acid 6-2, which can be converted to the corresponding tert-butyl carbamate 6-3 via a Curtius rearrangement in the manner described in J. March, *Advanced Organic Chemistry*. 3rd edition, John Wiley & Sons, 1992, p. 1091 (e.g., acid 6-2 can be treated with diphenylphosphoryl azide in the presence of anhydrous tert-butanol to afford carbamate 6-3). Carbamate 6-3 can then be treated with acid (e.g., HCl or TFA) in a manner similar to the conditions described in T. W. Greene & P. G. M. Wuts, *Protective Groups in Organic Synthesis*. 3rd edition, John Wiley & Sons, 1999, to provide the tricyclic naphthyridine derivative 6-4. Treatment of 6-4 with a suitable alkylating agent (e.g., an alkyl halide, an alkyl bromoacetate, or a benzyloxyalkyl halide) in the presence of base (e.g., NaH, NaHMDS, LHMDS, or LDA) affords product 6-5. Further conventional functional group interconversion on the R" side chain can provide additional compounds of the present invention.

SCHEME 6

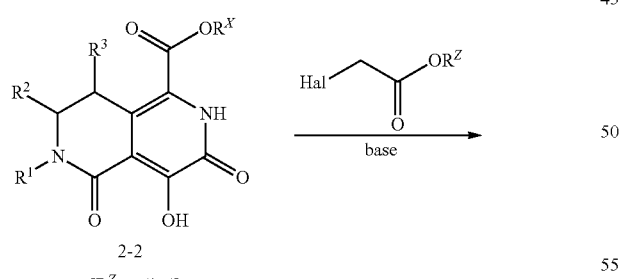

2-2

[$R^Z$ = alkyl]

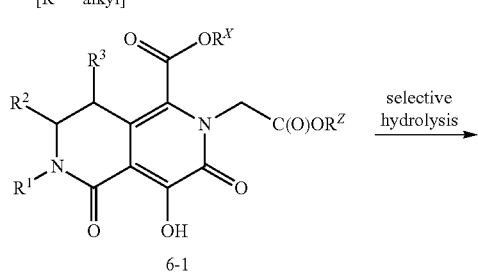

6-1

Scheme 7 depicts a method for preparing 3,4,5,6,12,13-hexahydro-2H[1,4]diazocino[2,1-a]-2,6-naphthyridine-1,8,10(11H)-trione 7-3 from naphthyridine intermediate 2-5, wherein the intermediate 2-5 is treated with a suitable substituted aminoalcohol and an amide coupling reagent (e.g., EDC or BOP) to provide the amide product 7-1. Sequential treatment of 7-1 with alkyl or aryl sulfonic anhydride (e.g., methanesulfonic anhydride) followed by a suitable base (e.g., cesium carbonate) provides the tricyclic naphthyridine derivative 7-2. Further standard functional group interconversion on the side chains $R^a$ to $R^g$ and removal of the methyl ether protecting group provided the targeted inhibitors 7-3.

SCHEME 7

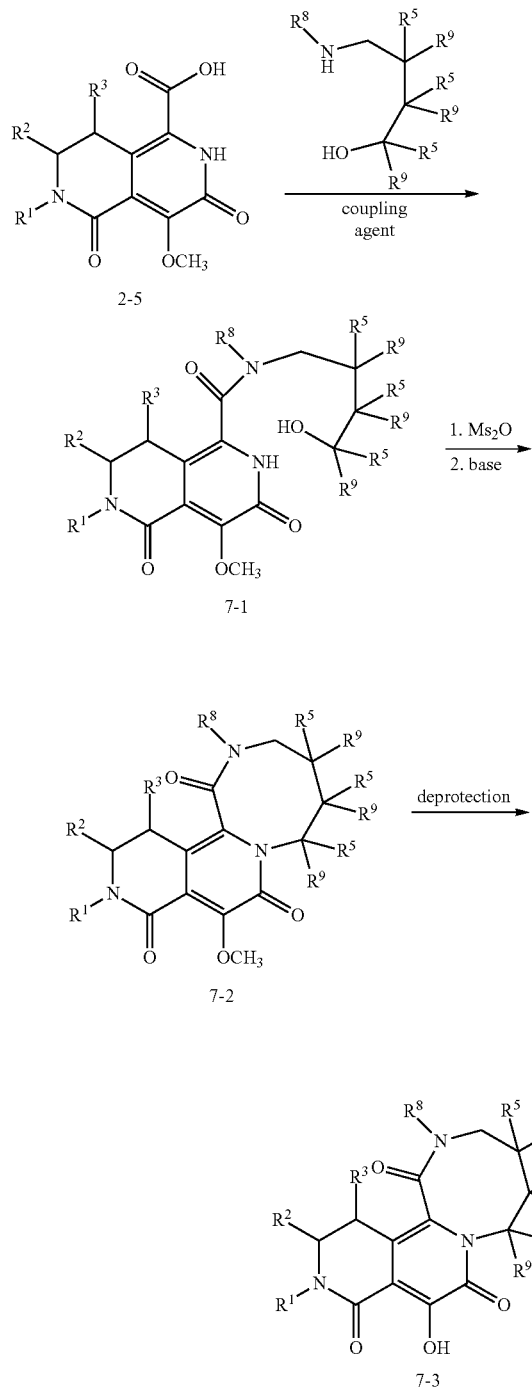

SCHEME 8

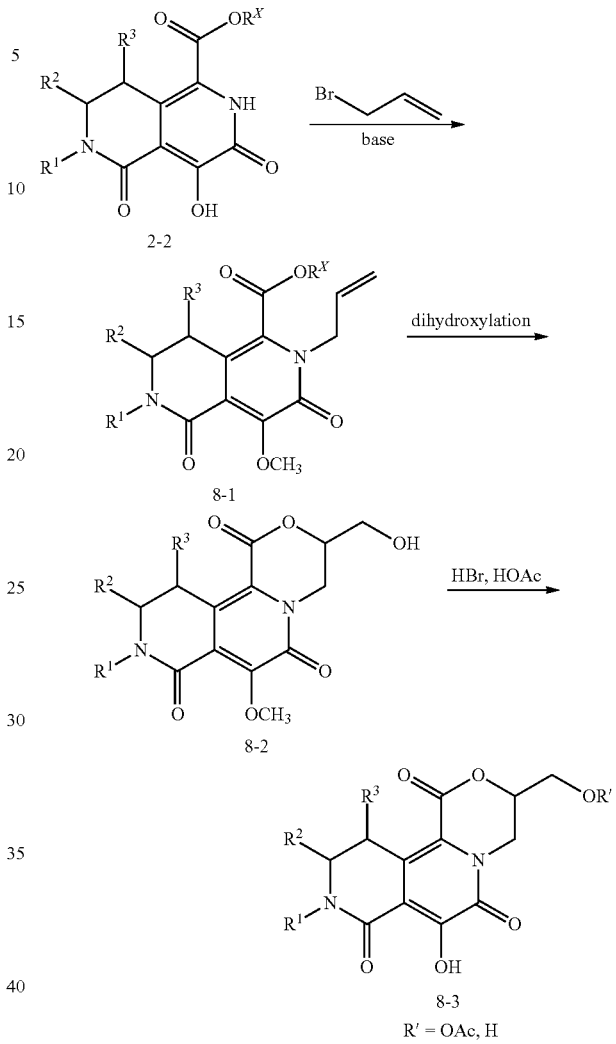

Scheme 8 depicts a method for preparing oxazino[2,1-a]-2,6-naphthyridines from naphthyridine intermediate 2-2, wherein the intermediate 2-2 is treated with a suitable base (e.g., magnesium alkoxide, cesium carbonate, or potassium carbonate) and a suitable allyl halide (e.g., allyl bromide) to provide the allylated napthyridine product 8-1. Osmium tetroxide-catalyzed dihydroxylation of the terminal olefin (VanRheenen et. al. Tet. Lett. 1973, 1976) followed by intramolecular cyclization provides the intermediate oxazinonaphthyridine 8-2. Deprotection of the methyl ether protecting group on 8-2 provides the target compound 8-3.

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3rd edition, 1999, and 2nd edition, 1991. The protecting groups may be removed at a convenient subsequent stage using methods known in the art. Alternatively the interfering group can be introduced into the molecule subsequent to the reaction step of concern.

The following examples serve only to illustrate the invention and its practice. The examples are not to be construed as limitations on the scope or spirit of the invention.

Example 1

11-(3-Chloro-4-fluorobenzyl)-9-hydroxy-2-methyl-3,4,5,6,12,13-hexahydro-2H[1,4]diazocino[2,1-a]-2,6-naphthyridine-1,8,10(11H)-trione

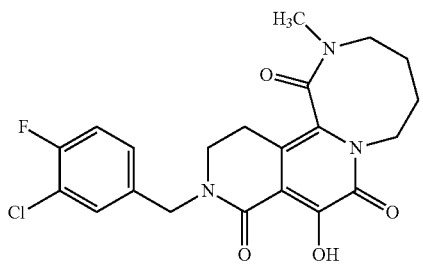

Step 1: 1-(3-Chloro-4-fluorobenzyl)piperidin-2-one

To a cold (0° C.) solution of valerolactam (153.30 g, 1.54 mol) in anhydrous 1-methyl-2-pyrrolidinone (3.5 L), sodium hydride (67.7 g, 1.69 mol, 60% dispersion in oil) was added over a period of 5 minutes. The reaction mixture was stirred for 30 minutes, and a solution of 3-chloro-4-fluorobenzylbromide (345.5 g, 1.54 mol) in 1-methyl-2-pyrrolidinone (200 mL) was added over 30 minutes at 0° C. The reaction mixture was stirred at 0° C. for 1 hour, and was allowed to warm up and stirred at room temperature overnight. The reaction mixture was quenched with distilled water (5 L), and extracted with dichloromethane (three times; 2 L, 1 L, 1 L). The organic extracts were combined, washed with water (3×; 4 L each time). The residual oil was dissolved in ethyl acetate (4 L), and extracted with water (3×; 2 L each time). The organic layer was separated, concentrated under vacuum to give the title product that solidified upon standing.

$^1$H NMR (400 MHz, CDCl$_3$) δ 7.24 (m, 2H), 7.0 (m, 2H), 7.1 (m, 1H), 4.56 (s, 2H), 3.19 (t, J=4.9 Hz, 2H), 2.46 (t, J=6.4 Hz, 2H), 1.8-1.75 (m, 4H).

Step 2: 1-(3-Chloro-4-fluorobenzyl)-5,6-dihydropyridin-2(1H)-one

To a cold (−20° C.) solution of 1-(3-chloro-4-fluorobenzyl) piperidin-2-one (340 g, 1.41 mol) in anhydrous tetrahydrofuran (5 L) under an atmosphere of nitrogen, a solution of lithium bis(trimethylsilyl)amide (3.09 L, 3.09 mol; 1M in THF) was added over a period of 40 minutes with the temperature of the reaction maintained at −20° C. After the addition was complete, the reaction mixture was stirred at −20° C. for one hour. Methyl benzene sulfonate (231 mL, 1.69 mol) was added to the reaction mixture over a period of 30 minutes. The reaction mixture was stirred at −20° C. for 30 minutes. The product mixture was diluted with ethyl acetate (4 L) and washed with water (four times; 2 L each time). The organic extract was concentrated under vacuum. The residue was dissolved in toluene (4 L), treated with solid sodium carbonate (500 g), and heated at 100° C. for one hour. The product mixture was diluted with ethyl acetate (4 L) and washed with water (4 times; 2 L each). The organic extract was concentrated under vacuum. The residue was subjected to column chromatography on silica gel eluting with a gradient of 0-60% EtOAc in heptane. Collection and concentration of appropriate fractions provide the title compound as oil.

$^1$H NMR (400 MHz, CDCl$_3$) δ 7.3 (m, 1H), 7.15 (m, 1H), 7.1 (t, 1H), 6.6 (m, 1H), 6.0 (m, 1H), 4.55 (s, 2H), 3.33 (t, 2H), 1.38 (m, 2H). ES MS M+1=240.13

Step 3: 2-Butoxy-2-oxoethanaminium chloride

To a suspension of glycine hydrochloride (400 g, 3.58 mol) in n-butanol (8 L), thionyl chloride (1.37 L, 18.84 mol) was added slowly dropwise. After addition was complete, the reaction was heated at 70° C. overnight. The product mixture was concentrated under vacuum and the residue was triturated with a mixture of heptane/ethyl acetate. The white solid precipitated was filtered and dried under a stream of dry nitrogen to provide the title compound.

$^1$H NMR (400 MHz, CDCl$_3$) δ 8.5 (br s, 3H), 4.18 (t, J=6.7 Hz, 2H), 4.0 (br s, 2H), 1.62 (m, 2H), 1.38 (m, 2H), 0.92 (t, J=7.4 Hz, 3H). ES MS M+1=132.

Step 4: Butyl N-[ethoxy(oxo)acetyl]glycinate

A mixture of 2-butoxy-2-oxoethanaminium chloride (573.5 g, 3.42 mol), triethylamine (415 g, 4.1 mol), and diethyl oxalate (1.0 kg, 6.8 mol) in ethanol (7 L) was heated at 50° C. for 3 hours. The product mixture was cooled and concentrated under vacuum. The residue was dissolved in methylene chloride and washed with two 4 L portions of water. The organic fraction was dried over anhydrous magnesium sulfate, filtered, and concentrated under vacuum. The residual oil was subjected to column chromatography on silica gel eluting with heptane/ethyl acetate gradient. Collection and concentration of appropriate fractions provided the title material.

$^1$H NMR (400 MHz, CDCl$_3$) δ 7.56 (br s, 1H), 4.37 (q, 7.2 Hz, 2H), 4.2 (t, J=6.6 Hz, 2H), 4.12 (d, J=5.5 Hz, 2H), 1.64 (p, J=6.8 Hz, 2H), 1.39 (t, J=7.15 Hz, 3H), 1.37 (m, 2H), 0.94 (t, J=7.4 Hz, 3H). ES MS M+1=232.

Step 5: Ethyl 5-butoxy-1,3-oxazole-2-carboxylate

To a solution of butyl N-[ethoxy(oxo)acetyl]glycinate (783 g, 3.38 mol) in acetonitrile (8 L) in a 50 L glass reactor with overhead stirrer, phosphorus pentoxide (415 g, 2.92 mol) was added in portions. The reaction was heated at 60° C. for 1 hour. The product mixture was cooled, and water (8 L) was added with the mixture maintained at 20° C. The resultant mixture was extracted with dichloromethane (8 L, and 3 times 2 L). The organic extracts were combined, washed twice with saturated aqueous sodium bicarbonate (8 L total), dried over anhydrous magnesium sulfate, filtered and concentrated under vacuum. The residual oil was subjected to column chromatography on silica gel eluting with 0-30% heptane/ethyl acetate gradient. Collection and concentration of appropriate fractions provided the title material.

$^1$H NMR (400 MHz, CDCl$_3$) δ 6.33 (s, 1H), 4.42 (q, J=7.2 Hz, 2H), 4.18 (t, J=6.4 Hz, 2H), 1.8 (p, J=6.4 Hz, 2H), 1.47 (p, J=7.4 Hz, 2H), 1.41 (t, J=7.15 Hz, 3H), 0.97 (t, J=7.4 Hz, 3H). ES MS M+1=214.

Step 6: Ethyl 6-(3-chloro-4-fluorobenzyl)-4-hydroxy-5-oxo-5,6,7,8-tetrahydro-2,6-naphthyridine-1-carboxylate A mixture of ethyl 5-butoxy-1,3-oxazole-2-carboxylate (44.5 g, 208.6 mmol), 1-(3-chloro-4-fluorobenzyl)-5,6-dihydropyridin-2(1H)-one (25 g, 104.3 mmol), and water (2.82 mL, 156.7 mmol) was heated in a sealed heavy walled vessel at 130° C. with stirring for 72 hours. Upon cooling, the product mixture solidified. The solid was triturated with diethyl ether and collected by filtration. The product was further purified by crystallization from boiling ethyl acetate.

$^1$H NMR (400 MHz, CDCl$_3$) δ 12.79 (s, 1H), 8.42 (s, 1H), 7.4 (dd, J=2, 7 Hz, 1H), 7.2 (m, 1H), 7.15 (t, J=8.6 Hz, 1H), 4.7 (s, 2H), 4.4 (q, J=7 Hz, 2H), 3.5 (m, 4H), 1.4 (t, J=7 Hz, 3H). ES MS M+1=379.0

Step 7: Ethyl 6-(3-chloro-4-fluorobenzyl)-4-hydroxy-5-oxo-5,6,7,8-tetrahydro-2,6-naphthyridine-1-carboxylate 2-oxide A mixture of ethyl 6-(3-chloro-4-fluorobenzyl)-4-hydroxy-5-oxo-5,6,7,8-tetrahydro-2,6-naphthyridine-1-carboxylate (22 g, 58 mmol), glacial acetic acid (500 mL), and hydrogen peroxide (65.8 mL, 30% by weight in water) was heated at 100° C. for four hours. The resultant solution was cooled in an ice bath to 25° C. and treated with saturated aqueous sodium sulfite solution while keeping the reaction mixture below 40° C. When starch paper test showed complete consumption of residual peroxide, the solution was concentrated to two third of its volume, pH was adjusted to ~3 with aqueous HCl and the solution was extracted with dichloromethane (3 times). The organic extracts were combined, dried over anhydrous sodium sulfate, filtered and concentrated under vacuum to afford the title product as oil, $^1$H NMR (400 MHz, CDCl$_3$) δ 12.65 (s, 1H), 7.9 (s, 1H), 7.38 (dd, J=2, 7 Hz, 1H), 7.27-7.1 (m, 2H), 4.66 (s, 2H), 4.44 (q, 7 Hz, 2H), 3.52 (t, J=7 Hz, 2H), 2.90 (t, J=7 Hz, 2H), 1.38 (t, J=7 Hz, 3H). ES MS M+1=395.0

Step 8: Ethyl 3,4-bis(acetyloxy)-6-(3-chloro-4-fluorobenzyl)-5-oxo-5,6,7,8-tetrahydro-2,6-naphthyridine-1-carboxylate A solution of ethyl 6-(3-chloro-4-fluorobenzyl)-4-hydroxy-5-oxo-5,6,7,8-tetrahydro-2,6-naphthyridine-1-carboxylate 2-oxide (23 g, 58 mmol) in acetic anhydride (400 mL) was heated under nitrogen at 100° C. for one hour. The product mixture was concentrated under vacuum to the title bisacetate and was used in the following step without further purification.

$^1$H NMR (400 MHz, CDCl$_3$) δ 7.36 (m, 1H), 7.2-7.1 (m, 1H), 7.12 (t, J=8 Hz, 1H), 4.68 (br s, 2H), 4.4 (q, J=7 Hz, 2H), 3.48 (m, 2H), 3.35 (m, 2H), 2.38 (br s, 6H), 1.4 (t, J=7 Hz, 3H). ES MS M+1=394.9

Step 9: Methyl 6-(3-chloro-4-fluorobenzyl)-3,4-dihydroxy-5-oxo-5,6,7,8-tetrahydro-2,6-naphthyridine-1-carboxylate A solution of ethyl 3,4-bis(acetyloxy)-6-(3-chloro-4-fluorobenzyl)-5-oxo-5,6,7,8 tetrahydro-2,6-naphthyridine-1-carboxylate (27.8 g, 58 mmol) and sodium methoxide (41.8 mL, 232 mmol; 30% by weight solution of NaOMe in MeOH) in anhydrous methanol (300 mL) was heated at 40° C. for 5 hours. The volume of the reaction mixture was reduced by a half under vacuum, diluted with anhydrous tetrahydrofuran (400 mL), and treated with an additional solution of sodium methoxide in methanol (33 mL). The reaction mixture was stirred at room temperature overnight and then warmed to 50° C. for four hours. The product mixture was acidified with dilute hydrochloric acid to pH 3 and extracted with chloroform several times. The organic extracts were combined, dried over anhydrous sodium sulfate, filtered, and concentrated under vacuum to provide the title compound as oil.

$^1$H NMR (400 MHz, CDCl$_3$) δ 10.0-8.2 (br s, 1H), 7.38 (dd, J=6.8. 2 Hz, 1H), 7.2 (m, 1H), 7.13 (t, J=8.4 Hz, 1H), 4.68 (s, 2H), 3.92 (s, 3H), 3.46 (t, J=6.4 Hz, 2H), 3.34 (t, J=6.4 Hz, 2H). ES MS M+1=380.9

Step 10: Methyl 2-(4-chlorobutyl)-6-(3-chloro-4-fluorobenzyl)-4-hydroxy-3,5-dioxo-2,3,5,6,7,8-hexahydro-2,6-naphthyridine-1-carboxylate A mixture of 6-(3-chloro-4-fluorobenzyl)-3,4-dihydroxy-N,N-dimethyl-5-oxo-5,6,7,8-tetrahydro-2,6-naphthyridine-1-carboxamide (0.80 g, 2.19 mmol) and magnesium methoxide in methanol (10.6 mL, 6-10% methanol solution available from Aldrich) in DMSO (22 mL) was heated at 60° C. for one hour. Methanol was exhaustively removed under vacuum over 45 minutes. The resulting DMSO solution was treated with 1-bromo-4-chlorobutane (1.80 g, 10.50 mmol) and stirred at 60° C. under an atmosphere of nitrogen for one hour. The reaction mixture was diluted with ethyl acetate and washed with dilute hydrochloric acid. The organic extract was washed with 10% aqueous potassium carbonate, dried over anhydrous sodium sulfate, filtered, and concentrated under vacuum. The residue was triturated with diethyl ether. The solid precipitated was collected by filtration to provide the title compound. ES MS M+1=471

Step 11: Methyl 6-(3-chloro-4-fluorobenzyl)-4-hydroxy-2-[4-(methylamino)butyl]-3,5-dioxo-2,3,5,6,7, 8-hexahydro-2,6-naphthyridine-1-carboxylate A mixture of methyl 2-(4-chlorobutyl)-6-(3-chloro-4-fluorobenzyl)-4-hydroxy-3,5-dioxo-2,3,5,6,7,8-hexahydro-2,6-naphthyridine-1-carboxylate (0.10 g, 0.21 mmol), methylamine in tetrahydrofuran (1 mL, 2M), and tetra-n-butylammonium iodide in tetrahydrofuran (5 mL) was heated at 60° C. for 3 days. The reaction mixture was concentrated under vacuum. The residue was partitioned between dichloromethane and saturated aqueous sodium bicarbonate. The organic extract was washed with brine, dried over anhydrous sodium sulfate, filtered, and concentrated under vacuum to provide the title compound. This was used in the following step without further purification. ES MS M+1=466

Step 12: 6-(3-Chloro-4-fluorobenzyl)-4-hydroxy-2-[4-(methylamino)butyl]-3,5-dioxo-2,3,5,6,7,8-hexahydro-2,6-naphthyridine-1-carboxylic acid Methyl 6-(3-chloro-4-fluorobenzyl)-4-hydroxy-2-[4-(methylamino)butyl]-3,5-dioxo-2,3,5,6,7,8-hexahydro-2,6-naphthyridine-1-carboxylate (0.18 g, 0.38 mmol) and potassium hydroxide (0.17 g, 2.3 mmol) in a mixture of 1:1:1 v/v/v tetrahydrofuran-methanol-water (4.5 mL) was heated at 50° C. overnight. The reaction mixture was concentrated under vacuum. The residue was partitioned between dichloromethane and dilute hydrochloric acid. The aqueous extract was concentrated under vacuum to provide the title compound as hydrochloride salt. This was used in the following step without further purification. ES MS M+1=452

Step 13: 11-(3-Chloro-4-fluorobenzyl)-9-hydroxy-2-methyl-3,4,5,6,12,13-hexahydro-2H[1,4]diazocino[2, 1-a]-2,6-naphthyridine-1,8,10(11H)-trione A solution of 6-(3-chloro-4-fluorobenzyl)-4-hydroxy-2-[4-(methylamino)butyl]-3,5-dioxo-2,3,5,6,7,8-hexahydro-2,6-naphthyridine-1-carboxylic acid (0.18 g, 0.40 mmol), 1-(3-dimethylaminopropyl)-3-ethylcarbodiimide hydrochloride (0.08 g, 0.41 mmol), and 1-hydroxy-7-azabenzotriazole (0.07 g, 0.51 mmol), and N-methylmorpholine (0.35 mL, 3.16 mmol) in anhydrous DMF (3 mL) was stirred at room temperature overnight. The reaction mixture was concentrated under vacuum. The residue was purified by reverse phase high pressure liquid chromatography. Collection and concentration of appropriate fractions provided the title compound.

$^1$H NMR (400 MHz, CDCl$_3$) δ 7.35 (br s, 1H), 7.18 (br s, 1H), 7.13 (m, 1H), 4.80-4.66 (m), 4.55 (d, J=14.7 Hz, 1H), 3.97-2.98 (m), 3.12 (s, 3H), 2.08-1.77 (m, 4H). ES MS exact mass M+1=434.1282

Example 2

11-(4-Fluorobenzyl)-9-hydroxy-2-methyl-3,4,5,6,12,13-hexahydro-2H[1,4]diazocino[2,1-a]-2,6-naphthyridine-1,8,10(11H)-trione

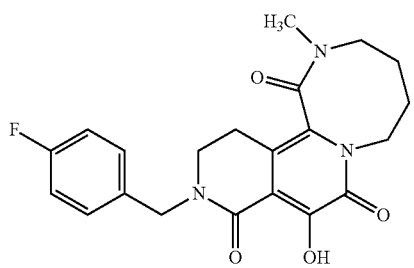

Step 1: Methyl 6-(3-chloro-4-fluorobenzyl)-4-methoxy-2-[4-(methylamino)butyl]-3,5-dioxo-2,3,5,6,7,8-hexahydro-2,6-naphthyridine-1-carboxylate A mixture of methyl 6-(3-chloro-4-fluorobenzyl)-4-hydroxy-2-[4-(methylamino)butyl]-3,5-dioxo-2,3,5,6,7,8-hexahydro-2,6-naphthyridine-1-carboxylate (0.68 g, 1.45 mmol; Example 1, Step 11) and a solution of trimethylsilyldiazomethane in hexane (2.2 mL, 4.35 mmol; 2M) in dichloromethane-methanol (1.5 & 4.5 mL) was stirred at room temperature for one hour. The reaction mixture was concentrated under vacuum to provide the title compound. This was used in the following step without further purification. ES MS M+1=480

Step 2: 11-(3-Chloro-4-fluorobenzyl)-9-methoxy-2-methyl-3,4,5,6,12,13-hexahydro-2H[1,4]diazocino[2,1-a]-2,6-naphthyridine-1,8,10(11H)-trione The titled compound was prepared in a manner similar to that described in Example 1, steps 12 and 13, substituting methyl 6-(3-chloro-4-fluorobenzyl)-4-hydroxy-2-[4-(methylamino)butyl]-3,5-dioxo-2,3,5,6,7,8-hexahydro-2,6-naphthyridine-1-carboxylate with methyl 6-(3-chloro-4-fluorobenzyl)-4-methoxy-2-[4-(methylamino)butyl]-3,5-dioxo-2,3,5,6,7,8-hexahydro-2,6-naphthyridine-1-carboxylate.

Step 3: 11-(4-Fluorobenzyl)-9-methoxy-2-methyl-3,4,5,6,12,13-hexahydro-2H[1,4]diazocino[2,1-a]-2,6-naphthyridine-1,8,10(11H)-trione A mixture of 11-(3-chloro-4-fluorobenzyl)-9-methoxy-2-methyl-3,4,5,6,12,13-hexahydro-2H[1,4]diazocino[2,1-a]-2,6-naphthyridine-1,8,10(11H)-trione (52 mg, 0.12 mmol) and 10% palladium on charcoal (70 mg) in ethanol (6 mL) was stirred at room temperature under a balloon of hydrogen overnight. The reaction mixture was filtered and concentrated under vacuum. ES MS M+1=480

Step 4: 11-(4-Fluorobenzyl)-9-hydroxy-2-methyl-3,4,5,6,12,13-hexahydro-2H[1,4]diazocino[2,1-a]-2,6-naphthyridine-1,8,10(11H)-trione A solution of 11-(4-fluorobenzyl)-9-methoxy-2-methyl-3,4,5,6,12,13-hexahydro-2H[1,4]diazocino[2,1-a]-2,6-naphthyridine-1,8,10(11H)-trione (27 mg, 0.07 mmol) in 30% hydrobromide in acetic acid was stirred at room temperature for 30 minutes. The reaction mixture was concentrated under vacuum. The residue was concentrated from a solution in toluene twice. The resultant solid was triturated with a mixture of diethyl ether and dichloromethane to provide the title compound.

$^1$H NMR (400 MHz, CDCl$_3$) δ 7.40 (dd, J 8.4, 5.5 Hz, 2H), 7.22 (t, J=8.6 Hz, 2H), 4.77 (d, J=14.7 Hz, 1H), 4.71 (d, J=14.7 Hz, 1H), 3.54-3.27 (m), 3.12 (s, 3H), 2.89 (m, 1H), 2.61 (m, 1H), 2.06 (M, 1H), 1.84 (M, 2H), 1.71 (M, 1H). ES MS exact mass M+1=400.1652

Example 3

10-(3-Chloro-4-fluorobenzyl)-8-hydroxy-2-methyl-2,3,4,5,11,12-hexahydro[1,4]diazepino[2,1-a]-2,6-naphthyridine-1,7,9(10H)-trione

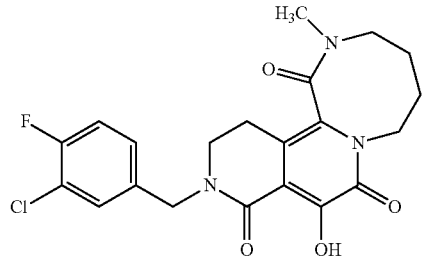

The title compound was prepared in a manner similar to that described in Example 1, substituting 1-bromo-4-chlorobutane with 1-bromo-3-chloropropane in Step 10.

$^1$H NMR (400 MHz, CDCl$_3$) δ 13.40 (br s, 1H), 7.36 (dd, J=6.8, 2.0 Hz, 1H), 7.20 (m, 1H), 7.13 (t, J=8.6, Hz, 1H), 5.28 (m, 1H), 4.73 (d, J=14.5 Hz, 1H), 4.60 (d, J=14.5 Hz, 1H), 3.49-3.14 (m), 3.14 (s, 3H), 2.74 (m, 1H), 2.10 (m, 2H). ES MS exact mass M+1=420.1122

Example 4

10-(3-Chloro-4-fluorobenzyl)-8-hydroxy-2,3,4,5,11,12-hexahydro[1,4]diazepino[2,1-a]-2,6-naphthyridine-1,7,9(10H)-trione

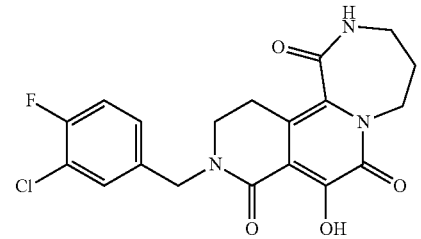

Step 1: 10-(3-Chloro-4-fluorobenzyl)-8-hydroxy-2-(4-methoxybenzyl)-2,3,4,5,11,12-hexahydro[1,4]diazepino[2,1-a]-2,6-naphthyridine-1,7,9(10H)-trione The titled compound was prepared in a manner similar to that described in Example 1, substituting 1-bromo-4-chlorobutane with 1-bromo-3-chloropropane in Step 10, and replacing methylamine with 4-methoxybenzylamine in Step 11. ES MS M+1=526

Step 2: 10-(3-Chloro-4-fluorobenzyl)-8-hydroxy-2,3,4,5,11,12-hexahydro[1,4]diazepino[2,1-a]-2,6-naphthyridine-1,7,9(10H)-trione A mixture of 10-(3-chloro-4-fluorobenzyl)-8-hydroxy-2-(4-methoxybenzyl)-2,3,4,5,11,12-hexahydro[1,4]diazepino[2,1-a]-2,6-naphthyridine-1,7,9(10H)-trione (18 mg, 30 µmol) and p-toluenesulfonic acid (26 mg, 0.14 mmol) in toluene (0.5 mL) was heated at 110° C. for 8 hours. The reaction mixture was concentrated under vacuum. The residue was purified by reverse phase high pressure liquid chromatography. Collection and lyophilization of appropriate fractions provided the title compound.
$^1$H NMR (400 MHz, CD$_3$OD) δ 7.50 (dd, J=7.0, 2.2 Hz, 1H), 7.34 (m, 1H), 7.23 (t, J=8.8, Hz, 1H), 5.13 (br s, 1H), 4.85 (br s, 2H), 3.13-2.78 (m), 3.29 (s, 3H), 2.03 (br s, 3H). ES MS exact mass M+1=406.0980

Example 5

9-(3-Chloro-4-fluorobenzyl)-7-hydroxy-3,4,10,11-tetrahydro-2H-pyrazino[2,1-a]-2,6-naphthyridine-1,6,8(9H)-trione

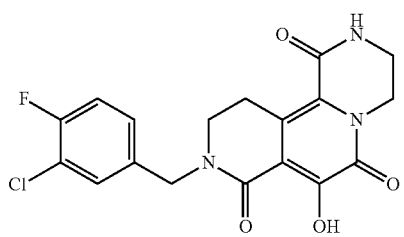

A mixture of 6-(3-chloro-4-fluorobenzyl)-3,4-dihydroxy-N,N-dimethyl-5-oxo-5,6,7,8-tetrahydro-2,6-naphthyridine-1-carboxamide (1.00 g, 2.63 mmol; Example 1, Step 9) and magnesium methoxide in methanol (13.1 mL, 6-10% methanol solution available from Aldrich) in DMSO (26 mL) was heated at 60° C. for one hour. Methanol was exhaustively removed under vacuum over 45 minutes. The resulting DMSO solution was treated with tert-butyl (2-bromoethyl)carbamate (2.94 g, 13.13 mmol) and stirred at 60° C. under an atmosphere of nitrogen for one hour. The reaction mixture was diluted with ethyl acetate and washed successively with 10% sodium thiosulfate and brine. The organic extract was dried over anhydrous sodium sulfate, filtered, and concentrated under vacuum. The residue was purified by reverse phase high pressure liquid chromatography. Collection and lyophilization of appropriate fractions provided the title compound.
$^1$H NMR (400 MHz, CDCl$_3$) δ 14.00 (s, 1H), 7.36 (dd, J=7.0, 2.2 Hz, 1H), 7.21 (m, 1H), 7.14 (t, J=8.8, Hz, 1H), 6.07 (br s, 1H), 4.68 (s, 2H), 4.35 (t, 2H), 3.25 (t, 2H), 3.43 (t, 2H), 3.46 (t, 2H). ES MS exact mass M+1=392.0789

Example 6

9-(3-Chloro-4-fluorobenzyl)-7-hydroxy-2-methyl-3,4,10,11-tetrahydro-2H-pyrazino[2,1-a]-2,6-naphthyridine-1,6,8(9H)-trione

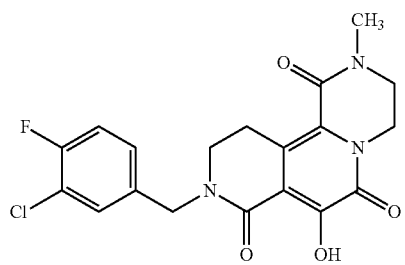

A mixture of 9-(3-chloro-4-fluorobenzyl)-7-hydroxy-3,4,10,11-tetrahydro-2-H-pyrazino[2,1-a]-2,6-naphthyridine-1,6,8(9H)-trione (53 mg, 0.14 mmol; Example 5), and sodium hydride (12.3 mg; 60% dispersion in oil) in DMF (2 mL) was stirred at 0° C. for 20 minutes. To the resultant solution, methyl iodide (96 mg, 0.68 mmoH was added and the reaction mixture was heated at 40° C. for four hours. The reaction mixture was quenched with methanol and concentrated under vacuum. The residue was purified by reverse phase high pressure liquid chromatography. Collection and lyophilization of appropriate fractions provided the title compound.
$^1$H NMR (400 MHz, CDCl$_3$) δ 7.37 (dd, J=6.8, 2.0 Hz, 1H), 7.20 (m, 1H), 7.14 (t, J=8.6, Hz, 1H), 4.68 (s, 2H), 4.35 (t, J=5.3 Hz, 2H), 3.61 (t, J=5.3 Hz, 2H), 3.43 (m, 4H), 3.14 (s, 3H). ES MS exact mass M+1=406.0963

Example 7

9-(3-Chloro-4-fluorobenzyl)-7-hydroxy-3,4,10,11-tetrahydro[1,4]oxazino[3,4-a]-2,6-naphthyridine-1,6,8(9H)-trione

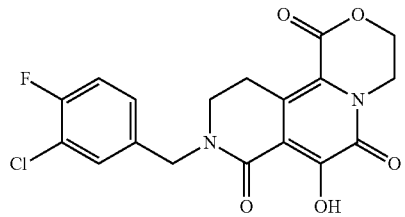

A mixture of 6-(3-chloro-4-fluorobenzyl)-3,4-dihydroxy-N,N-dimethyl-5-oxo-5,6,7,8-tetrahydro-2,6-naphthyridine-1-carboxamide (0.15 g, 0.39 mmol; Example 1, Step 9) and magnesium methoxide in methanol (2 mL, 6-10% methanol solution available from Aldrich) in DMSO (4 mL) was heated at 60° C. for 30 minutes. Methanol was exhaustively removed under vacuum over 45 minutes. The resultant DMSO solution was treated with 1-bromo-2-chloroethane (0.28 g, 1.97 mmol) and stirred at 60° C. under an atmosphere of nitrogen overnight. The reaction mixture was diluted with ethyl acetate and dilute hydrochloric acid. The organic extract was washed with aqueous sodium sulfite, brine, dried over anhydrous sodium sulfate, filtered, and concentrated under vacuum. The residue was purified by reverse phase high pressure liquid chromatography. Collection and lyophilization of appropriate fractions provided the title compound, which was recrystallized from a mixture of ethyl acetate and hexane $^1$H NMR (400 MHz, CDCl$_3$) δ 7.38 (dd, J=6.5, 2.5 Hz, 1H), 7.21 (m, 1H), 7.15 (t, J=8.8, Hz, 1H), 4.69 (s, 2H), 4.55 (br s), 4.36 (br s), 3.96 (br s), 3.52 (t, 2H), 3.48 (t, 2H). ES MS exact mass M+1=393.0652

Example 8

8-(3-Chloro-4-fluorobenzyl)-6-hydroxy-1,3-dimethyl-1,8,9,10-tetrahydroimidazo[2,1-a]-2,6-naphthyridine-2,5,7(3H)-trione

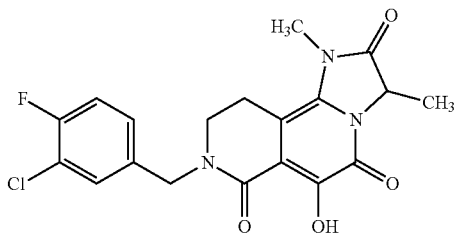

Step 1: Methyl 2-(2-tert-butoxy-2-oxoethyl)-6-(3-chloro-4-fluorobenzyl)-4-hydroxy-3,5-dioxo-2,3,5,6,7,8-hexahydro-2,6-naphthyridine-1-carboxylate A mixture of 6-(3-chloro-4-fluorobenzyl)-3,4-dihydroxy-N,N-dimethyl-5-oxo-5,6,7,8-tetrahydro-2,6-naphthyridine-1-carboxamide (0.50 g, 1.31 mmol; Example 1, Step 9) and magnesium methoxide in methanol (6.6 mL, 6-10% methanol solution available from Aldrich) in DMSO (13 mL) was heated at 60° C. for one hour. Methanol was exhaustively removed under vacuum over 45 minutes. The resultant DMSO solution was treated with tert-butyl bromoacetate (1.80 g, 10.50 mmol) and stirred at 50° C. under an atmosphere of nitrogen for one hour. The reaction mixture was diluted with ethyl acetate and washed with ice cold dilute hydrochloric acid. The organic extract was washed with aqueous sodium thiosulfate, brine, dried over anhydrous sodium sulfate, filtered, and concentrated under vacuum. The residue was triturated with a mixture of diethyl ether and ethyl acetate. The solid precipitated was collected by filtration to provide the title compound. ES MS M+1=495

Step 2: Methyl 2-(2-tert-butoxy-2-oxoethyl)-6-(3-chloro-4-fluorobenzyl)-4-methoxy-3,5-dioxo-2,3,5,6,7,8-hexahydro-2,6-naphthyridine-1-carboxylate A mixture of methyl 2-(2-tert-butoxy-2-oxoethyl)-6-(3-chloro-4-fluorobenzyl)-4-hydroxy-3,5-dioxo-2,3,5,6,7,8-hexahydro-2,6-naphthyridine-1-carboxylate (0.70 g, 1.41 mmol) and a solution of trimethylsilyldiazomethane in hexane (1.0 mL, 2.0 mmol; 2M) in dichloromethane-methanol (4 & 2 mL) was stirred at room temperature overnight. The reaction mixture was concentrated under vacuum. The residue was subject to column chromatography on silica gel euting with 2% methanol in dichloromethane. Collection and concentration of appropriate fractions provided the title compound. ES MS M+1=509

Step 3: 2-(2-tert-Butoxy-2-oxoethyl)-6-(3-chloro-4-fluorobenzyl)-4-methoxy-3,5-dioxo-2,3,5,6,7,8-hexahydro-2,6-naphthyridine-1-carboxylic acid A mixture of methyl 2-(2-tert-butoxy-2-oxoethyl)-6-(3-chloro-4-fluorobenzyl)-4-methoxy-3,5-dioxo-2,3,5,6,7,8-hexahydro-2,6-naphthyridine-1-carboxylate (0.49 g, 0.96 mmol) and lithium hydroxide monohydrate (0.12 g, 2.9 mmol) in a mixture of tetrahydrofuran (3 mL) and water (2 mL) was stirred at room temperature for one hour. The reaction mixture was concentrated under vacuum. The residue was partitioned between dichloromethane and dilute hydrochloric acid. The organic extract was dried over anhydrous sodium sulfate, filtered, and concentrated under vacuum to provide the title compound. This was used in the following step without further purification. ES MS M+1=495

Step 4: 1-[(tert-Butyloxycarbonyl)amino]-2-(2-tert-butoxy-2-oxoethyl)-6-(3-chloro-4-fluorobenzyl)-4-methoxy-3,5-dioxo-2,3,5,6,7,8-hexahydro-2,6-naphthyridine A mixture of 2-(2-tert-butoxy-2-oxoethyl)-6-(3-chloro-4-fluorobenzyl)-4-methoxy-3,5-dioxo-2,3,5,6,7,8-hexahydro-2,6-naphthyridine-1-carboxylic acid (0.31 g, 0.62 mmol), triethylamine (0.10 mL, 0.74 mmol), and diphenylphosphoryl azide (0.19 g, 0.69 mmol) in a mixture of anhydrous dioxane (6 mL) and anhydrous tert-butanol (6 mL) was heated at 90° C. overnight. The reaction mixture was concentrated under vacuum. The residue was subject to column chromatography on silica gel. Collection and concentration of appropriate fractions provided the title compound. ES MS M+1=566

Step 5: 8-(3-Chloro-4-fluorobenzyl)-6-methoxy-1,8,9,10-tetrahydroimidazo[2,1-a]-2,6-naphthyridine-2,5,6(3H)-trione A mixture of 1-[(tert-butylcarbonyl)amino]-2-(2-tert-butoxy-2-oxoethyl)-6-(3-chloro-4-fluorobenzyl)-4-methoxy-3,5-dioxo-2,3,5,6,7,8-hexahydro-2,6-naphthyridine (0.11 g, 0.96 mmol) and hydrogen chloride in dioxane (5 mL, 4 M) was stirred at room temperature for four hours. The reaction mixture was concentrated under vacuum to provide the title compound. This was used in the following step without further purification. $^1$H NMR (400 MHz, CD$_3$OD) δ7.60 (dd, J=7.0, 2.0 Hz, 1H), 7.30 (m, 1H), 7.19 (t, J=8.6, Hz, 1H), 5.44 (s, 1H), 4.83 (s, 2H), 4.72 (s, 2H), 3.90 (s, 3H), 3.51 (t, 7=5.8 Hz, 2H), 2.63 (t, J=5.8 Hz, 2H) ES MS M+1=392

Step 6: 8-(3-Chloro-4-fluorobenzyl)-6-methoxy-1,3-dimethyl-1,8,9,10-tetrahydroimidazo[2,1-a]-2,6-naphthyridine-2,5,6(3H)-trione A mixture of 8-(3-chloro-4-fluorobenzyl)-6-methoxy-1,8,9,10-tetrahydroimidazo[2,1-a]-2,6-naphthyridine-2,5,6(3H)-trione (67 mg, 0.1.7 mmol), sodium hydride (17 mg, 60% dispersion; 0.42 mmol), iodomethane (49 mg, 0.35 mmol) in anhydrous DMF (8 mL) was stirred at room temperature overnight. The reaction mixture was concentrated under vacuum. The residue was subject to column chromatography on silica gel. Collection and concentration of appropriate fractions provided the title compound. $^1$H NMR (400 MHz, CDCl$_3$) δ 7.39 (dd, J=6.8, 2.0 Hz, 1H), 7.23 (m, 1H), 7.12 (t, J=8.6, Hz, 1H), 4.74 (t, J=14.8 Hz, 1H), 4.72 (q, J=6.9 Hz, 1H), 4.63 (t, J=14.8 Hz, 1H), 4.05 (s, 3H), 3.41 (m, 2H), 3.39 (s, 3H), 2.92 (m, 2H), 1.74 (d, J=6.9 Hz, 3H). ES MS M+1=420

Step 7: 8-(3-Chloro-4-fluorobenzyl)-6-hydroxy-1,3-dimethyl-1,8,9,10-tetrahydroimidazo[2,1-a]-2,6-naphthyridine-2,5,7(3H)-trione A mixture of 8-(3-chloro-4-fluorobenzyl)-6-methoxy-1,3-dimethyl-1,8,9,10-tetrahydroimidazo[2,1-a]2,6-naphthyridine-2,5,6(3H)-trione (10 mg, 23 μmol) and 33% hydrogen bromide in acetic acid (1 mL) was stirred at room temperature for two hours. The reaction mixture was concentrated under vacuum. The residue was triturated with diethyl ether and filtered to provide the title compound. $^1$H NMR (400 MHz, CDCl$_3$) δ 7.38 (dd, J=6.8, 2.0 Hz, 1H), 7.23 (m, 1H), 7.12 (t, J=8.6, Hz, 1H), 4.71 (br signals, 3H), 3.47 (br signals, 2H), 3.40 (br s, 3H), 3.12 (br s, 2H), 1.76 (br signals, 3H) ES MS exact mass M+1=406.0969

Example 9

8-(3-Chloro-4-fluorobenzyl)-6-hydroxy-1,3,3-trimethyl-1,8,9,10-tetrahydroimidazo[2,1a]-2,6-naphthyridine-2,5,7(3H)-trione

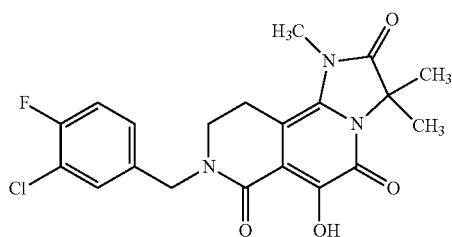

The titled compound was prepared in a manner similar to that described in Example 8. In Step 6, additional sodium hydride and methyl iodide were added for trimethylation. $^1$H NMR (400 MHz, CDCl$_3$) δ 7.36 (dd, J=6.8, 2.0 Hz, 1H), 7.23 (m, 1H), 7.16 (t, J=8.6, Hz, 1H), 4.69 (br s, 3H), 3.48 (br signals, 2H), 3.40 (s, 3H), 3.10 (br s, 2H), 1.79 (br s, 6H) ES MS exact mass M+1=420.1112

Example 10

11-(3-Chloro-4-fluorobenzyl)-9-hydroxy-2-[2-(acetyloxy)ethyl]-3,4,5,6,12,13-hexahydro-2H[1,4]diazocino[2,1-a]-2,6-naphthyridine-1,8,10(11H)-trione

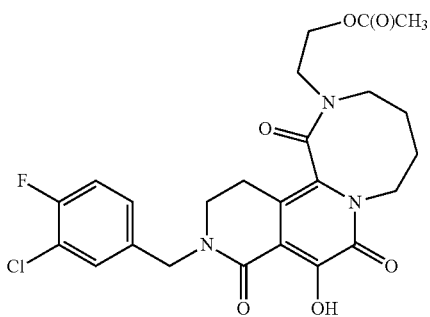

Step 1: Ethyl 6-(3-chloro-4-fluorobenzyl)-4-hydroxy-5-oxo-5,6,7,8-tetrahydro-2,6-naphthyridine-1-carboxylate A mixture of ethyl 5-butoxy-1,3-oxazole-2-carboxylate (248 g, 1.16 mol; Example 1, step 5), 1-(3-chloro-4-fluorobenzyl)-5,6-dihydropyridin-2(1H)-one (199.2 g, 0.83 mol; Example 1, step 2), and deionized water (22.5 mL, 1.25 mol) in a glass lined stainless steel high pressure reactor (with the interstitial space between the liner and the pressure vessel was filled with water) was heated at 135° C. with stirring for 72 hours. The product mixture was cooled in an ice-water bath and the gaseous by-product was carefully vented. The orange solid product was triturated with methyl tert-butyl ether (300 mL) and collected by filtration. The product recrystallized from boiling ethanol-water (~500 mL, 9:1 v/v), collected by filtration, washed successively with a small quantity of ethanol, methyl tert-butyl ether (300 mL), and heptane (200 mL), and air dried to afford the title compound.

$^1$H NMR (400 MHz, CDCl$_3$) δ 12.79 (s, 1H), 8.42 (s, 1H), 7.4 (dd, J=2, 7 Hz, 1H), 7.2 (m, 1H), 7.15 (t, J=8.6 Hz, 1H), 4.7 (s, 2H), 4.4 (q, J=7 Hz, 2H), 3.5 (m, 4H), 1.4 (t, J=7 Hz, 3H). (ES MS M+1=379.0)

Step 2: Ethyl 6-(3-chloro-4-fluorobenzyl)-4-methoxy-5-oxo-5,6,7,8-tetrahydro-2,6-naphthyridine-1-carboxylate To a stirred solution of ethyl 6-(3-chloro-4-fluorobenzyl)-4-hydroxy-5-oxo-5,6,7,8-tetrahydro-2,6-naphthyridine-1-carboxylate (208 g, 0.55 mol) in a mixture of dichloromethane (830 mL) and methanol (410 mL) at 10° C., a solution of (trunethyl-silyl)diazomethane (600 mL, 1.2 mol; 2M) in hexanes was added over a period of 1 hour with the reaction temperature maintained below 15° C. The reaction mixture (unstirred) was allowed to stand at 10° C. overnight, and then at 20° C. for additional 4 hours. The reaction mixture was cooled back to 10° C. and quenched with acetic acid (~75 mL). The product mixture was concentrated under vacuum and the residue recrystallized from boiling methyl tert-butyl ether and heptane. The solid recrystallized was collected by filtration, washed with a mixture of methyl tert-butyl ether and heptane (1:1, v/v), and air dried to afford the title compound.

$^1$H NMR (400 MHz, CDCl$_3$) δ 8.42 (s, 1H), 7.41 (dd, J=2, 7 Hz, 1H), 7.24 (m, 1H), 7.11 (t, J=8.6 Hz, 1H), 4.70 (s, 2H), 4.42 (q, J=7 Hz, 2H), 4.12 (s, 3H), 3.4 (m, 4H), 1.42 (t, J=7 Hz, 3H). (ES MS M+1=392.9)

Step 3: Ethyl 3-(acetyloxy)-6-(3-chloro-4-fluorobenzyl)-4-methoxy-5-oxo-5,6,7,8-tetrahydro-2,6-naphthyridine-1-carboxylate To a cold (5° C.) mixture of ethyl 6-(3-chloro-4-fluorobenzyl)-4-methoxy-5-oxo-5,6,7,8-tetrahydro-2,6-naphthyridine-1-carboxylate (199 g, 0.51 mol) and urea hydrogen peroxide (100 g, 1.06 mol) in dichloromethane (1.5 L), trifluoroacetic anhydride was added dropwise over a period of 45 minutes. The resultant homogeneous solution was stirred at 20° C. for 30 minutes and cooled back to 5° C. The reaction mixture was treated with aqueous potassium hydrogen phosphate (pH of aqueous extract increased to 8), followed by slow addition of freshly prepared aqueous sodium bisulfite solution with the temperature of the product mixture maintained below 25° C. The organic extract was separated and the aqueous fraction extracted with toluene (2×). The organic extracts were combined, dried over anhydrous sodium sulfate, filtered, and concentrated under vacuum. Without further purification, a solution of this intermediate N-oxide (~280 g) and acetic anhydride (239 mL, 2.5 mol) in toluene (2 L) was heated at 110° C. for 16 hours. The product mixture was concentrated under vacuum. The resultant oil was concentrated from toluene (300 mL, twice) and stored under vacuum overnight. The acetate product was used in the following step without further purification.
(ES MS M+1=408.9)

Step 4: 6-(3-Chloro-4-fluorobenzyl)-4-methoxy-3,5-dioxo-2,3,5,6,7,8-hexahydro-2,6-naphthyridine-1-carboxylic acid A mixture of ethyl 3-(acetyloxy)-6-(3-chloro-4-fluorobenzyl)-4-methoxy-5-oxo-5,6,7,8-tetrahydro-2,6-naphthyridine-1-carboxylate (217 g, 0.48 mol), lithium hydroxide monohydrate (70.7 g, 1.67 mol), and water (320 mL) in ethanol (1.8 L) was sonicated for 20 minutes. The reaction mixture was cooled in an ice-water bath and treated with hydrochloric acid (425 mL, 3 M). The resultant light yellow solid was filtered, washed successively with water (1 L), a 3:2 v/v mixture of water and ethanol (500 mL), MTBE (750 mL), and air dried. The yellow solid was dissolved in anhydrous DMF (700 mL) and concentrated under vacuum. The procedure was repeated twice to remove residual water. The yellow solid was triturated with MTBE, filtered, and stored under vacuum overnight to afford the title acid.
$^1$H NMR (400 MHz, CDCl$_3$) δ 7.54 (dd, J=2, 7 Hz, 1H), 7.3 (m, 2H), 4.65 (s, 2H), 3.89 (s, 3H), 3.43 (t, J=5.5 Hz, 2H), 3.00 (t, J=5.5 Hz, 2H). (ES MS M+1=380.9)

Step 5: N-[2-(Benzyloxy)ethyl]-4-{[tert-butyl(dimethyl)silyl]oxy}butan-1-amine A mixture of 4-hydroxybutylamine (4.0 g, 44.9 mmol), tert-butyldimethyl-silyl chloride (7.4 g, 49.3 mmol) and imidazole (6.7 g, 98.7 mmol) in dichloromethane (150 mL) was stirred at room temperature for 2 hours. The product mixture was washed successively with aqueous NaHCO$_3$, water, and brine. The organic extract was dried over anhydrous sodium sulfate, filtered, and concentrated under vacuum. This intermediate silylated aminoalcohol was used without further purification. To a mixture of the amine (1.0 g, 4.9 mmol) and benzyloxyacetaldehyde (0.74 g, 4.9 mmol) in dichloroethane (15 mL) at room temperature, sodium triacetoxyborohydride (1.3 g, 6.3 mmol) was added. The reaction mixture was concentrated under vacuum. The residue was partitioned between ethyl acetate and aqueous sodium carbonate. The organic extract was dried over anhydrous sodium sulfate, filtered, and concentrated under vacuum. The residue was subjected to column chromatography on silica gel eluting with 2% methanol in dichloromethane. Collection and concentration of appropriate fractions afforded the title silyloxybutyl-amine.
$^1$H NMR (400 MHz, CDCl$_3$) δ 7.33-7.25 (m, 5H), 4.51 (s, 2H), 3.60 (m, 4H), 2.79 (br t, J=4.9 Hz, 2H), 2.60 (br t, 2H), 1.52 (br signal, 5H), 0.87 (s, 9H), 0.03 (s, 6H).

Step 6: N-[2-(Benzyloxy)ethyl]-N-(4-{[tert-butyl(dimethyl)silyl]oxy}butyl)-6-(3-chloro-4-fluorobenzyl)-4-methoxy-3,5-dioxo-2,3,5,6,7,8-hexahydro-2,6-naphthyridine-1-carboxamide A mixture of 6(3-chloro-4-fluorobenzyl)-4-methoxy-3,5-dioxo-2,3,5,6,7,8-hexahydro-2,6-naphthyridine-1-carboxylic acid (0.19 g, 0.49 mmol), N-[2-(benzyloxy)-ethyl]-4-{[tert-butyl(dimethyl)silyl]oxy}butan-1-amine (0.19 g, 0.55 mmol), EDC (0.10 g, 0.55 mmol), HOAt (75 mg, 0.55 mmol) and diisopropylethylamine (0.35 mL, 1.99 mmol) in DMF (2 mL) was stirred at room temperature overnight. The product mixture was concentrated under vacuum. The residue was partitioned between methylene chloride and water. The organic extract was dried over anhydrous sodium sulfate, filtered, and concentrated under vacuum to afford the title compound. This material was used in the following step without further purification.

Step 7: N-[2-(Benzyloxy)ethyl]-N-(4-hydroxybutyl)-6-(3-chloro-4-flurobenzyl)-4-methoxy-3,5-dioxo-2,3,5,6,7,8-hexahydro-2,6-naphthyridine-1-carboxamide To a solution of N-[2-(benzyloxy)ethyl]-N-(4-{[tert-butyl(dimethyl)silyl]-oxy}butyl)-6-(3-chloro-4-fluorobenzyl)-4-methoxy-3,5-dioxo-2,3,5,6,7,8-hexahydro-2,6-naphthyridine-1-carboxamide (0.41 g, 0.59 mmol) in THF, a solution of tetra-n-butyl-ammonium fluoride (0.65 mL, 1M) in THF was added. The reaction mixture was stirred at room temperature overnight, and concentrated under vacuum. The residue was subjected to column chromatography on silica gel eluting with 3% methanol in dichloromethane. Collection and concentration of appropriate fractions afforded the title compound.

Step 8: N-[2-(Benzyloxy)ethyl]-N-(4-methanesulfonyloxybutyl)-6-(3-chloro-4-fluorobenzyl)-4-methoxy-3,5-dioxo-2,3,5,6,7,8-hexahydro-2,6-naphthyridine-1-carboxamide To a solution of N-[2-(benzyloxy)ethyl]-N-(4-hydroxybutyl)-6-(3-chloro-4-fluorobenzyl)-4-methoxy-3,5-dioxo-2,3,5,6,7,8-hexahydro-2,6-naphthyridine-1-carboxamide (0.20 g, 0.34 mmol) and diisopropylethylamine (0.07 mL, 0.41 mmol) in dichloromethane, methanesulfonic anhydride (71 mg, 0.41 mmol) was added. The reaction mixture was stirred at room temperature for 30 minutes. The product mixture was washed with water. The organic extract was dried over anhydrous sodium sulfate, filtered, and concentrated under vacuum. The residue was subjected to column chromatography on silica gel eluting with 0.5% methanol in dichloromethane. Collection and concentration of appropriate fractions afforded the title compound.
$^1$H NMR (400 MHz, CDCl$_3$) mixture of rotamers δ 7.36-7.08 (m, 8H), 4.64 (s, 1H), 4.57 (s, 1H), 4.50 (s, 1H), 4.33 (s, 1H). 4.06 (s, 3H), 3.75 (s, 2H), 3.69 (q, J=5.7 Hz, 1H), 3.58 (t, J=7.3 Hz, 1H), 3.49 (br m, 3H), 3.44 (s, 1.5H), 3.52 (s, 1.5H), 3.25 (q, J=6.8 Hz, 2H), 2.97 (t, 6.4 Hz, 1H), 2.69 (q, 6.7 Hz, 2 H), 1.78-1.36 (m). (ES MS M+1=664.2)

Step 9: 11-(3-Chloro-4-fluorobenzyl)-9-methoxy-2-[2-(benzyloxy)ethyl]-3,4,5,6,12,13-hexahydro-2H[1,4]diazocino[2,1-a]-2,6-naphthyridine-1,8,10(11H)-trione To a mixture of N-[2-(benzyloxy)ethyl]-N-(4-methanesulfonyloxybutyl)-6-(3-chloro-4-fluorobenzyl)-4-methoxy-3,5-dioxo-2,3,5,6,7,8-hexahydro-2,6-naphthyridine-1-carboxamide (90 mg, 0.14 mmol) and cesium carbonate (53 mg, 0.16 mmol) in DMF was heated at 75° C. for 90 minutes. The product mixture was concentrated under vacuum. The residue was subjected to column chromatography on silica gel eluting with 5% methanol in dichloromethane. Collection and concentration of appropriate fractions afforded the title compound.

¹H NMR (400 MHz, CDCl₃) δ 7.34 (dd, J=2.0, 6.8 Hz, 1H), 7.27-7.08 (m), 7.09 (t, J=8.6 Hz, 1H), 5.28 (s), 4.74 (dd, J=6.2, 13.9 Hz, 1H), 4.67 (d, J=14.8 Hz, 1H), 4.57 (d, 14.8 Hz, 1H), 4.48 (s, 2H), 4.18 (m, 1H), 4.09 (s, 3H), 3.78-3.66 (m, 2H), 3.46-3.16 (m, 6H), 2.70-2.63 (m, 1H), 2.25-2.00 (m, 1H), 1.85-1.72 (m, 1H). (ES MS M+1=569.0)

Step 10: 11-(3-Chloro-4-fluorobenzyl)-9-hydroxy-2-[2-(acetyloxy)ethyl]-3,4,5,6,12,13-hexahydro-2H[1,4]diazocino[2,1-a]-2,6-naphthyridine-1,8,10(11H)-trione A mixture of 11-(3-chloro-4-fluorobenzyl)-9-methoxy-2-[2-(benzyl-oxy)ethyl]-3,4,5,6,12,13-hexahydro-2H[1,4]diazocino[2,1-a]-2,6-naphthyridine-1,8,10(11H)-trione (120 mg, 0.21 mmol) and 33% hydrogen bromide in acetic acid (1 mL) in dioxane (1 mL) was stirred at room temperature for 1 hour. The product mixture was concentrated under vacuum. The residue was subjected to reverse phase column chromatography on C-18 stationary phase eluted with a 95-5% water-acetonitrile gradient. Collection and lyophilization of appropriate fractions afforded the title compound.

¹H NMR (400 MHz, CDCl₃) δ 7.34 (dd, J=6.7, 1.6 Hz, 1H), 7.18 (br signal, 1H), 7.12 (t, J=8.6 Hz, 1H), 4.79 (br signal), 4.76 (d, J=14.7 Hz, 1H), 4.54 (d, J=14.7 Hz, 1H), 4.46 (br signal), 4.18 (m, 2H), 3.48-3.25 (m), 3.00-2.93 (m), 2.61-2.57 (m), 2.03 (s, 3H), 2.09-1.75 (m). (ES MS M+1=506.2)

Example 11

11-(3-Chloro-4-fluorobenzyl)-9-hydroxy-2-(2-hydroxyethyl)-3,4,5,6,12,13-hexahydro-2H[1,4]diazocino[2,1-a]-2,6-naphthyridine-1,8,10(11H)-trione

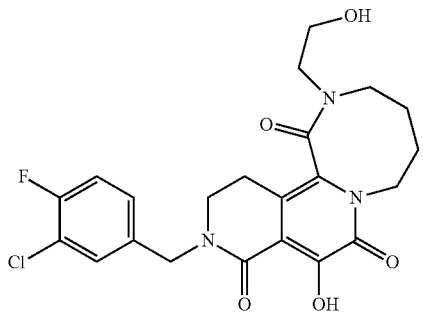

A mixture of 11-(3-chloro-4-fluorobenzyl)-9-hydroxy-2-[2-(acetyloxy)ethyl]-3,4,5,6,12,13-hexahydro-2H[1,4]diazocino[2,1-a]-2,6-naphthyridine-1,8,10(11H)-trione (50 mg, 0.1 mmol) and aqueous lithium hydroxide (0.5 mL, 1M) in THF was stirred at room temperature for 1 hour. The product mixture was concentrated under vacuum. The residue was subjected to reverse phase column chromatography on C-18 stationary phase eluted with a 95-5% water-acetonitrile gradient. Collection and lyophilization of appropriate fractions afforded the title compound.

¹H NMR (400 MHz, CDCl₃) δ 13.17 (br s, 1H), 7.35 (dd, J=6.9, 2.2 Hz, 1H), 7.18 (br signal, 1H), 7.13 (t, J=8.4 Hz, 1H), 4.82 (m, 1H), 4.79 (d, J=15.0 Hz, 1H), 4.54 (d, J=15.0 Hz, 1H), 4.19-4.13 (m, 1H), 3.95-3.82 (m, 2H), 3.49-3.35 (m), 3.29-3.24 (m, 1H), 3.03-2.96 (m, 1H), 2.64-2.57 (m, 1H), 2.13-0.09 (m). (ES MS M+1=464.1378)

Example 12

[11-(3-Chloro-4-fluorobenzyl)-9-hydroxy-1,8,10-trioxo-1,3,4,5,6,8,10,11,12,13-deca-hydro-2H-[1,4]diazocino[2,1-a]-2,6-naphthyridin-2-yl]acetic acid

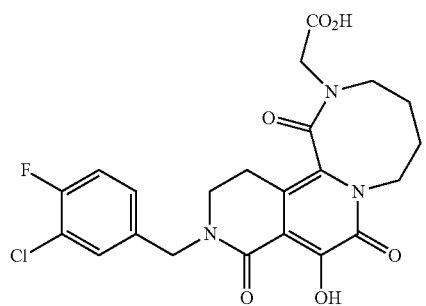

Step 1: tert-Butyl[(4-hydroxybutyl)amino]acetate

To a cold (0° C.) solution of 4-hydroxybutylamine (9.1 g, 101.8 mmol) in diethyl ether (100 mL), a solution of tert-butyl bromoacetate (7.4 g, 49.3 mmol) in diethyl ether (25 mL) was added dropwise over a period of 2 hours. The reaction mixture was allowed to warm up slowly to room temperature and stirred at the temperature overnight. The product mixture was washed successively with aqueous NaHCO₃, water, and brine. The organic extract was dried over anhydrous sodium sulfate, filtered, and concentrated under vacuum. This intermediate was used in the following reaction without further purification.

¹H NMR (400 MHz, CDCl₃) δ 3.58 (t, J=5.3 Hz, 2H), 3.26 (s, 2H), 2.63 (t, J=6.1 Hz, 2H), 1.67-1.58 (m, 4H), 1.45 (s, 9H).

Step 2: tert-Butyl[11-(3-chloro-4-fluorobenzyl)-9-methoxy-1,8,10-trioxo-3,3,4,5,6,8,10,11,12,13-decahydro-2H-[1,4]diazocino[2,1-a]-2,6-naphthyridin-2-yl]acetate The title compound was prepared in a manner similar to that described in Example 10, steps 6 to 8, substituting N-[2-(benzyloxy)ethyl]-4-{[tert-butyl(dimethyl)-silyl]oxy}butan-1-amine with tert-butyl [(4-hydroxybutyl)amino]acetate in step 6.

¹H NMR (400 MHz, CDCl₃) δ 7.45 (dd, J=6.7, 1.6 Hz, 1H), 7.18 (br signal, 1H), 7.08 (t, J=8.6 Hz, 1H), 4.75 (dd, J=13.9, 6.0 Hz, 1H), 4.67 (d, J=14.7 Hz, 1H), 4.63 (d, J=14.7 Hz, 1H), 4.25 (d, J=16.8 Hz, 1H), 4.11 (s, 3H), 3.91 (d, J=16.8 Hz, 1H), 3.68 (dd, J=10.8, 13.7 Hz, 1H), 3.48-3.34 (m), 3.19 (dd, J=4.15 Hz, 1H), 2.86-2.79 (m), 2.55-2.48 (m, 1H), 2.11-2.08 (m), 1.89-1.74 (m). (ES MS M+1=549)

Step 3: [11-(3-Chloro-4-fluorobenzyl)-9-hydroxy-1,8,10-trioxo-1,3,4,5,6,8,10,11,12,13-deca-hydro-2H-[1,4]diazocino[2,1-a]-2,6-naphthyridin-2-yl]acetic acid A mixture of tert-butyl[11-(3-chloro-4-fluorobenzyl)-9-methoxy-1,8,10-trioxo-1,3,4,5,6,8,10,11,12,13-decahydro-2H-[1,4]diazocino[2,1-a]-2,6-naphthyridin-2-yl]acetate (50 mg, 0.09 mmol) and 33% hydrogen bromide in acetic acid (1 mL) in dioxane (1 mL) was stirred at room temperature for 1 hour. The product mixture was concentrated under vacuum. The residue was subjected to reverse phase column chromatography on C-18 stationary phase eluted with a 95-5% water-acetonitrile gradient. Collection and lyophilization of appropriate fractions afforded the title compound.

$^1$H NMR (400 MHz, CDCl$_3$) δ 7.34 (dd, J 6.6, 2.1. Hz, 1H), 7.18 (br signal, 1H), 7.11 (t, J=8.4 Hz, 1H), 4.78 (d, J=14.8 Hz, 1H), 4.52 (d, J=14.8 Hz, 1H), 4.41 (d, J=17.8 Hz, 1H), 4.07 (d, J=17.8 Hz, 1H), 3.67 (m, 1H), 3.51-3.36 (m), 3.23 (br d, 1H), 2.96 (m), 2.60 (m, 1H), 2.08 (m), 1.96 (m), 1.76 (m). (ES MS M+1=478.2)

Example 13

2-[11-(3-Chloro-4-fluorobenzyl)-9-hydroxy-1,8,10-trioxo-1,3,4,5,6,8,10,11,12,13-deca-hydro-2H-[1,4]diazocino[2,1-a]-2,6-naphthyridin-2-yl]-N,N-dimethylacetamide

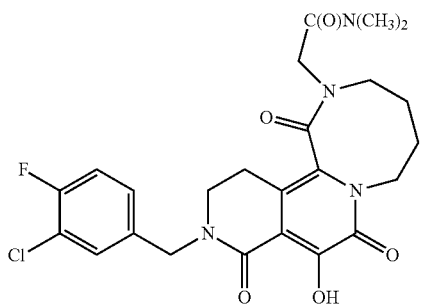

Step 1: 2-[11-(3-Chloro-4-fluorobenzyl)-9-hydroxy-1,8,10-trioxo-1,3,4,5,6,8,10,11,12,13-deca-hydro-2H-[1,4]diazocino[2,1-a]2,6-naphthyridin-2-yl]-N,N-dimethylacetamide A solution of [11-(3-chloro-4-fluorobenzyl)-9-hydroxy-1,8,10-trioxo-1,3,4,5,6,8,10,11,12,13-deca-hydro-2H-[1,4]diazocino[2,1-a]-2,6-naphmyridin-2-yl]acetic acid (25 mg, 0.05 mmol), BOP (28 mg, 0.06 mmol), diisopropylethylamine (7 mg, 0.07 mmol) and dimethylamine (0.11 mL, 2M in THF) in DMF (0.5 mL) was stirred at room temperature overnight. The product mixture was concentrated under vacuum. The residue was subjected to reverse phase column chromatography on C-18 stationary phase eluted with a 95-5% water-acetonitrile gradient. Collection and lyophilization of appropriate fractions afforded the title compound.

$^1$H NMR (400 MHz, CDCl$_3$) δ 13.2 (br s, 1H), 7.35 (d, J=6.8 Hz, 1H), 7.18 (br signal, 1H), 7.12 (t, J=8.4 Hz, 1H), 4.84 (m, 1H), 4.80 (d, J=14.8 Hz, 1H), 4.66 (d, J=16.1 Hz, 1H), 4.52 (d, J=14.8 Hz, 1H), 3.89 (d, J=15.9 Hz, 1H), 3.68 (app t, J=12.2 Hz, 1H), 3.50-3.15 (br m, 4H), 3.07 (s, 3H), 3.01-2.92 (br m, 4H), 2.77 (dt, J=5.3, 15.9 Hz, 1H), 2.14-2.08 (m, 1H), 1.96-1.74 (br m, 3H). (ES MS M+1=505.3)

Examples 14-15

The compounds in the following table were prepared in accordance with the procedure set forth in Example 13 using the appropriate amine in place of dimethylamine.

| Example | Compound | Data |
|---|---|---|
| 14 | 2-[11-(3-Chloro-4-fluorobenzyl)-9-hydroxy-1,8,10-trioxo-1,3,4,5,6,8,10,11,12,13-deca-hydro-2H-[1,4]diazocino[2,1-a]-2,6-naphthyridin-2-yl]-N-methylacetamide | ES MS M + 1 = 491.3 |
| 15 | 2-[11-(3-Chloro-4-fluorobenzyl)-9-hydroxy-1,8,10-trioxo-1,3,4,5,6,8,10,11,12,13-deca-hydro-2H-[1,4]diazocino[2,1-a]-2,6-naphthyridin-2-yl]acetamide | HRMS (APCI, M + 1): found 477.1334 |

Example 16

11-(3-Chloro-4-fluorobenzyl)-9-hydroxy-2-(2-morpholin-4-ylethyl)-3,4,5,6,12,13-hexahydro-2H[1,4]diazocino[2,1a]-2,6-naphthyridine-1,8,10(11H)-trione

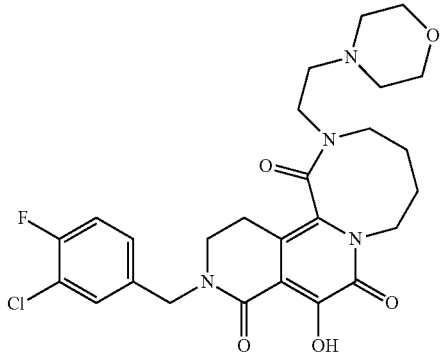

Step 1: 11-(3-Chloro-4-fluorobenzyl)-9-methoxy-2-(2-hydroxyethyl)-3,4,5,6,12,13-hexahydro-2H[1,4]diazocino[2,1-a]-2,6-naphthyridme-1,8,10(11H)-trione A mixture of 11-(3-chloro-4-fluorobenzyl)-9-methoxy-2-[2-(benzyloxy)ethyl]-3,4,5,6,12,13-hexahydro-2H[,4]diazocino[2,1-a]2,6-napthyridine-1,8,10(11H)-trione (0.55 g, 0.97 mmol) and 5% rhodium on carbon (1.10 g) in ethyl acetate (22 mL) was stirred under a balloon of hydrogen at room temperature overnight. The product mixture was filtered through a pad of Celite. The filtrate was concentrated under vacuum to afford the title compound. This material was used in the following reaction without further purification.

$^1$H NMR (400 MHz, CDCl$_3$) δ 7.37 (m, 1H), 7.22-7.19 (m, 1H), 7.10 (t, J=8.6 Hz, 1H), 4.83-4.61 (m, 3 H), 4.19-4.00 (m, 4H), 3.93-3.80 (m, 2H), 3.72-3.55 (m, 1H), 3.49-3.14 (br m, 5H), 2.96-2.81 (m, 1H), 2.48-2.34 (m, 1H), 1.95-1.43 (br signal), 1.21-1.13 (br m, 1H), 0.93-0.84 (br m, 1H). (ES MS M+1=478.1)

Step 2: 11-(3-Chloro-4-fluorobenzyl)-9-methoxy-2-[2-(methansulfonyloxy)ethyl]-3,4,5,6,12,13-hexahydro-2H[1,4]diazocino[2,1-a]-2,6-naphthyridine-1,8,10(11H)-trione To a cold (0° C.) solution of 11-(3-chloro-4-fluorobenzyl)-9-methoxy-2-(2-hydroxyethyl)-3,4,5,6,12,13-hexahydro-2H[1,4]diazocino[2,1-a]-2,6-naphthyridine-1,8,10(11H)-trione (250 mg, 0.52 mmol) and diisopropylethylamine (0.19 mL, 1.05 mmol) in dichloromethane (5 mL), methanesulfonic anhydride (0.1 g, 0.63 mmol) was added. The reaction mixture was allowed to warm up to room temperature and was stirred at room temperature for 2 hour. The product mixture was diluted with dichloromethane and washed with aq ammonium chloride. The organic extract was dried over anhydrous magnesium sulfate, filtered, and concentrated under vacuum to afford the title compound. This material was used in the following reaction without further purification. (ES MS M+1=556.3)

Step 3: 11-(3-Chloro-4-fluorobenzyl)-9-methoxy-2-(2-morpholin-4-ylethyl)-3,4,5,6,12,13-hexahydro-2H[1,4]diazocmo[2,1-a]2,6-naphthyridine-1,8,10(11H)-trione A mixture of 11-(3-chloro-4-fluorobenzyl)-9-methoxy-2-(2-methane-sulfonylethyl)-3,4,5,6,12,13-hexahydro-2H[1,4]diazocino[2,1-a]-2,6-naphthyridine-1,8,10 (11H)-trione (97 mg, 0.17 mmol), morpholine (30 mg, 0.35 mmol), and diisopropylethylamine (006 mL, 0.355 mmol) in THF (1.7 mL) was stirred at 40° C. overnight. The product mixture was concentrated under vacuum. The residue was subjected to column chromatography on silica gel eluting with gradient mixture of methanol in dichloromethane. Collection and concentration of appropriate fractions afforded the title compound.

$^1$H NMR (400 MHz, CDCl$_3$) δ 7.37 (dd, J=2.0, 7.0 Hz, 1H), 7.21 (m, 1H), 7.12 (t, J=8.8 Hz, 1H), 4.80 (dd, J=6.2, 1.3.9 Hz, 1H), 4.74 (d, J=15.0 Hz, 1H), 4.62 (d, J=14.8 Hz, 1H), 4.12-4.07 (m, 4H), 3.69-3.64 (m, 4H), 3.45-3.30 (m, 5H), 3.20-3.13 (m, 1H), 2.90-2.83 (m, 1H), 2.66-2.42 (m, 7H), 2.08 (br m, 1H), 1.91-1.72 (br m, 3H). (ES MS M+1=547.4)

Step 4: 11-(3-Chloro-4-fluorobenzyl)-9-hydroxy-2-(2-morpholin-4-ylethyl)-3,4,5,6,12,13-hexahydro-2H[1,4]diazocino[2,1-a]-2,6-naphthyridine-1,8,10 (11H)-trione A mixture of 11-(3-chloro-4-fluorobenzyl)-9-methoxy-2-(2-morpholin-4-ylethyl)-3,4,5,6,12,13-hexahydro-2H[1,4]diazocino[2,1-a]-2,6-naphthyridine-1,8,10(11H)-trione (30 mg, 0.06 mmol) and 33% hydrogen bromide in acetic acid (0.4 mL) in dioxane (2 mL) was stirred at room temperature for 30 minutes. The product mixture was concentrated under vacuum. The residue was subjected to reverse phase column chromatography on C-18 stationary phase eluted with a 95-5% water-acetonitrile gradient. Collection and lyophilization of appropriate fractions afforded the title compound.

$^1$H NMR (400 MHz, CDCl$_3$) δ 13.3 (s, 1H), 7.35 (dd, J=2.0, 7.0 Hz, 1H), 7.22-7.17 (m, 1H), 7.13 (t, J=8.7 Hz, 1H), 4.84-4.76 (m, 1H), 4.67 (app q, J=14.5 Hz, 2H), 4.43-4.36 (m, 1H), 4.02-2.85 (br signal, 17H), 2.66-2.60 (m, 1H), 2.11-2.01 (br m, 1H), 1.94 (br m, 1H), 1.78-1.69 (br m, 2H). (ES MS M+1=533.3)

Examples 17-22

The compounds in the following table were prepared in accordance with the procedure set forth in Example 16 using the appropriate amines or sodium alkoxide in place of morpholine in Examples 17-19 and 22. Acetylation and methanesulfonylation of the intermediate leading to the preparation of 19 provided Examples 20 and 21.

| Example | Compound | Data |
|---|---|---|
| 17 | 11-(3-Chloro-4-fluorobenzyl)-9-hydroxy-2-(2-pyrrolidinyl-1-ylethyl)-3,4,5,6,12,13-hexahydro-2H[1,4]diazocino[2,1-a]-2,6-naphthyridine-1,8,10(11H)-trione | ES MS M + 1 = 517.3 |

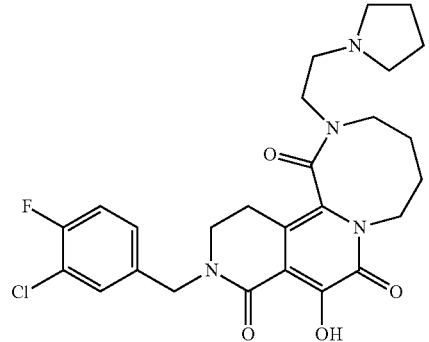

| 18 | 11-(3-Chloro-4-fluorobenzyl)-9-hydroxy-2-(2-piperidinyl-1-ylethyl)-3,4,5,6,12,13-hexahydro-2H[1,4]diazocino[2,1-a]-2,6-naphthyridine-1,8,10(11H)-trione | ES MS M + 1 = 531.2 |

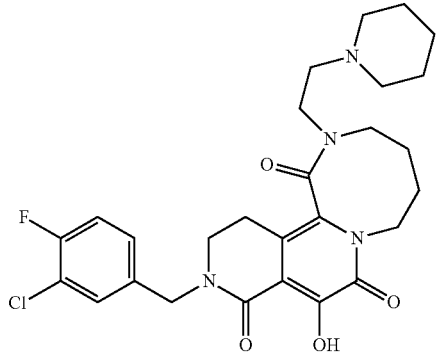

| Example | Compound | Data |
|---|---|---|
| 19 | 11-(3-Chloro-4-fluorobenzyl)-9-hydroxy-2-(2-aminoethyl)-3,4,5,6,12,13-hexahydro-2H[1,4]diazocino[2,1-a]-2,6-naphthyridine-1,8,10(11H)-trione | ES MS M + 1 = 463.2 |
| 20 | 11-(3-Chloro-4-fluorobenzyl)-9-hydroxy-2-[2-(acetylamino)ethyl]-3,4,5,6,12,13-hexahydro-2H[1,4]diazocino[2,1-a]-2,6-naphthyridine-1,8,10(11H)-trione | ES MS M + 1 = 505.3 |
| 21 | 11-(3-Chloro-4-fluorobenzyl)-9-hydroxy-2-[2-(methamesulfonylamino)ethyl]-3,4,5,6,12,13-hexahydro-2H[1,4]diazocino[2,1-a]-2,6-naphthyridine-1,8,10(11H)-trione | ES MS M + 1 = 541.3 |
| 22 | 11-(3-Chloro-4-fluorobenzyl)-9-hydroxy-2-[2-(methoxy)ethyl]-3,4,5,6,12,13-hexahydro-2H[1,4]diazocino[2,1-a]-2,6-naphthyridine-1,8,10(11H)-trione | ES MS M + 1 = 478.2 |

Examples 23-24

11-(3-Chloro-4-fluorobenzyl)-4,9-dihydroxy-2-methyl-3,4,5,6,12,13-hexahydro-2H[1,4]diazocino[2,1-a]-2,6-naphthyridine-1,8,10(11H)-trione

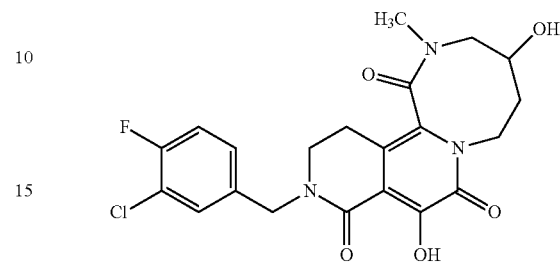

The title compound was prepared in a manner similar to that described in Example 10, steps 6 to 10, substituting N-[2-(benzyloxy)ethyl]-4-{[tert-butyl(dimethyl)-silyl]oxy}butan-1-amine with 4-{[tert-butyl(diphenyl)silyl]oxy}-1-(methylamino)butan-2-ol (Romeril, S. P. et al, *Tet. Lett.* 2003, 7757) in step 6.

Isomer A:
$^1$H NMR (600 MHz, CDCl$_3$) δ 13.09 (s, 1H), 7.35 (dd, J=1.6, 6.7 Hz, 1H), 7.20-7.15 (m, 1H), 7.14-7.09 (m, 1H), 4.78 and 4.71 (d, J=14.2 Hz, second d overlaps with broad multiplet, 2H), 4.60 and 4.55 (d, J=14.9 Hz, 1H), 4.16 and 3.96 (m, 1H), 3.77 and 3.62 (dd, J=10.8, 14.4 Hz, 1H), 3.52-3.36 (m, 2H), 3.34-3.22 (m, 2H), 3.17 (s, 3H), 3.06-2.98 (m, 1H), 2.67-2.48 (m, 2H), 1.94 (m).

Isomer B:
$^1$H NMR (600 MHz, CDCl$_3$) δ 13.13 (s, 1H), 7.35 (d, J=6.6 Hz, 1H), 7.18 (m, 1H), 7.13 (t, J=8.5 Hz, 1H), 4.79 and 4.74 (d, J=15 Hz, 1H), 4.68 (m, 1H), 4.59 and 4.54 (d, J=15 Hz, 1H), 4.16 and 3.96 (br signal, 1H), 3.79 (m), 3.56-3.17 (m), 3.06-2.98 (m, 1H), 2.62-2.54 (m), 2.48 (br m), 2.12 (br m), 1.90 (br m).

(ES MS M+1=450.21)

Example 25

11-(3-Chloro-4-fluorobenzyl)-9-hydroxy-2-methyl-5,6,12,13-tetrahydro-2H[1,4]diazocino[2,1-a]-2,6-naphthyridine-1,4,8,10(3H, 11H)-tetrone

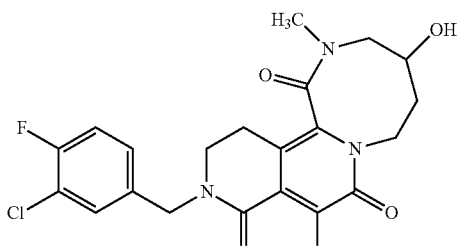

Step 1: 11-(3-Chloro-4-fluorobenzyl)-4-hydroxy-9-methoxy-2-methyl-3,4,5,6,12,13-hexahydro-2H[1,4]diazocino[2,1-a]-2,6-naphthyridine-1,8,10(11H)trione The title compound was prepared in a manner similar to that described in Example 10, steps 6 to 9, substituting N-[2-

(benzyloxy)ethyl]-4-{[tert-butyl(dimethyl)-silyl]oxy}butan-1-amine with 4-{[tert-butyl(diphenyl)silyl]oxy}-1-(methylamino)butan-2-ol (Romeril, S. P. et al, Tet. Lett. 2003, 7757) in step 6.

Early Isomer on Normal Phase Silica (2:1 Mixture of Conformers):

¹H NMR (400 MHz, CDCl₃) δ 7.35 (d, J=6.8 Hz, 1H), 7.17 (m, 1H), 7.10-7.07 (m, 1H), 4.89 and 4.71 (d, J=15 Hz, 1H), 4.67-4.63 (m, 1H), 4.58 and 4.41 (d, J=15 Hz, 1H), 4.14 (br m), 4.08 and 3.96 (s, 3H), 3.90 (m), 3.76-3.70 (m), 3.67-3.52 (m), 3.38 (br s), 3.42-3.21 (m), 3.16 (s), 2.86-2.73 (m, 2H), 2.48-2.33 (m, 2H), 2.06 (m), 1.86-1.77 (m, 1H).

Late Isomer on Normal Phase Silica (5:2 Mixture of Conformers):

¹H NMR (400 MHz, CDCl₃) S 7.36 (d, J=6.8 Hz, 1H), 7.17 (m, 1H), 7.13-7.09 (m, 1H), 4.91 and 4.73 (d, J=14.7 Hz, 1H), 4.70-4.64 (m, 1H), 4.61 and 4.44 (d, J=14.9 Hz, 1H), 4.17 (br s), 4.10 and 3.99 (s, 3H), 3.92 (br m), 3.79-3.74 (m), 3.69-3.54 (m), 3.51 (br s), 3.42-3.24 (m), 3.18 (s), 2.89-2.75 (m, 2H), 2.50-2.38 (m, 2H), 2.08 (br m), 1.88-1.73 (m, 1H).

(ES MS M+1=464.2)

Step 2: 11-(3-Chloro-4-fluorobenzyl)-9-methoxy-2-methyl-5,6,12,13-tetrahydro-2H[1,4]diazocino[2,1-a]-2,6-naphthyridine-1,4,8,10(3H, 11H)-tetrone A mixture of 11-(3-chloro-4-fluorobenzyl)-4-hydroxy-9-methoxy-2-methyl-3,4,5,6,12,13-hexahydro-2H[1,4]diazocino[2,1-a]-2,6-naphthyridine-1,8,10(11H)-trione (50 mg, 0.11 mmol), molecular sieves (4A), N-methylmorpholine N-oxide (19 mg, 0.16 mmol), and tetra-n-propylammonium ruthenium tetroxide in dichloromethane was stirred at room temperature for two hrs. The mixture was filtered, and the filtrate concentrated under vacuum. The residue was subjected to column chromatography on silica gel eluting with 0-15% methanol in dichloromethane gradient. Collection and concentration of appropriate fractions provided the title compound.

¹H NMR (400 MHz, CDCl₃) δ 7.37 (d, J=6.2 Hz, 1H), 7.19 (m, 1H), 7.11 (t, J=8.5 Hz, 1H), 4.80 (d, J=14.1 Hz, 1H), 4.74 (d, J=15.2 Hz, 1H), 4.62 (d, J=14.6 Hz, 1H), 4.15 (s, 3H), 4.10 (d, J=15.4 Hz, 1H), 3.66 (t, J=13.2 Hz, 1H), 3.52 (d, J=15.0 Hz, 1H), 3.45-3.36 (m, 2H), 3.11-3.04 (ra, 4H), 2.94-2.90 (m, 1H), 2.79 (d, J=18.9 Hz, 1H), 2.48-2.45 (m, 1H). (ES MS M+1=462.20)

Step 3: 11-(3-Chloro-4-fluorobenzyl)-9-hydroxy-2-methyl-5,6,12,13-tetrahydro 2H[1,4]diazocino[2,1-a]-2,6-naphthyridine-1,4,8,10(3H, 11H)-tetrone A mixture of 11-(3-chloro-4-fluorobenzyl)-9-methoxy-2-methyl-5,6,12,13-tetrahydro-2H[1,4]diazocino[2,1-a]-2,6-naphthyridine-1,4,8,10(3H, 11H)-tetrone (25 mg, 0.05 mmol) and 33% hydrogen bromide in acetic acid (0.5 mL) in dioxane (1 mL) was stirred at room temperature for 1.5 hour. The product mixture was concentrated under vacuum. The residue was dissolved in DMSO and subjected to reverse phase column chromatography on C-18 stationary phase eluted with a 95-5% water-acetonitrile gradient. Collection and lyophilization of appropriate fractions afforded the title compound.

¹H NMR (400 MHz, CDCl₃) δ 13.47 (s, 1H), 7.38 (d, J=6.0 Hz, 1H), 7.19 (m, 1H), 7.12 (t, J=8.2 Hz, 1H), 5.56 (br s, 1H), 4.94 (br m, 1H), 4.23 (br m, 2H), 4.16-3.98 (m, 2H), 3.60 (br d, J=8.1 Hz, 1H), 3.51 (br d, J=10.2 Hz, 1H), 3.24 (br signal, 1H), 2.89 (s, 3H), 2.59 (br signal, 1H). (ES MS M+1=448.0)

Example 26

11-(3-Chloro-4-fluorobenzyl)-9-hydroxy-2-methyl-4-pyrrolidin-1-yl-3,4,5,6,12,13-hexahydro-2H[1,4]diazocmo[2,1-a]-2,6-naphthyridine-1,8,10(11H)-trione

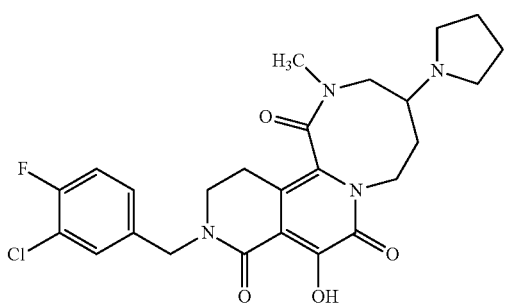

Step 1: 11-(3-Chloro-4-fluorobenzyl)-4-pyrrolidin-1-yl-9-methoxy-2-methyl-3,4,5,6,12,13-hexahydro-2H[1,4]diazocino[2,1-a]-2,6-naphthyridine-1,8,10 (11H)-trione A mixture of 11-(3-chloro-4-fluorobenzyl)-9-methoxy-2-methyl-5,6,12,13-tetrahydro-2H[1,4]diazocino[2,1-a]-2,6-naphthyridine-1,4,8,10(3H, 11H)-tetrone (30 mg, 0.06 mmol), molecular sieves (4A), pyrrolidine (23 mg, 0.32 mmol), and acetic acid (4 mg) in dichloroethane (1 mL) was heated at 80° C. for four hrs. The mixture was cooled to room temperature, treated with sodium borohydride (12 mg, 0.19 mmol), and stirred at room temperature for 30 minutes. The product mixture was diluted with dichloromethane, washed successively with aq sodium carbonate and brine. The organic extract was dried over anhydrous magnesium sulfate, filtered, and concentrated under vacuum to provide the title compound. This material was used in the following step without further purification. ES MS M+1=517.3

Step 2: 11-(3-Chloro-4-fluorobenzyl)-9-hydroxy-2-methyl-5,6,12,13-tetrahydro-2H[1,4]diazocino[2,1-a]-2,6-naphthyridine-1,4,8,10(3H, 11H)-tetrone A mixture of 11-(3-chloro-4-fluorobenzyl)-9-hydroxy-2-methyl-4-pyrrolidin-1-yl-3,4,5,6,12,13-hexahydro-2H[1,4]diazocino[2,1-a]-2,6-naphthyridine-1,8,10(11H)-trione (40 mg, 0.08 mmol) and 33% hydrogen bromide in acetic acid (0.5 mL) in dioxane (1 mL) was stirred at room temperature for 1.5 hour. The product mixture was concentrated under vacuum. The residue was dissolved in DMSO and subjected to reverse phase column chromatography on C18 stationary phase eluted with a 95-5% water-acetonitrile gradient. Collection and Iyophilization of appropriate fractions afforded the title compound.

¹H NMR (400 MHz, CDCl₃) δ 7.36 (d, J=7.1 Hz, 1H), 7.17 (m, 1H), 7.13 (t, J=8.4 Hz, 1H), 4.84 (m, 1H), 4.70 (d, J=14.9 Hz, 1H), 4.63 (d, J=15.1 Hz, 1H), 3.83 (m, 1H), 3.74 (m, 2H), 3.58 (dd, J=10 Hz, 1H), 3.48-3.43 (m, 4H), 3.14 (s, 2H), 3.05-2.94 (br m, 2H), 2.63-2.58 (m, 1H), 2.40 (m, 1H), 2.29-2.24 (m, 1H), 2.07 (br m, 3H). (ES MS M+1=503.2)

Example 27

11-(3-Chloro-4-fluorobenzyl)-9-hydroxy-2-methyl-4-morpholin-4-yl-3,4,5,6,12,13-hexahydro-2H[1,4]diazocino[2,1-a]-2,6-naphthyridine-1,8,10(11H)-trione

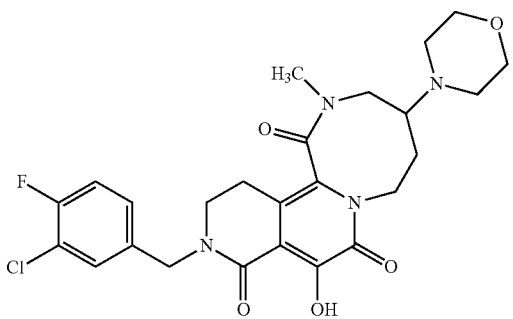

The title compound was prepared in a manner similar to that described in Example 26, substituting pyrrolidine with morpholine. ES MS M+1=518.99.

Examples 28-29

11-(3-Chloro-4-fluorobenzyl)-9-hydroxy-2,6-dimethyl-3,4,5,6,12,13-hexahydro-2H[1,4]diazocino[2,1-a]2,6-naphthyridine-1,8,10(11H)-trione

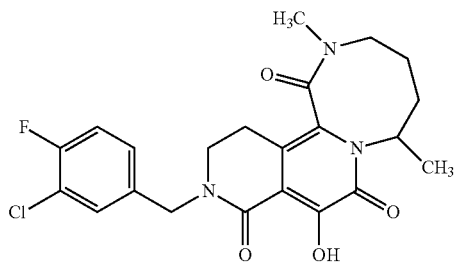

Step 1: 5-(Methylamino)pentan-2-ol

A mixture of γ-valerolactone (5.0 g, 49.9 mmol) and methylamine (75 mL, 2 M in methanol) in methanol (50 mL) was stirred at room temperature overnight. The product mixture was concentrated under vacuum. This intermediate methylamide was concentrated from benzene to remove residual methanol and was used in the following step without further purification. To a cold (0° C.) solution of the above amide (2.0 g, 15.3 mmol) in anhydrous THF, a solution of lithium aluminum hydride (15.2 mL, 2M) in THF was added. The reaction mixture was stirred at room temperature for 30 minutes, and heated at 65° C. overnight. The product mixture was cooled to 0° C. and treated successively with water (1.2 mL), 15% aq sodium hydroxide (1.2 mL), and water (3.6 mL). The resultant suspension was diluted with ether, and filtered with a pad of Celite. The solid filtered was washed with methylene chloride. The organic filtrates were combined and concentrated under vacuum to provide the title compound.

Step 2: 11-(3-Chloro-4-fluorobenzyl)-9-hydroxy-2,6-dimethyl-3,4,5,6,12,13-hexahydro-2H[1,4]diazocino[2,1-a]2,6-naphthyridine-1,8,10(11H)-trione The title compounds were prepared in a manner similar to that described in Example 10, steps 5 to 10, substituting N-[2-(benzyloxy)ethyl]-4-{[tert-butyl(dimethyl)-silyl]oxy}butan-1-amine with 5-(methylamino)pentan-2-ol, and tert-butyldimethylsily chloride with tert-butyldiphenylsily chloride in step 5. Two sets of enantiomeric mixtures (atropisomeric at the exocyclic amide moiety and enantiomeric at the 6-methyl position) were obtained with reverse phase HPLC on C18 stationary phase after hydrogen bromide deprotection in step 10.

Early Isomer on Reverse Phase:
$^1$H NMR (400 MHz, CDCl$_3$) δ 7.34 (d, J=6.3 Hz, 1H), 7.18 (br signal, 1H), 7.13 (t, J=8.6 Hz, 1H), 4.78 (d, J=14.7 Hz, 1H), 4.55 (d, J=14.7 Hz, 1H), 3.49-2.97 (m), 3.10 (s, 3H), 2.59-2.55 (m, 1H), 2.03 (br signal), 1.74 (br signal), 1.36 (d, J=7.1 Hz, 3H). (ES MS exact mass M+1=448.1466)

Late Isomer on Reverse Phase:
$^1$H NMR (400 MHz, CDCl$_3$) δ 7.34 (d, J=6.5 Hz, 1H), 7.18 (br signal, 1H), 7.13 (t, J=8.6 Hz, 1H), 4.78 (d, J=14.7 Hz, 1H), 4.55 (d, J=14.7 Hz, 1H), 4.05 (br t, J=6.6 Hz, 1H), 3.49-2.57 (m), 3.11 (s, 3H), 1.81 (br signal), 1.72 (d, J=6.6 Hz, 3H). (ES MS exact mass M+1=448.1457)

Examples 30-36

The compounds in the following table were prepared in accordance with the procedures set forth in Examples 11 and 29 using the appropriate aminoalcohol in place of 5-(methylamino)pentan-2-ol in Example 29. The amino heterocycles were incorporated in the manner described in Examples 16,

| Example | Compound |
| --- | --- |
| 30 & 31 | 11-(3-Chloro-4-fluorobenzyl)-9-hydroxy-2-(2-hydroxyethyl)-6-methyl-3,4,5,6,12,13-hexahydro-2H[1,4]diazocino[2,1-a]-2,6-naphthyridine-1,8,10(11H)-trione 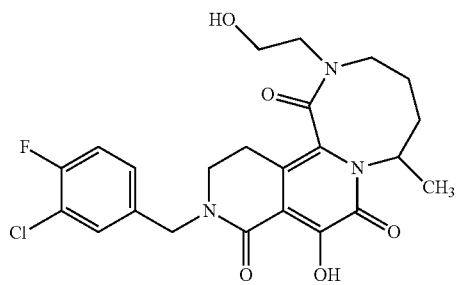 Early isomer on reverse phase: $^1$H NMR (400 MHz, CDCl$_3$) δ 7.35 (dd, J = 6.8, 1.8 Hz, 1H), 7.198 (br signal, 1H), 7.13 (t, J = 8.6 Hz, 1H), 5.72 (m, 1H), 4.77 (d, J = 14.6 Hz, 1H), 4.54 (d, J = 14.6 Hz, 1H), 4.18 (m, 1H), 3.92-3.78 (m, 2H), 3.50-2.92 (m), 2.55 (m, 1H), 2.01-1.75 (br signals), 1.34 (d, J = 7.2 Hz, 3H). (ES MS exact mass M + 1 = 478.1548) Late isomer on reverse phase: $^1$H NMR (400 MHz, CDCl$_3$) δ 7.35 (dd, J = 6.8, 1.6 Hz, 1H), 7.19 (br signal, 1H), 7.12 (t, J = 8.6 Hz, 1H), 4.78 (d, J = 14.6 Hz, 1H), 4.54 (d, J = 14.6 Hz, 1H), 4.18-4.06 (m, 2H), 4.04-3.78 (m, 2H), 3.51-3.00 (m), 2.78-2.56 (m), 1.83-1.77 (br signals), 1.71 (d, J = 6.7 Hz, 3H).. (ES MS exact mass M + 1 = 478.1551) |

-continued

| Example | Compound |
|---|---|
| 32 | 11-(3-Chloro-4-fluorobenzyl)-9-hydroxy-2-(2-morpholin-4-ylethyl)-6-methyl-3,4,5,6,12,13-hexahydro-2H[1,4]diazocino[2,1-a]-2,6-naphthyridine-1,8,10(11H)-trione |

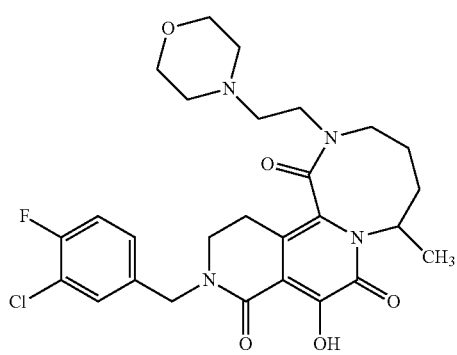

(ES MS M + 1 = 547.2)

| 33 | 11-(3-Chloro-4-fluorobenzyl)-9-hydroxy-2-(2-piperidinyl-1-ylethyl)-6-methyl-3,4,5,6,12,13-hexahydro-2H[1,4]diazocino[2,1-a]-2,6-naphthyridine-1,8,10(11H)-trione |

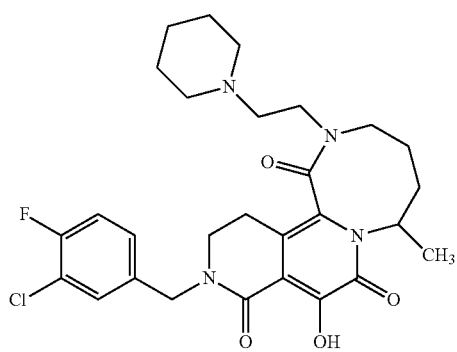

(ES MS M + 1 = 545.2)

| 34 | 11-(3-Chloro-4-fluorobenzyl)-9-hydroxy-2-(2-pyrrolidinyl-1-ylethyl)-6-methyl-3,4,5,6,12,13-hexahydro-2H[1,4]diazocino[2,1-a]-2,6-naphthyridine-1,8,10(11H)-trione |

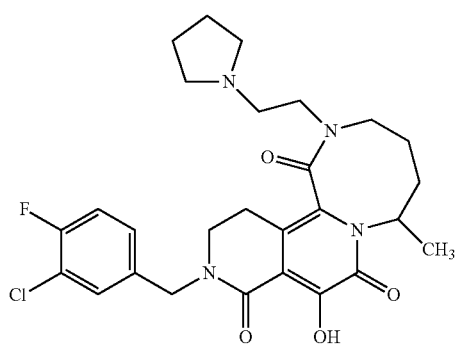

-continued

| Example | Compound |
|---|---|
| | (ES MS M + 1 = 531.2) |
| 35 | 11-(3-Chloro-4-fluorobenzyl)-9-hydroxy-2-[2-(1H-pyrazol-1-yl)ethyl]-6-methyl-3,4,5,6,12,13-hexahydro-2H[1,4]diazocino[2,1-a]-2,6-naphthyridine-1,8,10(11H)-trione |

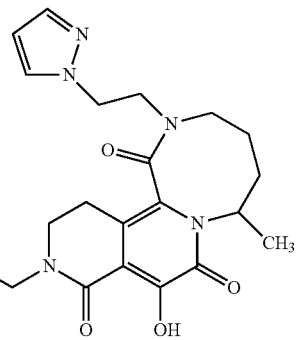

| | (ES MS M + 1 = 528.2) |
| 36 | 11-(3-Chloro-4-fluorobenzyl)-9-hydroxy-2-[2-(1H-imidazol-1-yl)ethyl]-6-methyl-3,4,5,6,12,13-hexahydro-2H[1,4]diazocino[2,1-a]-2,6-naphthyridine-1,8,10(11H)-trione |

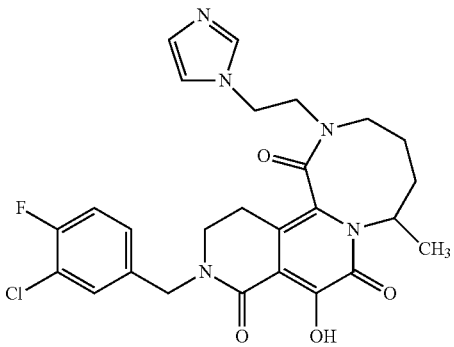

(ES MS M + 1 = 528.2)

Example 37

11(3-Chloro-4-fluorobenzyl)-5,9-dihydroxy-2-methyl-3,4,5,6,12,13-hexahydro-2H[1,4]diazocino[2,1-a]-2,6-naphthyridine-1,8,10(11H)-trione

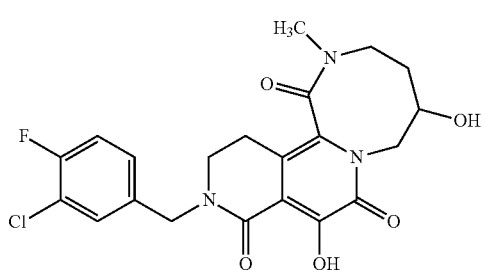

The title compound was prepared in a manner similar to that described in Example 10, steps 6 to 10, substituting N-[2-(benzyloxy)ethyl]-4-{[tert-butyl(dimethyl)-silyl]oxy}butan-1-amine with N-methyl-3-benzyloxy-4-hydroxybutan-1-amine in step 6.

¹H NMR (400 MHz, CDCl₃) δ 7.34 (d, J=6.8 Hz, 1H), 7.18 (m, 1H), 7.12 (t, J=8.4 Hz, 1H), 5.30 (s), 4.78 (d, J=14.7 Hz, 1H), 4.71 (br d, 1H), 4.54 (d, J=3.4.7 Hz, 1H), 4.08 (br signal, 1H), 3.54-3.34 (m) 3.20-2.98 (m), 3.13 (s, 3H). (ES MS M+1=450.2)

Example 38

(4R/S)-11-(3-Chloro-4-fluorobenzyl)-4,9-dihydroxy-2,5,5-trimethyl-3,4,5,6,12,13-hexahydro-2H[1,4]diazocino[2,1-a]-2,6-naphthyridine-1,8,10(11H)-trione

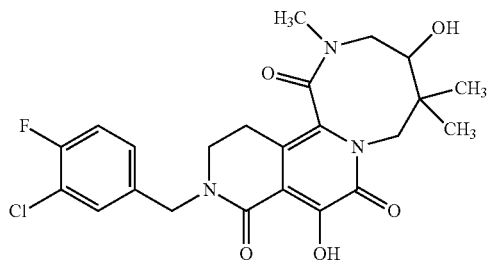

Step 1: (3R)-3-(Benzyloxy)-4,4-dimethyldihydrofuran-2(3H)-one

A mixture of D(−)-pantolactone (20.0 g, 153.7 mmol) and sodium hydride (4.4 g, 184.4 mmol) in anhydrous THF was stirred under an atmosphere of nitrogen at room temperature for 1 hour. The resultant mixture was treated with benzyl bromide (31.5 g, 184.4 mmol) and stirred at room temperature overnight. The product mixture was treated with water and diluted with dichloromethane. The organic extract was washed with brine, dried over anhydrous magnesium sulfate, filtered, and concentrated under vacuum. The residue was subjected to purification on silica gel eluting with 0-5% methanol in dichloromethane gradient. Collection and concentration of appropriate fractions provided the title compound.

¹H NMR (400 MHz, CDCl₃) δ 7.39-7.29 (m, 5H), 5.03 (d, J=12.1 Hz, 1H), 4.75 (d, J=12.1 Hz, 1H), 4.00 (d, J=8.8 Hz, 1H), 3.86 (d, J=8.8 Hz, 1H), 3.74 (s, 1H), 1.14 (s, 3H), 1.10 (s, 3H).

Step 2: (3R)-3-(Benzyloxy)-2,2-dimethyl-4-(methylamino)butan-1-ol

The title compounds were prepared in a manner similar to that described in Examples 28-29, step 1, substituting γ-valerolactone with (3R)-3-(benzyloxy)-4,4-dimethyldihydrofuran-2(3H)-one.

¹H NMR (400 MHz, CDCl₃) δ 7.41-7.32 (m, 5H), 6.63 (br s, 1H), 4.55 (d, J=11.4 Hz, 1H), 4.47 (d, J=11.4 Hz, 1H), 3.79 (s, 1H), 3.48 (s, 1H), 3.43 (d, J=11.8 Hz, 1H), 3.37 (d, J=11.8 Hz, 1H), 2.84 (d, J=5.0 Hz, 3H), 1.06 (s, 3H), 0.85 (s, 3H).

Step 3: (4R)-11-(3-Chloro-4-fluorobenzyl)-4,9-dihydroxy-2,5,5-trimethyl-3,4,5,6,12,13-hexahydro-2H[1,4]diazocino[2,1-a]-2,6-naphthyridine-1,8,10(11H)-trione The title compound was prepared in a manner similar to that described in Example 10, steps 6, 8 to 10, substituting N-[2-(benzyloxy)ethyl]-4-{[tert-butyl(dimethyl)-silyl]oxy}butan-1-amine with (3R)-3-(benzyloxy)-2,2-dimethyl-4-(methylamino)butan-1-ol in step 6.

¹H NMR (400 MHz, CDCl₃) δ 7.4 (dd, J=1.6, 5.4 Hz, 1H), 7.2 (m, 1H), 7.13 (t, J=8.4 Hz, 1H), 4.84 (d, J=14.6 Hz, 1H), 4.75 (d, J=14.8 Hz, 1H), 4.58 (d, J=14.8 Hz, 1H), 3.71 (dd, J=15.0, 9.7 Hz, 1H), 3.44 (m), 3.19 (s, 3H), 3.19 (m), 3.03 (d, J=15.0 Hz, 1H), 2.94 (m, 1H), 2.54 (m, 1H), 1.22 (s, 3H), 0.93 (s, 3H). (ES MS M+1=478.2)

Examples 39-44

The compounds in the following table were prepared in accordance with the procedure set forth in Example 38 using the appropriate lactone in place of D(−)-pantolactone.

| Example | Compound | Data |
|---|---|---|
| 39 | (4-R/S)-11-(3-Chloro-4-fluorobenzyl)-4,9-dihydroxy-2,5,5-trimethyl-3,4,5,6,12,13-hexahydro-2H[1,4]diazocino[2,1-a]-2,6-naphthyridine-1,8,10(11H)-trione | (ES MS M + 1 = 478.2) |

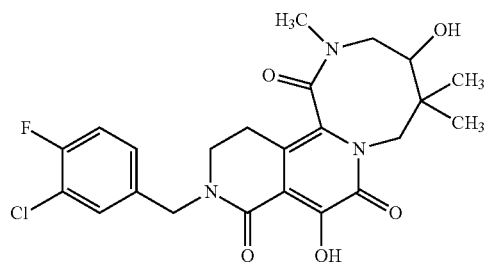

| Example | Compound | Data |
|---|---|---|
| 40 & 41 | L-(−)-pantolactone<br>(4R/S)-11-(3-Chloro-4-fluorobenzyl)-4,9-dihydroxy-2,5,5-trimethyl-3,4,5,6,12,13-hexahydro-2H[1,4]diazocino[2,1-a]-2,6-naphthyridine-1,8,10(11H)-trione | (ES MS M + 1 = 478.2) |

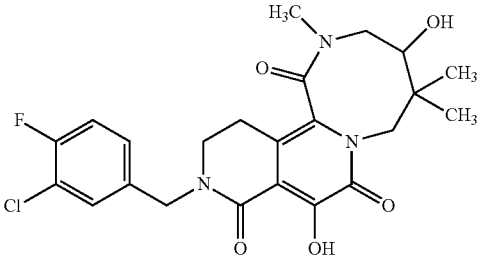

| | | |
|---|---|---|
| 42 | (racemic D/L pantoyl lactone<br>(4R/S)-11-(4-Fluorobenzyl)-4,9-dihydroxy-2,5,5-trimethyl-3,4,5,6,12,13-hexahydro-2H[1,4]diazocino[2,1-a]-2,6-naphthyridine-1,8,10(11H)-trione | (ES MS M + 1 = 448.2) |

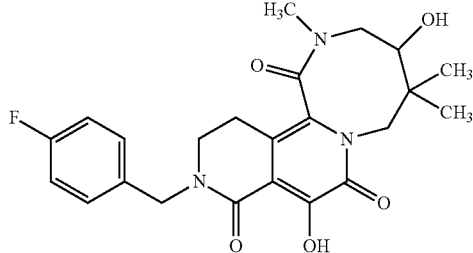

| | | |
|---|---|---|
| 43 | (4R,6S)-11-(3-Chloro-4-fluorobenzyl)-4,9-dihydroxy-2,6-dimethyl-3,4,5,6,12,13-hexahydro-2H[1,4]diazocino[2,1-a]-2,6-naphthyridine-1,8,10(11H)-trione | (ES MS M + 1 = 464.1) |

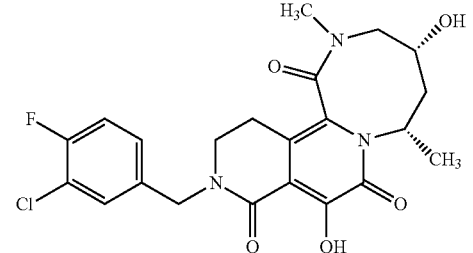

| | | |
|---|---|---|
| 44 | (4S,6S)-11-(3-Chloro-4-fluorobenzyl)-4,9-dihydroxy-2,6-dimethyl-3,4,5,6,12,13-hexahydro-2H[1,4]diazocino[2,1-a]-2,6-naphthyridine-1,8,10(11H)-trione | (ES MS M + 1 = 464.1) |

Example 45

11-(3-Chloro-4-fluorobenzyl)-9-hydroxy-2,4,4-trimethyl-3,4,5,6,12,13-hexahydro-2H[1,4]diazocino[2,1-a]-2,6-naphthyridine-1,8,10(11H)trione

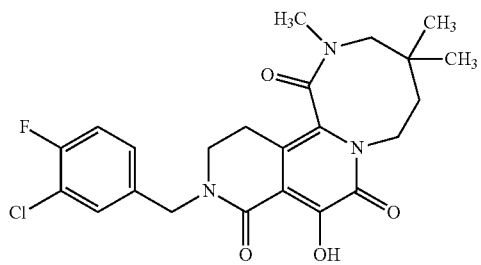

The title compound was prepared in a manner similar to that described in Example 10, steps 6 to 10, substituting N-[2-(benzyloxy)ethyl]-4-{[tert-butyl(dimethyl)-silyl]oxy}butan-1-amine with 4-{[tert-butyl(diphenyl)-silyl]oxy}-N,2,2-trimethylbutan-1-amine in step 6.

$^1$H NMR (400 MHz, CDCl$_3$) δ 7.35 (dd, J=1.6, 6.8 Hz, 1H), 7.2 (m, 1H), 7.13 (t, J=8.6 Hz, 1H), 4.79 (d, J=14.9 Hz, 1H), 4.70 (m, 4H), 4.54 (d, J=14.9 Hz, 1H), 3.53 (m), 3.18 (s, 3H), 3.05-2.93 (m), 2.84 (d, J=15.2 Hz, 1H), 2.56-2.48 (m), 1.85-1.66 (m), 1.12 (s, 3H), 0.89 (s, 3H). (ES MS exact mass M=462.1600)

Example 46

11-(3-Chloro-4-fluorobenzyl)-9-hydroxy-2,4-dimethyl-3,4,5,6,12,13-hexahydro-2H[1,4]diazocino[2,1-a]-2,6-naphthyridine-1,8,10(11H)-trione

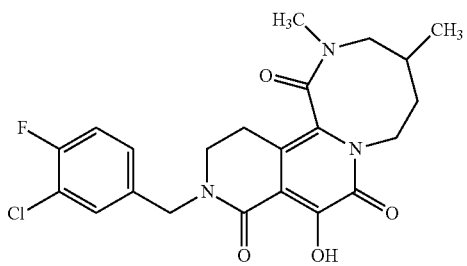

The title compounds were prepared in a manner similar to that described in Examples 28-29, substituting γ-valerolactone with α-methyl-γ-butyrolactone.

$^1$H NMR (400 MHz, CDCl$_3$) δ 7.36-7.30 (m, 1H), 7.21-7.18 (br signal, 1H), 7.13 (t, J=8.6 Hz, 1H), 4.80 (d, J=14.6 Hz, 1H), 4.80 (m), 4.53 (d, J=14.6 Hz, 1H), 3.50-2.53 (m), 3.11 (s, 3H), 2.18-1.53 (m), 0.90 (d, J=7.0 Hz, 3H). (ES-MS M+1=448.17)

Example 47

(6R)-11-(3-Chloro-4-fluorobenzyl)-9-hydroxy-6-(hydroxymethyl)-2-methyl-3,4,5,6,12,13-hexahydro-2H-[1,4]diazocino[2,1-a]-2,6-naphthyridine-1,8,10(11H)-trione

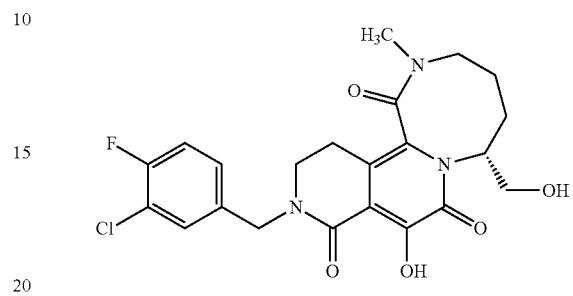

Step 1: (2S)-1-(Benzyloxy)-5-(methylamino)pentan-2-ol

The title compound was prepared in a manner similar to that described in Examples 28-29, step 1, substituting γ-valerolactone with (5S)-5-[(benzyloxy)methyl]dihydrofuran-2 (3H)-one. (ES MS M+1=224.0).

Step 2: 6(3-Chloro-4-fluorobenzyl)-N-[(4S)-4,5-dihydroxypentyl]-4-methoxy-N-methyl-3,5-dioxo-2,3,5,6,7,8-hexahydro-2,6-naphthyridine-1-carboxamide The title compound was prepared in a manner similar to that described in Example 10, step 6, substituting N-[2-(benzyloxy)-ethyl]-4-{[tert-butyl(dimethyl)silyl]oxy}butan-1-amine with (2S)-1-(benzyloxy)-5-(methylamino)pentan-2-ol. (ES MS M+1=586.33)

Step 3: (6R)-6-[(Benzyloxy)methyl]-11-(3-chloro-4-fluorobenzyl)-9-methoxy-2-methyl-3,4,5,6,12,13-hexahydro-2H-[1,4]diazocino[2,1-a]-2,6-naphthyridine-1,8,10(11H)-trione The title compound was prepared in a manner similar to that described in Example 10, steps 8 and 9, substituting N-[2-(benzyloxy)ethyl]-N-(4-hydroxybutyl)-6-(3-chloro-4-fluorobenzyl)-4-methoxy-3,5-dioxo-2,3,5,6,7,8-hexahydro-2,6-naphthyridine-1-carboxamide with 6-(3-chloro-4-fluorobenzyl)-N-[(4S)-4,5-dihydroxypentyl]-4-methoxy-N-methyl-3,5-diox-2,3,5,6,7,8-hexahydro-2,6-naphthyridine-1-carboxamide in step 8. (ES MS M+1=568.3)

Step 4: (6R)-11-(3-Chloro-4-fluorobenzyl)-9-hydroxy-6-(hydroxymethyl)-2-methyl-3,4,5,6,12,13-hexahydro-2H-[1,4]diazocino[2,1-a]-2,6-naphthyridine-1,8,10(11H)-trione A solution of (6R)-6-[(benzyloxy)methyl]-11-(3-chloro-4-fluorobenzyl)-9-methoxy-2-methyl-3,4,5,6,12,13-hexahydro-2H-[1,4]diazocino[2,1-a]-2,6-napthyridine-1,8,10 (11H)-trione (167 mg, 0.29 mmol) in dichloromethane (2.9 mL) was cooled to 0° C. and treated with boron tribromide (295 mg, 1.18 mmol). The cooling bath was removed and the mixture stirred at room temperature for 30 minutes. The reaction was quenched by the addition of MeOH followed by 1N aqueous HCl. The mixture was diluted with dichloromethane and washed with water. The organic layer was dried over anhydrous magnesium sulfate, filtered and concentrated under vacuum. The residue was subjected to reverse phase column chromatography on C-18 stationary phase eluted with a 95-5% water-acetonitrile gradient. Collection and concentration of appropriate fractions afforded the title compound.

$^1$H NMR (400 MHz, CDCl$_3$) δ 13.15 (br s, 1H), 7.35 (d, J=6.8 Hz, 1H), 7.19 (m, 1H), 7.13 (t, J=8.5 Hz, 1H), 4.80 (d, J=14.6 Hz, 1H), 4.54 (d, J=14.6 Hz, 1H), 4.40-4.10 (br signal), 4.04-3.92 (m, 3H), 3.8-3.6 (br m), 3.54-3.47 (m), 3.41-3.31 (m), 3.22-3.16 (m), 3.10 (s, 3H), 3.06-2.99 (m, 1H), 2.61-2.54 (m, 1H), 2.25-2.15 (m, 2H), 1.85-1.80 (m, 2H), 1.26-1.14 (m). (ES MS M+1=464.3)

Example 48

(6R) 11-(4-Fluorobenzyl)-9-hydroxy-6-(hydroxymethyl)-2-methyl-3,4,5,6,12,13-hexahydro-2H-[1,4]diazocino[2,1-a]2,6-naphthyridine-1,8,10(11H)-trione

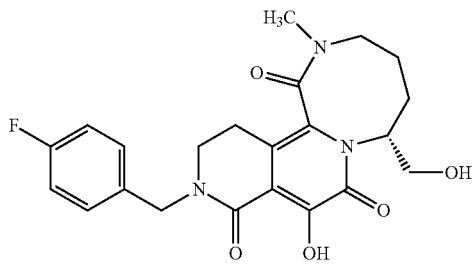

A mixture of (6R)-11-(3-chloro-4-fluorobenzyl)-9-hydroxy-6-(hydroxymethyl)-2-methyl-3,4,5,6,32,13-hexahydro-2H-[1,4]diazocino[2,1-a]-2,6-naphthyridine-1,8,10 (11H)-trione (109 mg, 0.24 mmol), 20% Pd(OH)2 on carbon (40 mg) and diisopropylethylamine (0.1 mL) in EtOH (2.4 mL) was stirred under hydrogen atmosphere for 20 hours. The reaction mixture was filtered through a Celite pad and the filtrate concentrated under vacuum to afford the title compound.

$^1$H NMR (400 MHz, CDCl$_3$) δ 7.30-7.28 (m), 7.04 (t, J=8.5 Hz, 2H), 4.80 (d, J=14.6 Hz, 1H), 4.59 (d, J=14.6 Hz, 1H), 4.06-4.04 (m, 2H), 3.95-3.92 (m, 1H), 3.53-3.45 (m, 1H), 3.40-3.28 (m, 2H), 3.22-3.17 (m, 1H), 3.04-2.97 (m, 1H), 2.59-2.52 (m, 1H), 2.23-2.21 (m, 2H), 1.81 (m, 2H). (ES MS M+1=430.2)

Example 49

(6S)-11-(3-Chloro-4-fluorobenzyl)-9-hydroxy-6-(hydroxymethyl)-2-methyl-3,4,5,6,12,13-hexahydro-2H-[1,4]diazocino[2,1-a]-2,6-naphthyridine-1,8,10 (11H)-trione

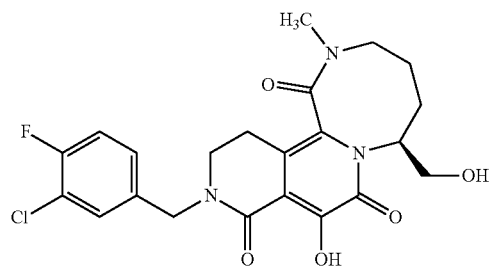

The title compound was prepared in a manner similar to that described in Example 46 and was isolated as a mixture of atropisomers. Further purification by reverse phase column chromatography on a C18 column (gradient elution with 70% H$_2$O—CH$_3$CN to 65% H$_2$O—CH$_3$CN over 30 minutes, then isocratic elution with 65% H$_2$O—CH$_3$CN for 10 minutes) afforded the title compound as the less polar atropisomer.

$^1$H NMR (400 MHz, CDCl$_3$) δ 13.11 (s, 1H), 7.36-7.34 (m, 1H), 7.21-7.10 (m, 2H), 4.78 (d, J=14.7 Hz, 1H), 4.55 (d, J=14.7 Hz, 1H), 4.01-3.90 (m, 3H), 3.54-3.42 (m, 1H), 3.40-3.30 (m, 2H), 3.21-3.17 (m, 1H), 3.09 (s, 3H), 3.06-3.00 (m, 1H), 2.60-2.53 (m, 1H), 2.23-2.15 (m, 2H), 1.84-1.80 (m, 2H). HRMS (ES M+1). found 464.1400; calculated 464.1383.

The more polar isomer was also isolated from the mixture:

$^1$H NMR (400 MHz, CDCl$_3$) δ 13.09 (s, 1H), 7.36 (dd, J=1.9, 6.8 Hz, 1H), 7.22-7.10 (m, 2H), 5.68 (br s, 1H), 4.82 (d, J=14.8 Hz, 1H), 4.52 (d, J=14.8 Hz, 1H), 3.72-3.66 (m, 2H), 3.53-3.46 (m, 1H), 3.38-3.32 (m, 2H), 3.16-2.82 (m, 5H), 2.53-2.45 (m, 1H), 2.05-2.01 (m, 2H), 1.78-1.69 (m, 2H). HRMS (ES M+1). found 464.1402; calculated 464.1383.

Example 50

11-(3-chloro-4-fluorobenzyl)-9-hydroxy-2-methyl-6-methylene-3,4,5,6,12,13-hexahydro-2H-[1,4]diazocino[2,1-a]2,6-naphthyridine-1,8,10(11H)trione

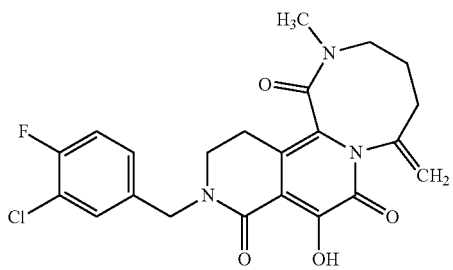

The title compound was generated during the boron tribromide-mediated deprotection of (6S)-6-[(benzyloxy)methyl]-

11-(3-chloro-4-fluorobenzyl)-9-methoxy-2-methyl-3,4,5,6,12,13-hexahydro-2H-[1,4]diazocino[2,2-a]2,6-naphthyridine-1,8,10(11H)-trione following the method described in Example 47, step 4 for deprotection of the corresponding (6R)-isomer, and was isolated by reverse phase column chromatography on C-18 stationary phase eluted with a 95-5% water-acetonitrile gradient.

HRMS (ES M+1). found 446.1264; calculated 446.1277.

Example 51

2-[8-(3-Chloro-4-fluorobenzyl)-6-hydroxy-3,3-dimethyl-2,5,7-trioxo-2,3,7,8,9,10-hexahydroimidazo[2,1-a]-2,6-naphthyridin-1(5H)-yl]-N,N-dimethylacetamide

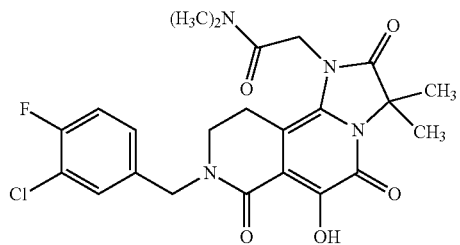

Step 1: tert-Butyl[8-(3-Chloro-4-fluorobenzyl)-6-methoxy-3,3-dimethyl-2,5,7-trioxo-2,3,7,8,9,10-hexahydroimidazo[2,1-a]-2,6-naphthyridin-1 (5H)-yl]acetate A mixture of 8-(3-chloro-4-fluorobenzyl)-6-methoxy-1,8,9,10-tetrahydroimidazo[2,1-a]-2,6-naphthyridine-2,5,6(3H) trione (1.00 g, 2.55 mmol; Example 8, step 5), sodium hydride (112 mg, 60% dispersion; 2.81 mmol), tert-butyl bromoacetate (0.55 g, 2.81 mmol) in anhydrous DMF (10 mL) was stirred at room temperature overnight. The reaction mixture was concentrated under vacuum. The residue was subject to column chromatography on silica gel. Collection and concentration of appropriate fractions provided the required alkylated intermediate. A mixture of the above material (0.49 g, 0.99 mmol), sodium hydride (71 mg, 60% dispersion; 2.96 mmol), iodomethane (0.42 g, 2.96 mmol) in anhydrous DMF (10 mL) was stirred at room temperature overnight. The reaction mixture was concentrated under vacuum. The residue was subject to column chromatography on silica gel. Collection and concentration of appropriate fractions afforded the title compound. ES MS M+1=534.2

Step 2: 2-[8-(3-Chloro-4-fluorobenzyl)-6-hydroxy-3,3-dimethyl-2,5,7-trioxo-2,3,7,8,9,10-hexahydroimidazo[2,1-a]-2,6-naphthyridin-1 (5H)-yl]-N,N-dimethylacetamide A mixture of tert-butyl[8-(3-Chloro-4-fluorobenzyl)-6-methoxy-3,3-dimethyl-2,5,7-trioxo-2,3,7,8,9,10-hexahydroimidazo[2,1-a]-2,6-naphthyridin-1 (5H)-yl]acetate (0.30 g, 0.56 mmol) and hydrogen chloride (2.8 mL, 4 M in dioxane) in dioxane (5 mL) was stirred at room temperature overnight. The reaction mixture was concentrated under vacuum. The residue was triturated with diethyl ether and filtered to provide the title compound. This intermediate acid was used in the following step without further purification. A solution of the acid (40 mg, 0.08 mmol), BOP (48 mg, 0.11 mmol), diisopropylethylamine (12 mg, 0.12 mmol) and dimethylamine (0.04 mL, 2M in THF) in DMF (0.5 mL) was stirred at room temperature overnight. The product mixture was concentrated under vacuum. The residue was subjected to column chromatography on silica gel. Collection and concentration of appropriate fractions afforded the penultimate product. This material (28 mg, 0.06 mmol) was treated with 33% hydrogen bromide in acetic acid (44 mg) in dioxane (1 mL) at room temperature for 1.5 hour. The product mixture was concentrated under vacuum. The residue was dissolved in DMSO and subjected to reverse phase column chromatography on C-18 stationary phase eluted with a 95-5% water-acetonitrile gradient. Collection and lyophilization of appropriate fractions afforded the title compound.

$^1$H NMR (400 MHz, CDCl$_3$) δ 7.33 (br d, J=6.8 Hz, 1H), 7.18 (br signal, 1H), 7.13 (t, J=8.4 Hz, 1H), 4.65 (s, 3H), 4.63 (s, 3H), 3.40 (br signal, 2H), 3.08 (s, 3H), 2.98 (s, 3H), 2.73 (br signal, 2H), 1.84 (s, 6H) (ES MS exact mass M+1=491.1570)

Examples 52-53

The compounds in the following table were prepared in accordance with the procedure set forth in Example 51 using the appropriate amine in place of dimethylamine.

| Example | Compound | Data |
| --- | --- | --- |
| 52 | 2-[8-(3-Chloro-4-fluorobenzyl)-6-hydroxy-3,3-dimethyl-2,5,7-trioxo-2,3,7,8,9,10-hexahydroimidazo[2,1-a]-2,6-naphthyridin-1(5H)-yl]-N-methylacetamide | (ES MS exact mass M + 1 = 477.1343) |

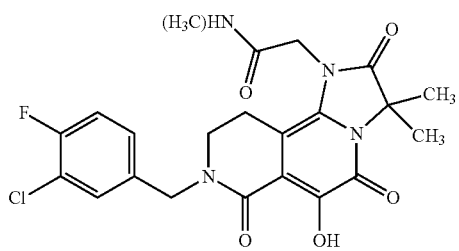

-continued

| Example | Compound | Data |
|---|---|---|
| 53 | 2-[8-(3-Chloro-4-fluorobenzyl)-6-hydroxy-3,3-dimethyl-2,5,7-trioxo-2,3,7,8,9,10-hexahydroimidazo[2,1-a]-2,6-naphthyridin-1(5H)-yl]acetamide | (ES MS exact mass M + 1 = 463.1179) |

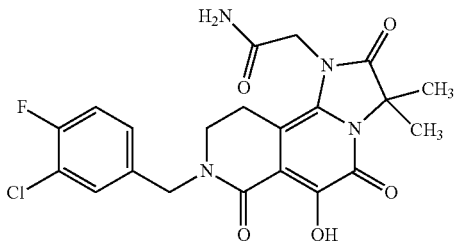

Example 54

8-(3-Chloro-4-fluorobenzyl)-6-hydroxy-1-(2-hydroxyethyl)-3,3-dimethyl-1,8,9,10-tetrahydroimidazo[2,1-a]-2,6-naphthyridine-2,5,7(3H)-trione

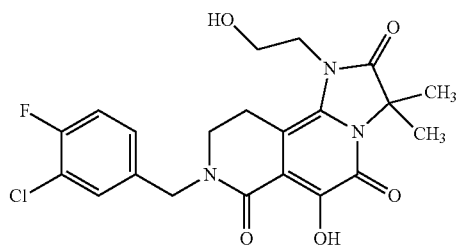

The title compound was prepared in a manner similar to that described in Example 50, substituting tert-butyl bromoacetate with 2-benzyloxyethylbromide in step 1.

$^1$H NMR (400 MHz, CDCl$_3$) δ 7.36 (dd, J=6.8, 1.8 Hz, 1H), 7.20 (br signal, 1H), 7.13 (t, J=8.6 Hz, 1H), 5.30 (s, 1H), 4.68 (s, 2H), 4.02 (t, J=5.5 Hz, 2H), 3.87 (t, J=5.5 Hz, 2H), 3.44 (t, J=6.2 Hz, 2H), 3.04 (t, J=6.2 Hz, 2H), 1.79 (s, 6H) (ES MS exact mass M+1=450.1225)

Examples 55-56

The compounds in the following table were prepared in accordance with the procedure set forth in Example 55 using the appropriate benzyloxyalkyl bromide in place of 2-benzyloxyethylbromide.

| Example | Compound | Data |
|---|---|---|
| 55 | 8-(3-Chloro-4-fluorobenzyl)-6-hydroxy-1-(3-hydroxypropyl)-3,3-dimethyl-1,8,9,10-tetrahydroimidazo[2,1-a]-2,6-naphthyridine-2,5,7(3H)-trione | (ES MS exact mass M + 1 = 464.1408) |

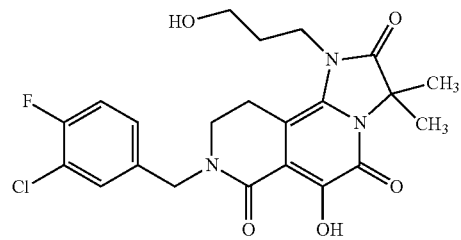

| 56 | 8-(3-Chloro-4-fluorobenzyl)-6-hydroxy-1-(4-hydroxybutyl)-3,3-dimethyl-1,8,9,10-tetrahydroimidazo[2,1-a]-2,6-naphthyridine-2,5,7(3H)-trione | (ES MS exact mass M + 1 = 478.1548) |

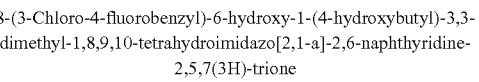

Example 57

8(3-Chloro-4-fluorobenzyl)-6-hydroxy-1-(2-acetyloxyethyl)-3,3-dimethyl-1,8,9,10-tetrahydroimidazo[2,1-a]-2,6-naphthyridine-2,5,7(3H)-trione

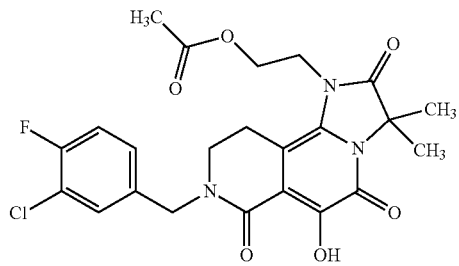

The title compound was prepared in a manner similar to that described in Example 54, except 33% hydrogen bromide in acetic acid was used in the final demethylation step.

$^1$H NMR (400 MHz, CDCl$_3$) δ 7.35 (br d, J=6.8 Hz, 1H), 7.20 (br signal, 1H), 7.14 (t, J=8.4 Hz, 1H), 4.68 (s, 2H), 4.27 (t, J=5.5 Hz, 2H), 4.12 (t, J=5.5 Hz, 2H), 3.49 (t, J=6.2 Hz, 2H), 3.02 (t, J=6.2 Hz, 2H), 2.02 (s, 3H), 1.80 (s, 6H) (ES MS exact mass M+1=492.1342)

Examples 58-60

The compounds in the following table were prepared in accordance with the procedure set forth in Example 57 using the appropriate benzyloxyalkyl bromide in place of 2-benzyloxyethylbromide.

| Example | Compound | Data |
|---|---|---|
| 58 | 8-(3-Chloro-4-fluorobenzyl)-6-hydroxy-1-(3-acetyloxypropyl)-3,3-dimethyl-1,8,9,10-tetrahydroimidazo[2,1-a]-2,6-naphthyridine-2,5,7(3H)-trione | (ES MS exact mass M + 1 = 506.1480) |
| | 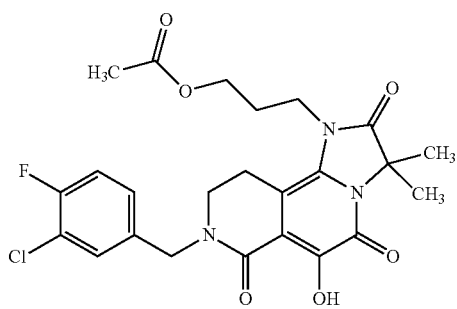 | |
| 59 | 8-(3-Chloro-4-fluorobenzyl)-6-hydroxy-1-(4-acetyloxybutyl)-3,3-dimethyl-1,8,9,10-tetrahydroimidazo[2,1-a]-2,6-naphthyridine-2,5,7(3H)-trione | (ES MS exact mass M + 1 = 520.1645) |
| | 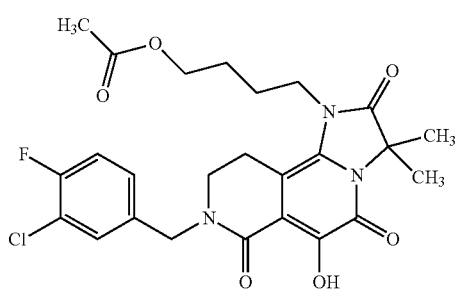 | |
| 60 | 8-(3-Chloro-4-fluorobenzyl)-6-hydroxy-1,3-bis(2-hydroxyethyl)-3-methyl-1,8,9,10-tetrahydroimidazo[2,1-a]-2,6-naphthyridine-2,5,7(3H)-trione | (ES MS exact mass M + 1 = 480.1350) |
| | 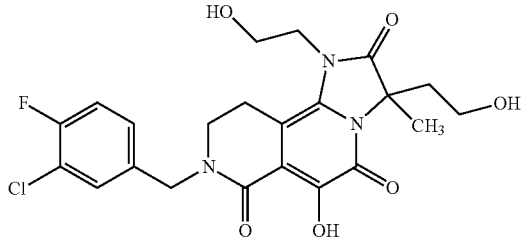 | |

Example 61

11-(3-Chloro-4-fluorobenzyl)-9-hydroxy-3,4,5,6,12,13-hexahydro-[1,4]oxazocino[3,4-a]-2,6-naphthyridine-1,8,10(11H)-trione

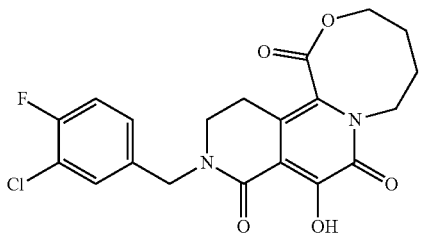

A mixture of 6-(3-chloro-4-fluorobenzyl)-3,4-dihydroxy-N,N-dimethyl-5-oxo-5,6,7,8-tetrahydro-2,6-naphthyridine-1-carboxamide (0.80 g, 2.19 mmol; Example 1, step 9) and magnesium methoxide in methanol (10.6 mL, 6-10% methanol solution available from Aldrich) in DMSO (22 mL) was heated at 60° C. for 30 minutes. Methanol was exhaustively removed under vacuum over 45 minutes. The residual DMSO solution was treated with 1-bromo-4-chlorobutane (3.80 g, 10.50 mmol) and stirred at 60° C. under an atmosphere of nitrogen overnight. The reaction mixture was heated at 100° C. for 3 hrs. The reaction mixture was treated with dilute HCl. The solid precipitated was filtered, dissolved in DMSO, and subjected to reverse phase HPLC purification. Collection and lyophization of appropriate fractions provided the title compound.

$^1$H NMR (400 MHz, CDCl$_3$) δ 13.4 (br s, 1H), 7.38 (dd, J=1.6, 6.6 Hz, 1H), 7.20 (m, 1H), 7.14 (t, J=8.6 Hz, 1H), 4.68 (s, 2H), 4.26 (br signal, 2H), 3.46 (t, J=6.4 Hz, 2H), 2.83 (br signal, 2H), 2.00 (br signal, 4H). (ES MS exact mass M+1=421.0966)

Example 62

10-(3-Chloro-4-fluorobenzyl)-8-hydroxy-4,5,11,12-tetrahydro-3H-[1,4]oxazepino[3,4-a]-2,6-naphthyridine-1,7,9(10H)-trione

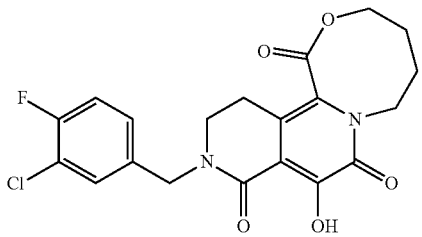

The title compound was prepared in a manner similar to that described in Example 61, substituting 1-bromo-4-chlorobutane with 1-bromo-3-chloropropane.

$^1$H NMR (400 MHz, CDCl$_3$) δ 13.78 (s, 1H), 7.38 (dd, J=2, 7 Hz, 1H), 7.18 (m, 1H), 7.14 (t, J=8.6 Hz, 1H), 4.68 (s, 2H), 4.23 (t, J=6 Hz, 2H), 3.45 (t, J=6 Hz, 2H), 2.97 (t, J=6 Hz, 2H), 2.23 (t, J=6 Hz, 2H). (ES MS exact mass M+1=407.0819)

Example 63

9-(3-Chloro-4-fluorobenzyl)-7-hydroxy-3-(acetyloxymethyl)-3,4,10,11-tetrahydro[1,4]oxazino[3,4-a]-2,6-naphthyridine-1,6,8(9H)-trione

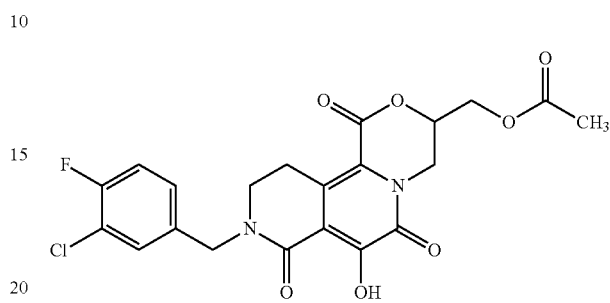

Step 1: Methyl 2-(allyl)-6-(3-chloro-4-fluorobenzyl)-4-hydroxy-3,5-dioxo-2,3,5,6,7,8-hexahydro-2,6-naphthyridine-1-carboxylate A mixture of 6-(3-chloro-4-fluorobenzyl)-3,4-dihydroxy-N,N-dimethyl-5-oxo-5,6,7,8-tetrahydro-2,6-naphthyridine-1-carboxamide (3.99 g, 10.51 mmol; Example 1, step 9) and magnesium methoxide in methanol (52.4 mL, 6-10% methanol solution available from Aldrich) in DMSO (100 mL) was heated at 60° C. for 30 minutes. Methanol was exhaustively removed under vacuum over 45 minutes. The residual DMSO solution was treated with allyl bromide (3.810 g, 31.52 mmol) and stirred at room temperature under an atmosphere of nitrogen for overnight. The reaction mixture was treated dilute hydrochloric acid. The solid precipitated was filtered to provide the title compound. (ES MS M+1=421.2)

Step 2: Methyl 2-(allyl)-6-(3-chloro-4-fluorobenzyl)-4-methoxy-3,5-dioxo-2,3,5,6,7,8-hexahydro-2,6-naphthyridine-1-carboxylate A mixture of methyl 2-(allyl)-6-(3-chloro-4-fluorobenzyl)-4-hydroxy-3,5-dioxo-2,3,5,6,7,8-hexahydro-2,6-naphthyridine-1-carboxylate (6.08 g, 14.92 mmol), cesium carbonate (6.08 g, 18.65 mmol), and iodomethane (2.79 mL, 44.77 mmol) in DMF (20 mL) was heated at 40° C. overnight. The reaction mixture was filtered and concentrated under vacuum. The residue was subjected to column chromatography on silica gel. Collection and concentration of appropriate fractions provided the title compound. (ES MS M+1=435.2)

Step 3: 9-(3-Chloro-4-fluorobenzyl)-3-(hyrdoxymethyl)-7-methoxy-3,4,10,11-tetrahydro[1,4]oxazino[3,4-a]-2,6-naphthyridine-1,6,8(9H)-trione A mixture of methyl 2-(allyl)-6-(3-chloro-4-fluorobenzyl)-4-methoxy-3,5-dioxo-2,3,5,6,7,8-hexahydro-2,6-naphthyridine-1-carboxylate (0.20 g, 0.46 mmol), N-methylmoroholine N-oxide (67 mg, 0.58 mmol), water (0.2 mL), and osmium tetroxide (0.75 mL, 0.08 M in t-butanol) in acetone (1 mL) was stirred at room temperature overnight. The product mixture was concentrated under vacuum. The residue was subjected to column chromatography on silica gel. Collection and concentration of appropriate fractions provided the title compound.
(ES MS M+1=437.2)

Step 4: 9-(3-Chloro-4-fluorobenzyl)-7-hydroxy-3-(acetyloxymethyl)-3,4,10,11-tetrahydro[1,4]oxazino[3,4-a]-2,6-naphthyridine-1,6,8(9H)-trione A mixture of 9(3-chloro-4-fluorobenzyl)-3-(hyrdoxymethyl)-7-methoxy-3,4,10,11-tetrahydro[1,4]oxazino[3,4a]-2,6-naphthyridine-1,6,8(9H)-trione (50 mg, 0.11 mmol) and 33% hydrogen bromide in acetic acid (0.1 g) in acetic acid (1 mL) was stirred at room temperature for 30 minutes. The product mixture was concentrated under vacuum. The residue was dissolved in DMSO and subjected to reverse phase column chromatography on C-18 stationary phase eluted with a 95-5% water-acetonitrile gradient Collection and Iyophilization of appropriate fractions afforded the title compound.

$^1$H NMR (400 MHz, CDCl$_3$) δ 7.60 (1H), 7.42 (1H), 7.38 (1H), 4.86 (1H), 4.71 (2H), 4.68 (1H), 4.34 (2H), 3.82 (1H), 3.50 (2H), 3.20 (2H), 2.07 (3H). (ES MS exact mass M+1=465.0851)

Example 64

9-(3-Chloro-4-fluorobenzyl)-7-hydroxy-3-(hydroxymethyl)-3,4,10,11-tetrahydro[1,4]oxazino[3,4-a]-2,6-naphthyridine-1,6,8(9H)trione

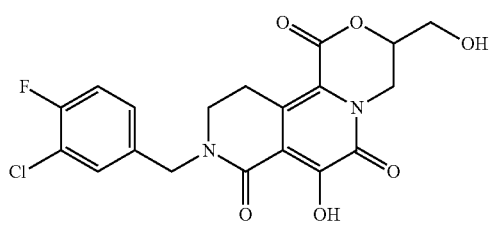

A mixture of 9-(3-chloro-4-fluorobenzyl)-7-hydroxy-3-(acetyloxymethyl)-3,4,10,11-tetrahydro[1,4]oxazino[3,4-a]-2,6-naphthyridine-1,6,8(9H)-trione (46 mg, 0.10 mmol) and 30% sodium methoxide in methanol (39 mg) in dioxane (1.5 mL) was stirred at room temperature for 2 hours. The product mixture was concentrated under vacuum. The residue was dissolved in DMSO and subjected to reverse phase column chromatography on C-18 stationary phase eluted with a 95-5% water-acetonitrile gradient. Collection and Iyophilization of appropriate fractions afforded the title compound.

$^1$H NMR (400 MHz, CDCl$_3$) δ 7.37 (dd, J=6.8, 1.8 Hz, 1H), 7.21 (br signal, 1H), 7.15 (t, J=8.6 Hz, 1H), 4.89 (d, J=14.6 Hz, 1H), 4.69 (s, 2H), 4.03-3.82 (m, 4H), 3.47-3.30 (m, 5H), 2.29 (br s, 3H). (ES MS exact mass M+1=423.0754)

Example 65

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2 to 64 can be similarly prepared.

Example 66

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds of Examples 1 to 64 were tested in the integrase assay and found to have IC50 values of less than about 1 micromolar.

Further description on conducting the assay using preassembled complexes is found in Wolfe, A. L. et al, *J. Virol.* 1996,70: 1424-1432, Hazuda et al., *J. Virol* 1997, H: 7005-7011; Hazuda et al, *Drug Design and Discovery* 1997, 15: 17-24; and Hazuda et al, *Science* 2000, 287: 646-650.

Example 67

Assay for Inhibition of HIV Replication

Assays for the inhibition of acute HIV infection of T-lymphoid cells were conducted in accordance with Vacca, J. P. et al., *Proc. Natl. Acad. Set USA* 1994, 91: 4096. Representative compounds of the present invention exhibit inhibition of HIV replication in this assay (also referred to herein as the "spread assay"). For example, the compounds of Examples 1 to 64 were tested in this assay and found to have IC$_{95}$ values of less than about 10 micromolar.

Example 68

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention that were tested in the spread assay (see Example 67) were examined for cytotoxicity up to a concentration of 10 micromolar, and no cytotoxicity was exhibited. In particular, the compounds set forth in Examples 1 to 64 exhibited no cytotoxicity at concentrations up to 10 micromolar.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I, or a pharmaceutically acceptable salt thereof:

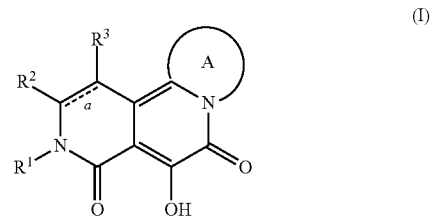

wherein:

bond "---a---" in the ring is a single bond or a double bond;
R$^1$ is C$_{1-6}$ alkyl, R$^J$, or C$_{1-6}$ alkyl substituted with R$^J$ wherein R$^J$ is CycA, AryA, HetA, or HetP;
R$^2$ is H or C$_{1-6}$ alkyl;

$R^3$ is:
(1) H,
(2) halogen,
(3) CN,
(4) $C_{1-6}$ alkyl,
(5) $C_{1-6}$ haloalkyl,
(6) $C_{1-6}$ alkyl substituted with OH, O—$C_{1-6}$ alkyl, O—$C_{1-6}$ haloalkyl, CN, $N(R^A)R^B$, $C(O)N(R^A)R^B$, $C(O)R^A$, $CO_2R^A$, $C(O)$—$N(R^A)$—$C_{1-6}$ alkylene-$OR^B$ with the proviso that the $N(R^A)$ moiety and the $OR^B$ moiety are not both attached to the same carbon of the $C_{1-6}$ alkylene moiety, $SR^A$, $S(O)R^A$, $SO_2R^A$, $SO_2N(R^A)R^B$, $N(R^A)C(O)R^B$, $N(R^A)CO_2R^B$, $N(R^A)SO_2R^B$, $N(R^A)SO_2N(R^A)R^B$, $N(R^A)C(O)N(R^A)R^B$, or $OC(O)N(R^A)R^B$,
(7) $C(O)R^A$,
(8) $CO_2R^A$,
(9) $C(O)N(R^A)R^B$,
(10) $C(O)$—$N(R^A)$—$C_{1-6}$ alkylene-$OR^B$ with the proviso that the $N(R^A)$ moiety and the $OR^B$ moiety are not both attached to the same carbon of the $C_{1-6}$ alkylene moiety,
(11) $SR^A$,
(12) $S(O)R^A$,
(13) $SO_2R^A$,
(14) $SO_2N(R^A)R^B$,
(15) $N(R^A)R^B$,
(16) $N(R^A)C(O)R^B$,
(17) $N(R^A)C(O)OR^B$;
(18) $N(R^A)C(O)N(R^A)R^B$,
(19) $N(R^A)C(O)C(O)N(R^A)R^B$,
(20) $N(R^A)SO_2R^B$,
(21) $N(R^A)SO_2N(R^A)R^B$,
(22) $OC(O)N(R^A)R^B$, or
(23) Y—$R^K$ wherein:
Y is a single bond, $C_{1-6}$ alkylene, O, O—$C_{1-6}$ alkylene, $C_{1-6}$ alkylene-O, C(O), C(O)—$C_{1-6}$ alkylene, $C_{1-6}$ alkylene-C(O), C(O)—$C_{1-6}$ alkylene-O, C(O)—$C_{1-6}$ alkylene-O—$C_{1-6}$ alkylene, $C(O)N(R^A)$, $C(O)N(R^A)$—$C_{1-6}$ alkylene, $C_{1-6}$ alkylene-$C(O)N(R^A)$, $C_{1-6}$ alkylene-$C(O)N(R^A)$—$C_{1-6}$ alkylene, S(O), $S(O)_2$, S(O)—$C_{1-6}$ alkylene, $S(O)_2$—$C_{1-6}$ alkylene, $C_{1-6}$ alkylene-S(O), or $C_{1-6}$ alkylene-$S(O)_2$; and
$R^K$ is CycB, AryB, HetB, or HetQ;

or as an alternative, when bond "‑‑‑ a ‑‑‑" is a double bond, $R^2$ and $R^3$ together with the carbon atoms to which each is attached form:
(i) a benzene ring which is optionally substituted with a total of from 1 to 4 substituents wherein (a) from zero to 4 substituents are each independently one of substituents (1) to (25) as defined in part (i) of the definition of AryA and (b) from zero to 2 substituents are each independently one of the substituents (1) to (6) as defined in part (ii) of the definition of AryA, or
(ii) a 5- or 6-membered heteroaromatic ring containing from 1 to 4 heteroatoms independently selected from N, O and S, wherein the heteroaromatic ring is optionally substituted with a total of from 1 to 3 substituents wherein (a) from zero to 3 substituents are each independently one of substituents (1) to (26) as defined in part (i) of the definition of HetA and (b) from zero to 2 substituents are each independently one of the substituents (1) to (6) as defined in part (ii) of the definition of HetA;

ring A is a 7-membered, saturated or mono-unsaturated heterocyclic ring containing in addition to the nitrogen shared with the naphthyridine ring from 1 to 3 heteroatoms independently selected from N, O, and S, wherein each S is optionally oxidized to S(O) or $S(O)_2$; and wherein the saturated or mono-unsaturated heterocyclic ring is optionally substituted with a total of from 1 to 6 substituents, wherein:
(i) from zero to 6 substituents are each independently:
(1) halogen,
(2) $C_{1-6}$ alkyl,
(3) $C_{1-6}$ haloalkyl,
(4) $C_{1-6}$ alkyl substituted with OH, O—$C_{1-6}$ alkyl, O—$C_{1-6}$ haloalkyl, CN, $N(R^A)R^B$, $C(O)N(R^A)R^B$, $C(O)R^A$, $CO_2R^A$, $C(O)$—$N(R^A)$—$C_{1-6}$ alkylene-$OR^B$ with the proviso that the $N(R^A)$ moiety and the $OR^B$ moiety are not both attached to the same carbon of the $C_{1-6}$ alkylene moiety, $SR^A$, $S(O)R^A$, $SO_2R^A$, $SO_2N(R^A)R^B$, $N(R^A)C(O)R^B$, $N(R^A)CO_2R^B$, $N(R^A)SO_2R^B$, $N(R^A)SO_2N(R^A)R^B$, $N(R^A)C(O)N(R^A)R^B$, $OC(O)N(R^A)R^B$, $OC(O)R^A$,
(5) O—$C_{1-6}$ alkyl.
(6) O—$C_{1-6}$ haloalkyl,
(7) oxo,
(8) $=C(R^A)R^B$,
(9) $C(O)N(R^A)R^B$,
(10) $C(O)C(O)N(R^A)R^B$,
(11) $C(O)R^A$,
(12) $CO_2R^A$,
(13) $SR^A$,
(14) $S(O)R^A$,
(15) $SO_2R^A$,
(16) $SO_2N(R^A)R^B$, or
(17) OH, and
(ii) from zero to 2 substituents are each Z—$R^L$, wherein:
each Z is independently a single bond, $C_{1-6}$ alkylene, O, O—$C_{1-6}$ alkylene, $C_{1-6}$ alkylene-O, C(O), C(O)—$C_{1-6}$ alkylene, $C_{1-6}$ alkylene-C(O), C(O)—$C_{1-6}$ alkylene-O, C(O)—$C_{1-6}$ alkylene-O—$C_{1-6}$ alkylene, $C(O)N(R^A)$, $C(O)N(R^A)$—$C_{1-6}$ alkylene, $C_{1-6}$ alkylene-$C(O)N(R^A)$, $C_{1-6}$ alkylene-$C(O)N(R^A)$—$C_{1-6}$ alkylene, S(O), $S(O)_2$, S(O)—$C_{1-6}$ alkylene, $S(O)_2$—$C_{1-6}$ alkylene, $C_{1-6}$ alkylene-S(O), or $C_{1-6}$ alkylene-$S(O)_2$; and
each $R^L$ is independently CycC, AryC; HetC, or HetR;
each $R^A$ is independently H or $C_{1-6}$ alkyl;
each $R^B$ is independently H or $C_{1-6}$ alkyl;
CycA is a $C_{3-8}$ cycloalkyl which is optionally substituted with a total of from 1 to 6 substituents, wherein:
(i) from zero to 6 substituents are each independently:
(1) halogen,
(2) CN,
(3) $C_{1-6}$ alkyl,
(4) OH,
(5) O—$C_{1-6}$ alkyl,
(6) $C_{1-6}$ haloalkyl, or
(7) O—$C_{1-6}$ haloalkyl, and
(ii) from zero to 2 substituents are each independently:
(1) CycD,
(2) AryD,
(3) HetD.
(4) HetZ,
(5) $C_{1-6}$ alkyl substituted with CycD, AryD, HetD, or HetZ, or
(6) C(O)-HetZ or C(O)C(O)-HetZ;
CycB independently has the same definition as CycA;
each CycC independently has the same definition as CycA;

AryA is an aryl which is optionally substituted with a total of from 1 to 5 substituents, wherein:
(i) from zero to 5 substituents are each independently:
(1) $C_{1-6}$ alkyl,
(2) $C_{1-6}$ alkyl substituted with OH, O—$C_{1-6}$ alkyl, O—$C_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, SO$_2$R$^A$, SO$_2$N(R$^A$)R$^B$, N(R$^A$)C(O)R$^B$, N(R$^A$)CO$_2$R$^B$, N(R$^A$)SO$_2$R$^B$, N(R$^A$)SO$_2$N(R$^A$)R$^B$, OC(O)N(R$^A$)R$^B$, N(R$^A$)C(O)N(R$^A$)R$^B$, or N(R$^A$)C(O)C(O)N(R$^A$)R$^B$,
(3) O—$C_{1-6}$ alkyl,
(4) $C_{1-6}$ haloalkyl,
(5) O—$C_{1-6}$ haloalkyl,
(6) OH,
(7) halogen,
(8) CN,
(9) NO$_2$,
(10) N(R$^A$)R$^B$,
(11) C(O)N(R$^A$)R$^B$,
(12) C(O)R$^A$;
(13) C(O)—$C_{1-6}$ haloalkyl,
(14) C(O)OR$^A$,
(15) OC(O)N(R$^A$)R$^B$,
(16) SR$^A$,
(17) S(O)R$^A$;
(18) SO$_2$R$^A$,
(19) SO$_2$N(R$^A$)R$^B$,
(20) N(R$^A$)SO$_2$R$^B$,
(21) N(R$^A$)SO$_2$N(R$^A$)R$^B$;
(22) N(R$^A$)C(O)R$^B$,
(23) N(R$^A$)C(O)N(R$^A$)R$^B$,
(24) N(R$^A$)C(O)C(O)N(R$^A$)R$^B$, or
(25) N(R$^A$)CO$_2$R$^B$, and
(ii) from zero to 2 substituents are each independently:
(1) CycD,
(2) AryD,
(3) HetD,
(4) HetZ,
(5) $C_{1-6}$ alkyl substituted with CycD, AryD, HetD, or HetZ, or
(6) C(O)-HetZ or C(O)C(O)-HetZ;
AryB independently has the same definition as AryA;
each AryC independently has the same definition as AryA;
HetA is a heteroaryl which is optionally substituted with a total of from 1 to 5 substituents, wherein:
(i) from zero to 5 substituents are each independently:
(1) $C_{1-6}$ alkyl,
(2) $C_{1-6}$ alkyl substituted with OH, O—$C_{1-6}$ alkyl, O—$C_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, SO$_2$R$^A$, SO$_2$N(R$^A$)R$^B$, N(R$^A$)C(O)R$^B$, N(R$^A$)CO$_2$R$^B$, N(R$^A$)SO$_2$R$^B$, N(R$^A$)SO$_2$N(R$^A$)R$^B$, OC(O)N(R$^A$)R$^B$, N(R$^A$)C(O)N(R$^A$)R$^B$, or N(R$^A$)C(O)C(O)N(R$^A$)R$^B$,
(3) O—$C_{1-6}$ alkyl,
(4) $C_{1-6}$ haloalkyl,
(5) O—$C_{1-6}$ haloalkyl,
(6) OH,
(7) oxo,
(8) halogen,
(9) CN,
(10) NO$_2$,
(11) N(R$^A$)R$^B$,
(12) C(O)N(R$^A$)R$^B$,
(13) C(O)R$^A$,
(14) C(O)—$C_{1-6}$ haloalkyl,
(15) C(O)OR$^A$,
(16) OC(O)N(R$^A$)R$^B$,
(17) SR$^A$,
(18) S(O)R$^A$,
(19) SO$_2$R$^A$,
(20) SO$_2$N(R$^A$)R$^B$,
(21) N(R$^A$)SO$_2$R$^B$,
(22) N(R$^A$)SO$_2$N(R$^A$)R$^B$,
(23) N(R$^A$)C(O)R$^B$,
(24) N(R$^A$)C(O)N(R$^A$)R$^B$,
(25) N(R$^A$)C(O)C(O)N(R$^A$)R$^B$, or
(26) N(R$^A$)CO$_2$R$^B$, and
(ii) from zero to 2 substituents are each independently:
(1) CycD,
(2) AryD,
(3) HetD,
(4) HetZ,
(5) $C_{1-6}$ alkyl substituted with CycD, AryD, HetD, or HetZ, or
(6) C(O)-HetZ or C(O)C(O)-HetZ;
HetB independently has the same definition as HetA;
each HetC independently has the same definition as HetA;
HetP is (i) a 4- to 7-membered, saturated or mono-unsaturated heterocyclic ring containing at least one carbon/atom and from 1 to 4 heteroatoms independently selected from N, O and S, where each S is optionally oxidized to S(O) or S(O)$_2$ or (ii) a 6- to 10-membered saturated or mono-unsaturated, bridged or fused heterobicyclic ring containing from 1 to 4 heteroatoms independently selected from N, O and S, where each S is optionally oxidized to S(O) or S(O)$_2$ and wherein the saturated or mono-unsaturated heterocyclic or heterobicyclic ring is optionally substituted with a total of from 1 to 4 substituents, wherein:
(i) from zero to 4 substituents are each independently halogen, $C_{1-6}$ alkyl, $C_{1-6}$ haloalkyl, O—$C_{1-6}$ alkyl, O—$C_{1-6}$ haloalkyl, oxo, C(O)N(R$^A$)R$^B$, C(O)C(O)N(R$^A$)R$^B$, C(O)R$^A$, CO$_2$R$^A$, SR$^A$, S(O)R$^A$, SO$_2$R$^A$, or SO$_2$N(R$^A$)R$^B$, and
(ii) from zero to 2 substituents are independently CycD, AryD, HetD, or $C_{1-6}$ alkyl substituted with CycD, AryD, HetP;
HetQ independently has the same definition as HetP;
each HetR independently has the same definition as HetP;
each CycD is independently a $C_{3-8}$ cycloalkyl which is optionally substituted with from 1 to 4 substituents each of which is independently halogen, $C_{1-6}$ alkyl, OH, O—$C_{1-6}$ alkyl, or $C_{1-6}$ haloalkyl;
each AryD is independently phenyl or naphthyl, wherein the phenyl or naphthyl is optionally substituted with from 1 to 5 substituents each of which is independently any one of the substituents (1) to (25) as set forth above in part (i) of the definition of AryA;
each HetD is independently a 5- or 6-membered heteroaromatic ring containing from 1 to 4 heteroatoms independently selected from N, O and S, wherein the heteroaromatic ring is optionally substituted with from 1 to 4 substituents each of which is independently any one of the substituents (1) to (26) as set forth above in part (i) of the definition of HetA;
each HetZ is independently a 4- to 7-membered, saturated or mono-unsaturated heterocyclic ring containing at least one carbon atom and from 1 to 4 heteroatoms independently selected from N, O and S where each S is optionally oxidized to S(O) or S(O)$_2$, wherein the saturated or mono-unsaturated heterocyclic ring is optionally substituted with from 1 to 4 substituents each of which is independently halogen, $C_{1-6}$ alkyl, $C_{1-6}$ haloalkyl, O—$C_{1-6}$ alkyl, O—$C_{1-6}$ haloalkyl, oxo, C(O)N($R^A$)$R^B$, C(O)C(O)N($R^A$)$R^B$, C(O)$R^A$, $CO_2R^A$, $SR^A$, S(O)$R^A$, $SO_2R^A$, or $SO_2N(R^A)R^B$, each aryl independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic; and each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$.

2. A compound according to claim 1, or a pharmaceutically acceptable salt thereof, wherein $R^1$ to $C_{1-6}$ alkyl substituted with $R^J$.

3. A compound according to claim 2, or a pharmaceutically acceptable salt thereof, wherein $R^J$ is AryA or HetA.

4. A compound according to claim 1, or a pharmaceutically acceptable salt thereof, wherein:
$R^2$ is H or $C_{1-6}$ alkyl; and
$R^3$ is H, $C_{1-6}$ alkyl, C(O)N($R^A$)$R^B$, $SO_2N(R^A)R^B$, or $C_{1-6}$ alkyl substituted with C(O)N($R^A$)$R^B$ or $SO_2N(R^A)R^B$.

5. A compound according to claim 1, or a pharmaceutically acceptable salt thereof, wherein the compound is a compound of Formula IIa:

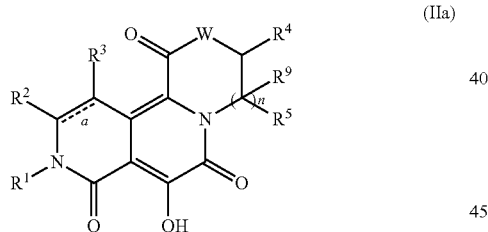

(IIa)

wherein n is 2;
W is O or N—$R^8$;
$R^4$ is:
  (1) H,
  (2) $C_{1-6}$ alkyl, or
  (3) $C_{1-6}$ alkyl substituted with OH or OC(O)$R^A$,
each $R^5$ is independently:
  (1) H,
  (2) $C_{1-6}$ alkyl,
  (3) $C_{1-6}$ alkyl substituted with OH,
  (4) OH, or
  (5) —$R^L$;
each $R^9$ is independently H or $C_{1-6}$ alkyl;
alternatively, $R^5$ and $R^9$ attached to the same ring carbon atom together form oxo or =C($R^A$)$R^B$;
and
$R^8$ is:
  (1) H,
  (2) $C_{1-6}$alkyl,
  (3) $C_{1-6}$ haloalkyl,
  (4) $C_{1-6}$ alkyl substituted with OH, O—$C_{1-6}$ alkyl, N($R^A$)$R^B$, C(O)N($R^A$)$R^B$, C(O)$R^A$, $CO_2R^A$, C(O)—N($R^A$)—$C_{1-6}$ alkylene-O$R^B$ with the proviso that the N($R^A$) moiety, and the O$R^B$ moiety are not both attached to the same carbon of the $C_{1-6}$ alkylene moiety, S(O)$R^A$, $SO_2R^A$, $SO_2N(R^A)R^B$, N($R^A$)C(O)$R^B$, N($R^A$)$SO_2R^B$, or OC(O)$R^A$, or
  (5) Z—$R^L$.

6. A compound according to claim 5, or a pharmaceutically acceptable salt thereof, wherein $R^1$ is:

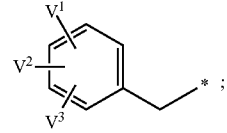

the asterisk * denotes the point of attachment of $R^1$ to the rest of the compound, $V^1$ and $V^2$ are each independently:
  (1) H,
  (2) $C_{1-4}$ alkyl,
  (3) OH,
  (4) O—$C_{1-4}$ alkyl,
  (5) $C_{1-4}$ haloalkyl,
  (6) O—$C_{1-4}$ haloalkyl,
  (7) halogen,
  (8) CN,
  (9) N($R^A$)$R^B$,
  (10) C(O)N($R^A$)$R^B$,
  (11) C(O)$R^A$,
  (12) C(O)O$R^A$,
  (13) S$R^A$,
  (14) S(O)$R^A$,
  (15) $SO_2R^A$,
  (16) N($R^A$)$SO_2R^B$,
  (17) N($R^A$)$SO_2N(R^A)R^B$,
  (18) N($R^A$)C(O)$R^B$,
  (19) N($R^A$)C(O)C(O)N($R^A$)$R^B$,
  (20) HetD,
  (21) HetZ, or
  (22) C(O)-HetZ,
    wherein
    HetD is a 5- or 6-membered heteroaromatic ring containing a total of from 1 to 3 heteroatoms independently selected from 1 to 3 N atoms, from zero to 1 O atom, and from zero to 1 S atom, wherein the heteroaromatic ring is optionally substituted with 1 or 2 substituents each of which is independently $C_{1-4}$ alkyl, OH, O—$C_{1-4}$ alkyl, halogen, CN, C(O)N($R^A$)$R^B$, C(O)$R^A$, C(O)O$R^A$, or $SO_2R^A$,
    HetZ is a 5- or 6-membered saturated heterocyclic ring containing a total of from 1 to 2 heteroatoms selected from 1 to 2 N atoms, zero to 1 O atom, and zero to 1 S atom, wherein the S atom is optionally S(O) or $SO_2$, wherein the saturated heterocyclic ring is optionally substituted with from 1 to 2 substituents each of which is independently $C_{1-4}$ alkyl, oxo, C(O)N($R^A$)$R^B$, C(O)$R^A$, $CO_2R^A$, or $SO_2R^A$,
    and with the proviso that when HetZ is attached to the rest of the compound via the C(O) moiety, then HetZ is attached to the C(O) via a ring N atom;

or alternatively $V^1$ and $V^2$ are respectively located on adjacent carbons in the phenyl ring and together form methylenedioxy or ethylenedioxy; and $V^3$ is;
(1) H,
(2) $C_{1-4}$ alkyl,
(3) O—$C_{1-4}$ alkyl,
(4) $C_{1-4}$ haloalkyl,
(5) O—$C_{1-4}$ haloalkyl, or
(6) halogen.

7. A compound according to claim 6, or a pharmaceutically acceptable salt thereof, wherein the compound is selected from the group consisting of:

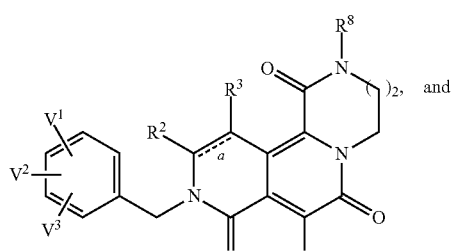
(IIIb)

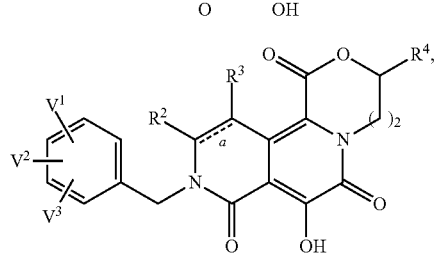
(IIIc)

wherein:
$R^2$ and $R^3$ are each independently H or $C_{1-4}$ alkyl;
$R^4$ is:
(1) H,
(2) $C_{1-4}$ alkyl, or
(3) $C_{1-4}$ alkyl substituted with OH or OC(O)$R^A$,
$R^8$ is:
(1) H,
(2) $C_{1-4}$ alkyl,
(3) $C_{1-4}$ haloalkyl,
(4) $C_{1-4}$ alkyl substituted with OH, O—$C_{1-4}$ alkyl, N($R^A$)$R^B$, C(O)N($R^A$)$R^B$, C(O)$R^A$, CO$_2$$R^A$, S(O)$R^A$, SO$_2$$R^A$, SO$_2$N($R^A$)$R^B$, N($R^A$)C(O)$R^B$, N($R^A$SO$_2$$R^B$, OC(O)$R^A$,
(5) $C_{1-4}$ alkylene-HetC, of
(6) $C_{1-4}$ alkylene-HetR;
HetC is a 5- or 6-membered heteroaromatic ring containing a total of from 1 to 3 heteroatoms independently selected froth 1 to 3 N atoms, froth zero to 1 O atom, and from zero to 1 S atom, wherein the heteroaromatic ring is optionally substituted with 1 or 2 substituents each of which is independently $C_{1-4}$ alkyl, OH, O—$C_{1-4}$ alkyl, halogen, CN, C(O)N($R^A$)$R^B$, C(O)$R^A$, C(O)O$R^A$, or SO$_2$$R^A$;
HetR is a 5- or 6-membered saturated heterocyclic ring containing a total of from 1 to 2 heteroatoms selected from 1 to 2 N atoms, zero to 1 O atom, and zero to 1 S atom, wherein the S atom is optionally S(O) or SO$_2$, wherein the saturated heterocyclic ring is optionally substituted with from 1 to 2 substituents each of which is independently $C_{1-4}$ alkyl, oxo, C(O)N($R^A$)$R^B$, C(O)$R^A$, CO$_2$$R^A$, or SO$_2$$R^A$;

each $R^A$ is independently H or $C_{1-4}$ alkyl; and
each $R^B$ is independently H or $C_{1-4}$ alkyl.

8. A compound according to claim 7, or a pharmaceutically acceptable salt thereof, wherein:

bond "−−a−−" in the ring is a single bond;
$R^2$ and $R^3$ are each independently H or CH$_3$;
$R^4$ is:
(1) H,
(2) CH$_3$,
(3) CH$_2$CH$_3$,
(4) CH$_2$CH$_2$CH$_3$,
(5) CH(CH$_3$)$_2$,
(3) (CH$_2$)$_{1-3}$—OH, or
(4) (CH$_2$)$_{1-3}$—OC(O)$R^A$;
$R^8$ is:
(1) H,
(2) CH$_3$,
(3) CH$_2$CH$_3$,
(4) CH$_2$CH$_2$CH$_3$,
(5) CH(CH$_3$)$_3$,
(6) CH$_2$CH$_2$CH$_2$CH$_3$,
(7) C(CH$_3$)$_3$,
(8) CH$_2$CH(CH$_3$)$_2$,
(9) CH(CH$_3$)CH$_2$CH$_3$,
(10) CF$_3$,
(11) CH$_2$CF$_3$,
(12) (CH$_2$)$_{2-4}$—U, wherein U is OH, OCH$_3$, N($R^A$)$R^B$, N($R^A$)C(O)$R^B$, N($R^A$)SO$_2$$R^B$, or OC(O)$R^A$,
(13) (CH$_2$)$_{1-4}$—V, wherein V is C(O)N($R^A$)$R^B$, C(O)$R^A$, CO$_2$$R^A$, S(O)$R^A$, SO$_2$$R^A$, or SO$_2$N($R^A$)$R^B$,
(14) (CH$_2$)$_{2-4}$-HetC, or
(15) (CH$_2$)$_{2-4}$-HetR;
HetC is a 5-membered heteroaromatic ring selected from the group consisting of:

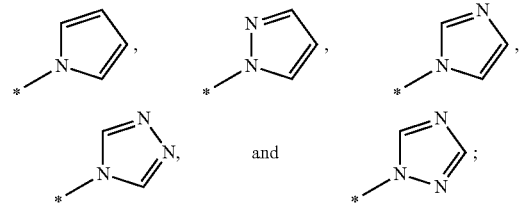

HetR is a 5- or 6-membered saturated heterocyclic ring selected from the group consisting of:

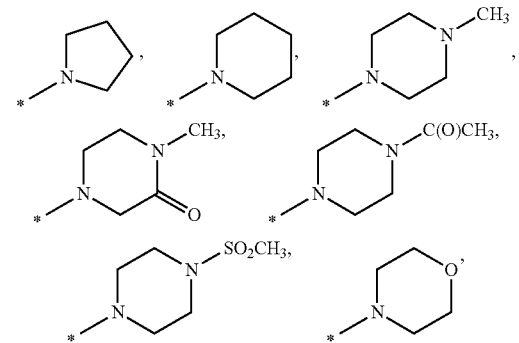

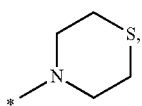 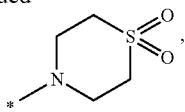

the asterisk * in HetC and HetR denotes the point of attachment to the rest of the molecule;
each $R^A$ is independently H or $CH_3$;
each $R^B$ is independently H or $CH_3$;
$V^1$ and $V^2$ are each independently:
- (1) H,
- (2) $CH_3$,
- (3) $CF_3$,
- (4) OH,
- (5) $OCH_3$,
- (6) Cl, Br, or F,
- (7) CN,
- (8) $C(O)NH_2$,
- (9) $C(O)NH(CH_3)$,
- (10) $C(O)N(CH_3)_2$, or
- (11) $SO_2CH_3$; and $V^3$ is H, Cl, Br, F, $CH_3$, or $OCH_3$.

9. The compound according to claim 1, or a pharmaceutically acceptable salt thereof, which is a compound selected from the group consisting of:
- 10-(3-chloro-4-fluorobenzyl)-8-hydroxy-2-methyl-2,3,4,5,11,12-hexahydro-[1,4]-diazepino[2,1-a]-2,6-naphthyridine-1,7,9(10H)-trione; and
- 10-(3-chloro-4-fluorobenzyl)-8-hydroxy-2,3,4,5,11,12-hexahydro-[1,4]diazepino[2,1-a]-2,6-naphthyridine-1,7,9(10H)-trione;
- a]-2,6-naphthyridine-2,5,7(3H)-trione.

10. A pharmaceutical composition comprising an effective amount of a compound according to claim 1, or a pharmaceutically acceptable salt thereof, and a pharmaceutically acceptable carrier.

11. A method for the treatment of infection by HIV or for the treatment of AIDS in a subject in need thereof, which comprises administering to the subject an effective amount of the compound according to claim 1, or a pharmaceutically acceptable salt thereof.

* * * * *